(12) United States Patent
Han et al.

(10) Patent No.: US 10,336,733 B2
(45) Date of Patent: Jul. 2, 2019

(54) ARYL ACYLSULFONAMIDES AS BLT1 ANTAGONISTS

(71) Applicants: Merck Sharp & Dohme Corp., Rahway, NJ (US); Yongxin Han, Needham, MA (US); Jongwon Lim, Lexington, MA (US); Satyanarayana Tummanapalli, Hyderabad (IN); Phieng Siliphaivanh, Newton, MA (US); Kerrie Spencer, Woonsocket, RI (US)

(72) Inventors: Yongxin Han, Needham, MA (US); Jongwon Lim, Lexington, MA (US); Satyanarayana Tummanapalli, Hyderabad (IN); Phieng Siliphaivanh, Newton, MA (US); Kerrie Spencer, Woonsocket, RI (US)

(73) Assignee: Merk Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/767,371

(22) PCT Filed: Nov. 28, 2016

(86) PCT No.: PCT/US2016/063806
§ 371 (c)(1),
(2) Date: Apr. 11, 2018

(87) PCT Pub. No.: WO2017/095722
PCT Pub. Date: Jun. 8, 2017

(65) Prior Publication Data
US 2018/0305342 A1   Oct. 25, 2018

Related U.S. Application Data

(60) Provisional application No. 62/260,950, filed on Nov. 30, 2015.

(51) Int. Cl.
| | | |
|---|---|---|
| *C07D 417/06* | (2006.01) | |
| *C07D 413/06* | (2006.01) | |
| *C07D 311/22* | (2006.01) | |
| *C07D 405/06* | (2006.01) | |
| *A61K 31/353* | (2006.01) | |
| *A61K 9/20* | (2006.01) | |

(52) U.S. Cl.
CPC .......... *C07D 405/06* (2013.01); *A61K 9/2054* (2013.01); *A61K 31/353* (2013.01); *C07D 311/22* (2013.01); *C07D 413/06* (2013.01); *C07D 417/06* (2013.01)

(58) Field of Classification Search
CPC .. C07D 417/06; C07D 413/06; C07D 311/22; C07D 405/06; A61K 31/353
See application file for complete search history.

(56) References Cited

U.S. PATENT DOCUMENTS

| | | |
|---|---|---|
| 5,032,598 A | 7/1991 | Baldwin et al. |
| 5,215,989 A | 6/1993 | Baldwin et al. |
| 5,550,152 A | 8/1996 | Koch et al. |
| 5,552,435 A | 9/1996 | Koch |
| 5,864,043 A | 1/1999 | Narr et al. |
| 5,939,452 A | 8/1999 | Dombroski et al. |
| 5,998,451 A | 12/1999 | Eggler et al. |
| 6,051,601 A | 4/2000 | Dombroski et al. |
| 6,117,874 A | 9/2000 | Dombroski et al. |
| 6,133,286 A | 10/2000 | Dombroski et al. |
| 2003/0078260 A1 | 4/2003 | O'Connor et al. |
| 2007/0032479 A1 | 2/2007 | Leventer et al. |
| 2009/0054466 A1 | 2/2009 | Dominique et al. |
| 2009/0227603 A1 | 9/2009 | Dominique et al. |
| 2009/0253684 A1 | 10/2009 | Dominique et al. |
| 2010/0016355 A1 | 1/2010 | Gil et al. |
| 2014/0135332 A1 | 5/2014 | Haydon et al. |

FOREIGN PATENT DOCUMENTS

| | | |
|---|---|---|
| EP | 0431945 A2 | 6/1991 |
| EP | 0518819 B1 | 12/1992 |
| EP | 1270000 A2 | 1/2003 |
| WO | WO1993015066 A1 | 8/1993 |
| WO | WO1993015067 A1 | 8/1993 |
| WO | WO1996006604 A2 | 3/1996 |
| WO | WO1996011920 A1 | 4/1996 |
| WO | WO1996011925 A1 | 4/1996 |
| WO | WO1996041645 A1 | 12/1996 |
| WO | WO1998011119 A1 | 3/1998 |
| WO | WO2003007947 A1 | 1/2003 |

(Continued)

OTHER PUBLICATIONS

Colagiuri et al., American Journal of Public Health, Sep. 2006, vol. 96, No. 9, pp. 1562-1569. (Year: 2006).*

(Continued)

*Primary Examiner* — Laura L Stockton
(74) *Attorney, Agent, or Firm* — Baerbel R. Brown; Catherine D. Fitch

(57) ABSTRACT

Novel compounds of the structural formula (I), and the pharmaceutically acceptable salts thereof, are antagonists of leukotriene B$_4$ receptor 1 (BLT1) and may be useful in the treatment, prevention and suppression of diseases mediated by the leukotriene B$_4$ receptor 1 (BLT1). The compounds of the present invention may be useful in the treatment of Type 2 diabetes mellitus, insulin resistance, hyperglycemia, dyslipidemia, lipid disorders, obesity, hypertension, Non-alcoholic fatty liver disease/nonalcoholic steatoepatitis, metabolic syndrome, atherosclerosis, and cancer.

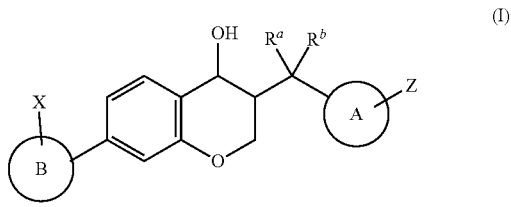

20 Claims, No Drawings

(56) References Cited

FOREIGN PATENT DOCUMENTS

| WO | WO2013106238 A1 | 7/2013 |
|----|-----------------|--------|
| WO | WO2017095722 A1 | 6/2017 |
| WO | WO2017095723 A1 | 6/2017 |
| WO | WO2017095724 A1 | 6/2017 |
| WO | WO2017095725 A1 | 6/2017 |

OTHER PUBLICATIONS

Bruno et al., Expert Opinion Emerging Drugs, (2005), 10(4), pp. 747-771. (Year: 2005).*

Park, Diabetes Research and Clinical Practice 66S (2004), S33-S35. (Year: 2004).*

Curtis et al., The Journal of the American Board of Family Practice, vol. 18, pp. 37-43, (2005) (Year: 2005).*

Chambers, R. J. et al., Synthetic Approaches to 2-(4-Hydroxy-7-Chromanyl)Benzoic Acids As Antagonists of Leukotriene B4, Bioorganic & Medicinal Chemistry Letters, 1998, p. 1787-1790, vol. 8.

Dalvie, D. K. et al., Metabolism of CP-195,543, a leukotriene B4 receptor antagonist, in the Long-Evans rat and Cynomolgus monkey, Xenobiotica, 1999, p. 1123-1140, vol. 19, No. 11.

Haeggstrom, Jesper, Z., Leukotriene A4 Hydrolase/Aminopeptidase, the Gatekeeper of Chemotactic Leukotriene B4 Biosynthesis, The Journal of Biological Chemistry, 2004, p. 50639-50642, vol. 279, No. 49.

Heller, Eric, A. et al., Inhibition of Atherogenesis in BLT1-Deficient Mice Reveals a Role for LTB4 and BLT1 in Smooth Muscle Cell Recruitment, Circulation, 2005, p. 578-586, vol. 112.

International Search Report for PCT/US2016063806 dated Jan. 30 2017, 11 pages.

Jeon, Woo-Kwang, et al., The proinflammatory LTB4/BLT1 Signal axis confers resistance to TGF-B1-induced growth inhibition by targeting Smad3 linker region, Oncotarget, 2015, p. 41650-41666, vol. 6, No. 39.

Jones, Brian, P., et al., The Synthesis of an Aminohexyl-Containing Analog of the Chromanol Leukotriene B4 Receptor Antagonist CP-195543: A Scaffold for the Preparation of Derivatized Analogs, Heterocycles, 2000, p. 1713-1724, vol. 53, No. 8.

Khojasteh-Bakht, S. C. et al., Identification of the human cytochrome P450s responsible for the in vitro metabolism of a leukotriene B4 receptor antagonist, CP-195,543, Xenobiotica, 2003, p. 1201-1210, vol. 33, No. 12.

Koch, Kevin, et al., (+)-1-(3S,4R)-[3-(4-Phenylbenzyl)-4-hydroxychroman-7-yl]cyclopentane Carboxylic Acid, a Highly Potent, Selective Leukotriene B4 Antagonist with Oral Activity in the Murine Collagen-Induced Arthritis Model, Journal of Medicinal Chemistry, 1994, p. 3197-3199, vol. 37, No. 20.

Reiter, Lawrence, A. et al., 3-Substituted-4-Hydroxy-7-Chromanylacetic Acid Derivatives As Antagonists of the Leukotriene B4 (LTB4) Receptor, Bioorganic & Medicinal Chemistry Letters, 1997, p. 2307-2312, vol. 7, No. 17.

Reiter, Lawrence, A., et al., trans-3-Benzyl-4-Hydroxy-7-Chromanylbenzoic Acid Derivatives As Antagonists of the Leukotriene B4 (LTB4) Receptor, Bioorganic & Medicinal Chemistry Letters, 1998, p. 1781-1786, vol. 8.

Samuelsson, Bengt, et al., Leukotrienes and Lipoxins: Structures, Biosynthesis, and Biological Effects, Articles, 1987, p. 1171-1176, vol. 237.

Showell, H. J. et al., The In Vitro and In Vivo Pharmacologic Acitvity of the Potent and Selective Leukotriene B4 Receptor Antagonist CP-105696, The Journal of Pharmacology and Experimental Therapeutics, 1995, p. 176-184, vol. 273, No. 1.

Showell, H. J., et al., The Preclinical Pharmacological Profile of the Potent and Selective Leukotriene B4 Antagonist CP-195543, The Journal of Pharmacology and Experimental Therapeutics, 1998, p. 946-954, vol. 285, No. 3.

Spite, Matthew, et al., Deficiency of the Leukotriene B4 Receptor, BLT-1, Protects against Systemic Insulin Resistance in Diet-Induced Obesity, The Journal of Immunology, 2011, p. 1942-1949, vol. 187.

Wang, Luman, et al., BLT1-dependent Alveolar Recruitment of CD4+CD25+ Foxp3+ Regulatory T Cells Is for Important Resolution of Acute Lung Injury, Am J Rspir Crit Care Med, 2012, p. 989-998, vol. 186, Issue 10.

Yokomizo, Takehiko, et al., A G-protein-coupled receptor for leukotriene B4 that mediates chemotaxis, Nature, 1997, p. 620-624, vol. 387.

Yokota, Yosuke, et al., Absence of LTB4/BLT1 axis facilitates generation of mouse GM-CSF-induced long-lasting antitumor immunologic memory by enhancing innate and adaptive immune systems, Blood, 2012, p. 3444-3454, vol. 120, No. 17.

* cited by examiner

ARYL ACYLSULFONAMIDES AS BLT1 ANTAGONISTS

CROSS-REFERENCE TO RELATED APPLICATIONS

This application is a U.S. National Phase application under 35 U.S.C. § 371 of PCT Application PCT/US16/063806, filed Nov. 28, 2016, which claims priority from and the benefit of US Provisional Application U.S. Ser. No. 62/260,950, filed Nov. 30, 2015.

BACKGROUND OF THE INVENTION

Diabetes mellitus is a disease derived from multiple causative factors and characterized by elevated levels of plasma glucose (hyperglycemia) in the fasting state or after administration of glucose during an oral glucose tolerance test. There are two generally recognized forms of diabetes. In Type 1 diabetes, or insulin-dependent diabetes mellitus (IDDM), patients produce little or no insulin, the hormone which regulates glucose homeostasis. In Type 2 diabetes, or noninsulin-dependent diabetes mellitus (NIDDM), insulin is still produced in the body, however patients have a resistance to the effects of insulin in stimulating glucose and lipid metabolism in the insulin-sensitive tissues such as muscle, liver and adipose. Early stage of type 2 diabetes patients often have normal levels of insulin, and may have hyperinsulinemia (elevated plasma insulin levels), as the islet beta cells try to compensate for the reduced effectiveness of insulin by secreting increased amounts of insulin. This lack of responsiveness to insulin results in insufficient insulin-mediated activation of uptake, oxidation and storage of glucose in muscle; inadequate insulin-mediated repression of lipolysis in adipose tissue and glucose output from the liver.

Persistent or uncontrolled hyperglycemia is associated with increased and premature morbidity and mortality. Impaired glucose homeostasis is associated both directly and indirectly with obesity, hypertension, and alterations of the lipid, lipoprotein and apolipoprotein metabolism, as well as other metabolic and hemodynamic diseases. Patients with Type 2 diabetes mellitus have a significantly increased risk of macrovascular and microvascular complications, including atherosclerosis, coronary heart disease, stroke, peripheral vascular disease, hypertension, nephropathy, neuropathy, and retinopathy. Therefore, therapeutic control of glucose homeostasis, lipid metabolism, obesity, and hypertension are critically important in the clinical management and treatment of diabetes mellitus.

Patients who have insulin resistance often have Metabolic Syndrome with complications including vascular dysfunctions, atherosclerosis and coronary heart disease, (as defined in the Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670).

Pharmacologic treatments for diabetes have largely focused on three areas of pathophysiology: (1) hepatic glucose production (biguanides, such as phenformin and metformin), (2) insulin resistance (PPAR agonists, such as rosiglitazone, troglitazone, engliazone, balaglitazone, and pioglitazone), (3) insulin secretion (sulfonylureas, such as tolbutamide, glipizide and glimipiride); (4) incretin hormone mimetics (GLP-1 derivatives and analogs, such as exenatide, liraglutide, dulaglutide, semaglutide, lixisenatide, albiglutide and taspoglutide); and (5) inhibitors of incretin hormone degradation (DPP-4 inhibitors, such as sitagliptin, alogliptin, vildagliptin, linagliptin, denagliptin and saxagliptin).

The two best known biguanides, phenformin and metformin, demonstrated reasonable efficacy in controlling hyperglycemia with the adverse effect of lactic acidosis and nausea/diarrhea. PPAR gamma agonists, such as rosiglitazone and pioglitazone, are modestly effective in reducing plasma glucose and hemoglobin A1C. However, the currently marketed glitazones do not greatly improve lipid metabolism and may negatively effect on the lipid profile. The administration of insulin secretagogues, such as the sulfonylureas (e.g. tolbutamide, glipizide, and glimepiride) can result in hypoglycemia; their administration must therefore be carefully controlled.

Leukotriene $B_4$ ($LTB_4$) is a pro-inflammatory lipid mediator generated from arachidonic acid through the activities of 5-lipoxygenase, 5-lipoxygenase activating protein (FLAP) and leukotriene A4 hydrolase (LTA4H) (Samuelsson et al., Science 1987; 237:1171-1176, Haeggstrom, J Z, J. Biol Chem. 2004; 279:50639-50642).

$LTB_4$ is a chemoattractant and regulates the proinflammatory cytokines by binding to a G-protein coupled receptor leukotriene $B_4$ receptor 1 (BLT1) and leukotriene $B_4$ receptor 2 (BLT2). $LTB_4$ has been considered an endogenous mediator for the recruitment of inflammatory cells in acute and chronic disease states and has been associated with inflamed tissue in rheumatoid arthritis, psoriasis, inflammatory bowel disease and asthmas; and $LTB_4$ receptor antagonists were developed for the treatment of variety of inflammatory diseases (Dalvie et al., Xenobiotica, 1999, Vol. 29, No. 11, 11-23-1140). The potent biological actions of $LTB_4$ are mediated primarily through a high affiniity interaction with a G-protein coupled receptor termed BLT-1 (Yokomizo et al., Nature, 1997; 387:620-624). $LTB_4$:BLT1 plays an important role in host defense during acute infection. Choronic activation of the $LTB_4$:BLT1 pathway contributes to the development of inflammatory diseases such as atherosclerosis and arthritis. BLT1, a high affinity receptor specific for $LTB_4$, is demonstrated to express predominantly in leucocytes. BLT2, a low affinity receptor for LTB4, is ubiquitiously expressed. In the 1990s, BLT1 and dual BLT1/BLT2 antagonists were pursued for treating inflammatory conditions including asthma, chronic obstructive pulmonary disease, inflammatory bowel disease, cystic fibrosis, rheumatic arthritis and cancer. Recent publications suggest a potential BLT1 involvement in mediating tumor progression and the blockade of LTB4/BLT1 pathways could generate benefits in controlling tumor growth (Yokota et al., *Blood*, 2012; 120:3444-3454; Woo-Kwang Jeon et al., The proinflammatory LTB4/BLT1 signal axis confers resistance to TGF-β1-induced growth inhibition by targeting Smad3 linker region, Oncotarget, Advance Publications 2015; and Wang, Luman et al., Am J Respir Crit Care Med 2012, 186: 989-998).

It was recently found that deficiency of BLT1 protects against the development of insulin resistance in diet-induced obesity by regulating adipose tissue macrophage accumulation and inflammation in insulin-sensitive tissues (Spite et al., J Immunol., 2011 Aug. 15, 187(4), 1942-1949). The study also found that 1) BLT1 deficiency improves glucose and insulin-tolerance in diet induced obese mouse model; 2) BLT1 is a key regulator of macrophage accumulation in adipose tissue and systemic insulin signaling; and 3) the BLT1 pathway points towards new avenues for the therapeutic management of obesity and type 2 diabetes (Spite et al., J Immunol., 2011, 15, 187(4), 1942-1949).

Compounds that are antagonists of leukotriene $B_4$ receptor 1 (BLT1) may be useful to treat type 2 diabetes mellitus, obesity, hypertension, dyslipidemia, cancer, and metabolic syndrome, as well as cardiovascular diseases, such as myocardial infarction and stroke, by improving glucose and lipid metabolism, and by improving whole body energy homeostasis.

Leukotriene $B_4$ ($LTB_4$) receptor antagonists are disclosed in: WO 93/015066; WO 93/015067; WO 96/006604; WO 96/011920; WO 96/011925; WO 96/41645; WO 98/011119; WO 03/007947; WO 13/106238; U.S. Pat. Nos. 5,550,152; 5,552,435; 5,939,452; 6,051,601; 6,117,874; 6,133,286; US 2009/054466; US 2009/253684; US 2009/227603; EP00518819; Koch et al., J. Med. Chem., 1994, Vol. 37, No. 20, pp. 3197-3199; Showell et al., J. of Pharmacology and Experimental Therapeutics, Vol. 273, No. 1, pp. 176-184, 1995; Reiter et al., Bioorg. Med. Chem Lett. 8 (1998) 1781-1786; Chambers et al., Bioorg. Med. Chem. Lett. 8 (1998) 1787-1790; Reiter et al., Bioorg. Med. Chem. Lett. 7 (1997) 2307-2312; Showell et al., J. of Pharmacology and Experimental Therapeutics, Vol. 285, No. 3, pp. 946-954, 1998; Dalvie et al., Xenobiotica, 1999, Vol. 29, No. 11, 11-23-1140; Jones et al., Heterocycles, Vol. 53, No. 8, 2000, pp. 1713-1724; and Khojasteh-Bakht et al., Xenobiotica, December 2003, Vol. 33, No. 12, 1201-1210.

Hydroxy tetralins are disclosed in U.S. Pat. Nos. 5,215,989; 5,032,598; and EP 0 431 945.

SUMMARY OF THE INVENTION

The present invention relates to novel substituted compounds of structural formula I:

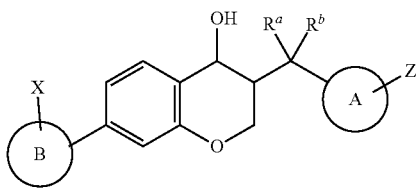

and pharmaceutically acceptable salts thereof. The compounds of structural formula I, and embodiments thereof, are antagonists of leukotriene $B_4$ receptor 1 (BLT1 antagonists) and may be useful in the treatment, prevention and suppression of diseases, disorders and conditions mediated by antagonism of the BLT1 receptor, such as Type 2 diabetes mellitus, insulin resistance, hyperglycemia, dyslipidemia, lipid disorders, obesity, hypertension, Non-alcoholic fatty liver disease/nonalcoholic steatohepatitis, metabolic syndrome, atherosclerosis, and cancer.

The present invention also relates to pharmaceutical compositions comprising the compounds of the present invention and a pharmaceutically acceptable carrier. The present invention also relates to methods for the treatment, control or prevention of disorders, diseases, and conditions that may be responsive to antagonism of the BLT1 receptor in a subject in need thereof by administering the compounds and pharmaceutical compositions of the present invention. The present invention also relates to the use of compounds of the present invention for manufacture of a medicament useful in treating diseases, disorders and conditions that may be responsive to the antagonism of the BLT1 receptor. The present invention is also concerned with treatment of these diseases, disorders and conditions by administering the compounds of the present invention in combination with a therapeutically effective amount of another agent that may be useful to treat the disease, disorder and condition. The invention is further concerned with processes for preparing the compounds of this invention.

DETAILED DESCRIPTION OF THE INVENTION

The present invention is concerned with novel compounds of structural Formula I:

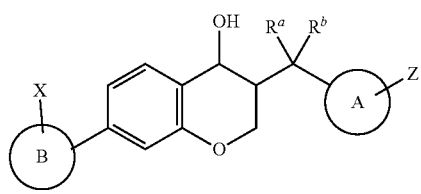

or a pharmaceutically acceptable salt thereof; wherein
A is selected from the group consisting of:
 (1) aryl, and
 (2) heteroaryl,
wherein aryl and heteroaryl are unsubstituted or substituted with 1-4 substituents independently selected from $C_{1-6}$alkyl and halogen;
B is selected from the group consisting of:
 (1) aryl, and
 (2) heteroaryl,
wherein aryl and heteroaryl are unsubstituted or substituted with 1-4 substituents independently selected from $C_{1-6}$alkyl and halogen;
X is selected from the group consisting of:
 (1) —C(O)NHSO$_2$CF$_3$,
 (2) —C(O)NHSO$_2$CH$_2$CF$_3$,
 (3) —C(O)NHSO$_2$CHF$_2$,
 (4) —C(O)NHSO$_2$C$_{1-6}$-alkyl,
 (5) —C(O)NHSO$_2$CH$_2$C$_{3-6}$cycloalkyl, and
 (6) —C(O)NHSO$_2$C$_{3-6}$cycloalkyl,
wherein alkyl and cycloalkyl are unsubstituted or substituted with 1-3 substituents independently selected from $C_{1-6}$alkyl;
Z is selected from the group consisting of:
 (1) hydrogen,
 (2) —C$_{1-6}$alkyl, and
 (3) phenyl,
wherein alkyl and phenyl are unsubstituted or substituted with 1-4 substituents independently selected from $C_{1-6}$alkyl;
$R^a$ is selected from the group consisting of:
 (1) hydrogen,
 (2) halogen, and
 (3) $C_{1-6}$alkyl; and
$R^b$ is selected from the group consisting of:
 (1) hydrogen,
 (2) halogen, and
 (3) $C_{1-6}$alkyl;
provided that when A is phenyl, B is phenyl and Z is hydrogen, then X is not —C(O)NHSO$_2$CF$_3$.

The invention has numerous embodiments, which are summarized below. The invention includes the compounds as shown, and also includes individual diastereoisomers, enantiomers, and epimers of the compounds, and mixtures of diastereoisomers and/or enantiomers thereof including racemic mixtures.

In one embodiment of the present invention, A is selected from the group consisting of: aryl and heteroaryl, wherein aryl and heteroaryl are unsubstituted or substituted with 1-4 substituents independently selected from $C_{1-6}$alkyl and halogen.

In another embodiment of the present invention, A is selected from the group consisting of: phenyl, pyridine, oxazole, thiazole, thiadiazole, and pyrazole, wherein phenyl, pyridine, oxazole, thiazole, thiadiazole, and pyrazole are unsubstituted or substituted with 1-4 substituents independently selected from $C_{1-6}$alkyl and halogen.

In another embodiment of the present invention, A is selected from the group consisting of: phenyl, pyridine, oxazole, thiazole, thiadiazole, and pyrazole, wherein phenyl, pyridine, oxazole, thiazole, thiadiazole, and pyrazole are unsubstituted or substituted with 1-4 substituents independently selected from $C_{1-6}$alkyl. In another embodiment of the present invention, A is selected from the group consisting of: phenyl, pyridine, oxazole, thiazole, thiadiazole, and pyrazole, wherein phenyl, pyridine, oxazole, thiazole, thiadiazole, and pyrazole are unsubstituted or substituted with 1-4 substituents independently selected from $CH_3$ and $CH_2CH_3$.

In another embodiment of the present invention, A is selected from the group consisting of: phenyl, pyridine, oxazole, thiazole, and pyrazole, wherein phenyl, pyridine, oxazole, thiazole, and pyrazole are unsubstituted or substituted with 1-4 substituents independently selected from $C_{1-6}$alkyl and halogen.

In another embodiment of the present invention, A is selected from the group consisting of: phenyl, pyridine, oxazole, thiazole, and pyrazole, wherein phenyl, pyridine, oxazole, thiazole, and pyrazole are unsubstituted or substituted with 1-4 substituents independently selected from $C_{1-6}$alkyl. In another embodiment of the present invention, A is selected from the group consisting of: phenyl, pyridine, oxazole, thiazole, and pyrazole, wherein phenyl, pyridine, oxazole, thiazole, and pyrazole are unsubstituted or substituted with 1-4 substituents independently selected from $CH_3$ and $CH_2CH_3$.

In another embodiment, A is aryl, wherein aryl is unsubstituted or substituted with 1-4 substituents independently selected from $C_{1-6}$alkyl and halogen. In another embodiment of the present invention, A is phenyl, wherein phenyl is unsubstituted or substituted with 1-4 substituents independently selected from $C_{1-6}$alkyl and halogen. In another embodiment of the present invention, A is phenyl, wherein phenyl is unsubstituted or substituted with 1-4 substituents independently selected from $C_{1-6}$alkyl. In another embodiment of the present invention, A is phenyl, wherein phenyl is unsubstituted or substituted with 1-4 substituents independently selected from $CH_3$ and $CH_2CH_3$.

In another embodiment of the present invention, A is heteroaryl, wherein heteroaryl are unsubstituted or substituted with 1-3 substituents independently selected from $C_{1-6}$alkyl and halogen. In another embodiment of the present invention, A is heteroaryl, wherein heteroaryl are unsubstituted or substituted with 1-3 substituents independently selected from $C_{1-6}$alkyl.

In another embodiment of the present invention, A is selected from the group consisting of: pyridine, oxazole, thiazole, thiadiazole, and pyrazole, wherein pyridine, oxazole, thiazole, thiadiazole, and pyrazole are unsubstituted or substituted with 1-3 substituents independently selected from $C_{1-6}$alkyl and halogen. In another embodiment of the present invention, A is selected from the group consisting of: pyridine, oxazole, thiazole, thiadiazole, and pyrazole, wherein pyridine, oxazole, thiazole, thiadiazole, and pyrazole are unsubstituted or substituted with 1-3 substituents independently selected from $C_{1-6}$alkyl. In another embodiment of the present invention, A is selected from the group consisting of: pyridine, oxazole, thiazole, thiadiazole, and pyrazole, wherein pyridine, oxazole, thiazole, thiadiazole, and pyrazole are unsubstituted or substituted with 1-3 substituents independently selected from $CH_3$ and $CH_2CH_3$.

In another embodiment of the present invention, A is selected from the group consisting of: pyridine, oxazole, thiazole, and pyrazole, wherein pyridine, oxazole, thiazole, and pyrazole are unsubstituted or substituted with 1-3 substituents independently selected from $C_{1-6}$alkyl and halogen. In another embodiment of the present invention, A is selected from the group consisting of: pyridine, oxazole, thiazole, and pyrazole, wherein pyridine, oxazole, thiazole, and pyrazole are unsubstituted or substituted with 1-3 substituents independently selected from $C_{1-6}$alkyl. In another embodiment of the present invention, A is selected from the group consisting of: pyridine, oxazole, thiazole, and pyrazole, wherein pyridine, oxazole, thiazole, and pyrazole are unsubstituted or substituted with 1-3 substituents independently selected from $CH_3$ and $CH_2CH_3$.

In another embodiment of the present invention, A is selected from the group consisting of: pyridine, thiazole, thiadiazole, and pyrazole, wherein pyridine, thiazole, thiadiazole, and pyrazole are unsubstituted or substituted with 1-3 substituents independently selected from $C_{1-6}$alkyl. In another embodiment of the present invention, A is selected from the group consisting of: pyridine, thiazole, thiadiazole, and pyrazole, wherein pyridine, thiazole, thiadiazole, and pyrazole are unsubstituted or substituted with 1-3 substituents independently selected from $C_{1-6}$alkyl. In another embodiment of the present invention, A is selected from the group consisting of: pyridine, thiazole, thiadiazole, and pyrazole, wherein pyridine, thiazole, thiadiazole, and pyrazole are unsubstituted or substituted with 1-3 substituents independently selected from $CH_3$ and $CH_2CH_3$.

In another embodiment of the present invention, A is selected from the group consisting of: pyridine, thiazole, and pyrazole, wherein pyridine, thiazole, and pyrazole are unsubstituted or substituted with 1-3 substituents independently selected from $C_{1-6}$alkyl and halogen. In another embodiment of the present invention, A is selected from the group consisting of: pyridine, thiazole, and pyrazole, wherein pyridine, thiazole, and pyrazole are unsubstituted or substituted with 1-3 substituents independently selected from $C_{1-6}$alkyl. In another embodiment of the present invention, A is selected from the group consisting of: pyridine, thiazole, and pyrazole, wherein pyridine, thiazole, and pyrazole are unsubstituted or substituted with 1-3 substituents independently selected from $CH_3$ and $CH_2CH_3$.

In another embodiment of the present invention, A is heteroaryl, wherein heteroaryl are unsubstituted or substituted with 1-3 substituents independently selected from $C_{1-6}$alkyl and halogen. In another embodiment of the present invention, A is heteroaryl, wherein heteroaryl are unsubstituted or substituted with 1-3 substituents independently selected from $C_{1-6}$alkyl. In another embodiment of the present invention, A is oxazole, wherein oxazole is unsubstituted or substituted with 1-3 substituents independently selected from $C_{1-6}$alkyl and halogen. In another embodiment of the present invention, A is oxazole, wherein oxazole is unsubstituted or substituted with 1-3 substituents independently selected from $C_{1-6}$alkyl. In another embodiment of the present invention, A is oxazole, wherein oxazole is unsubstituted or substituted with 1-3 substituents independently selected from $CH_3$ and $CH_2CH_3$. In another embodiment of the present invention, A is oxazole.

In another embodiment of the present invention, A is heteroaryl, wherein heteroaryl are unsubstituted or substituted with 1-3 substituents independently selected from $C_{1-6}$alkyl and halogen. In another embodiment of the present invention, A is heteroaryl, wherein heteroaryl is unsubstituted or substituted with 1-3 substituents independently selected from $C_{1-6}$alkyl. In another embodiment of the present invention, A is pyridine, wherein pyridine is unsubstituted or substituted with 1-3 substituents independently selected from $C_{1-6}$alkyl and halogen. In another embodiment of the present invention, A is pyridine, wherein pyridine is unsubstituted or substituted with 1-4 substituents independently selected from $C_{1-6}$alkyl. In another embodiment of the present invention, A is pyridine, wherein pyridine is unsubstituted or substituted with one substituent selected from $C_{1-6}$alkyl. In another embodiment of the present invention, A is pyridine, wherein pyridine is unsubstituted or substituted with 1-3 substituents independently selected from $CH_3$ and $CH_2CH_3$. In another embodiment of the present invention, A is pyridine.

In another embodiment, A is selected from the group consisting of: pyrazole, thiazole, and benzothiophene, wherein A is unsubstituted or substituted with 1-3 substituents independently selected from $C_{1-6}$-alkyl and halogen. In another embodiment, A is selected from the group consisting of: pyrazole, thiazole, and benzothiophene, wherein A is unsubstituted or substituted with 1-3 substituents independently selected from $CH_3$ and F. In another embodiment, A is selected from the group consisting of: pyrazole, thiazole, and benzothiophene.

In another embodiment, A is selected from the group consisting of: thiazole, and benzothiophene, wherein A is unsubstituted or substituted with 1-3 substituents independently selected from $C_{1-6}$alkyl and halogen. In another embodiment, A is selected from the group consisting of: thiazole, and benzothiophene, wherein A is unsubstituted or substituted with 1-3 substituents independently selected from $CH_3$ and F. In another embodiment, A is selected from the group consisting of: thiazole, and benzothiophene.

In another embodiment of the present invention, B is selected from the group consisting of: aryl, and heteroaryl, wherein aryl and heteroaryl are unsubstituted or substituted with 1-4 substituents independently selected from $C_{1-6}$alkyl and halogen.

In another embodiment of the present invention, B is heteroaryl, wherein heteroaryl is unsubstituted or substituted with 1-3 substituents independently selected from $C_{1-6}$alkyl and halogen.

In another embodiment of the present invention, B is aryl, wherein aryl is unsubstituted or substituted with 1-4 substituents independently selected from $C_{1-6}$alkyl and halogen. In another embodiment of the present invention, B is phenyl, wherein phenyl is unsubstituted or substituted with 1-4 substituents independently selected from $C_{1-6}$alkyl and halogen.

In another embodiment of the present invention, B is phenyl, wherein phenyl is unsubstituted or substituted with 1-4 substituents independently selected from $C_{1-6}$alkyl. In another embodiment of the present invention, B is phenyl, wherein phenyl is unsubstituted or substituted with 1-4 substituents independently selected from halogen. In another embodiment of the present invention, B is phenyl, wherein phenyl is unsubstituted or substituted with 1-4 substituents independently selected from F. In another embodiment of the present invention, B is phenyl, wherein phenyl is unsubstituted or substituted with one substituents independently selected from halogen. In another embodiment of the present invention, B is phenyl, wherein phenyl is unsubstituted or substituted with one F substituent.

In another embodiment of the present invention, B is phenyl.

In another embodiment of the present invention, X is selected from the group consisting of: —C(O)NHSO$_2$CF$_3$, —C(O)NHSO$_2$CH$_2$CF$_3$, —C(O)NHSO$_2$CHF$_2$, —C(O)NHSO$_2$C$_{1-6}$alkyl, —C(O)NHSO$_2$CH$_2$C$_{3-6}$cycloalkyl, and —C(O)NHSO$_2$C$_{3-6}$cycloalkyl, wherein alkyl and cycloalkyl are unsubstituted or substituted with 1-3 substituents independently selected from $C_{1-6}$alkyl.

In another embodiment of the present invention, X is selected from the group consisting of: —C(O)NHSO$_2$CH$_2$CF$_3$, —C(O)NHSO$_2$CHF$_2$, —C(O)NHSO$_2$C$_{1-6}$alkyl, —C(O)NHSO$_2$CH$_2$C$_{3-6}$cycloalkyl, and —C(O)NHSO$_2$C$_{3-6}$cycloalkyl, wherein alkyl and cycloalkyl are unsubstituted or substituted with 1-3 substituents independently selected from $C_{1-6}$alkyl.

In another embodiment of the present invention, X is selected from the group consisting of: —C(O)NHSO$_2$CF$_3$, —C(O)NHSO$_2$CH$_2$C$_{3-6}$cycloalkyl, and —C(O)NHSO$_2$C$_{3-6}$cycloalkyl, wherein alkyl and cycloalkyl are unsubstituted or substituted with 1-3 substituents independently selected from $C_{1-6}$alkyl, provided that when A is aryl wherein aryl is phenyl, B is aryl wherein aryl is phenyl, and Z is hydrogen, then X is not —C(O)NHSO$_2$CF$_3$.

In another embodiment of the present invention, X is selected from the group consisting of: —C(O)NHSO$_2$CF$_3$, —C(O)NHSO$_2$CH$_2$C$_{3-6}$cycloalkyl, and —C(O)NHSO$_2$C$_{3-6}$cycloalkyl, wherein alkyl and cycloalkyl are unsubstituted or substituted with 1-3 substituents independently selected from $C_{1-6}$alkyl, provided that when A is phenyl, B is phenyl and Z is hydrogen, then X is not —C(O)NHSO$_2$CF$_3$.

In another embodiment of the present invention, X is selected from the group consisting of: —C(O)NHSO$_2$CF$_3$, —C(O)NHSO$_2$CH$_2$C$_{3-6}$cycloalkyl, and —C(O)NHSO$_2$C$_{3-6}$cycloalkyl, wherein alkyl and cycloalkyl are unsubstituted or substituted with 1-3 substituents independently selected from $C_{1-6}$alkyl.

In another embodiment of the present invention, X is selected from the group consisting of: —C(O)NHSO$_2$CH$_2$C$_{3-6}$cycloalkyl, and —C(O)NHSO$_2$C$_{3-6}$cycloalkyl, wherein cycloalkyl is unsubstituted or substituted with 1-3 substituents independently selected from $C_{1-6}$alkyl.

In another embodiment of the present invention, X is selected from the group consisting of: —C(O)NHSO$_2$CF$_3$, —C(O)NHSO$_2$CH$_2$CF$_3$, —C(O)NHSO$_2$CHF$_2$, —C(O)NHSO$_2$CH$_3$, —C(O)NHSO$_2$C(CH$_3$)$_3$, —C(O)NHSO$_2$CH$_2$C(CH$_3$)$_3$, —C(O)NHSO$_2$CH$_2$CH(CH$_3$)$_2$, —C(O)NHSO$_2$CH$_2$-cyclopropyl, —C(O)NHSO$_2$-cyclopropyl, and —C(O)NHSO$_2$-cyclopentyl, wherein alkyl and cycloalkyl are unsubstituted or substituted with 1-3 substituents independently selected from $CH_3$.

In another embodiment, X is selected from the group consisting of: —C(O)NHSO$_2$CF$_3$, —C(O)NHSO$_2$C$_{1-6}$alkyl, —C(O)NHSO$_2$CH$_2$C$_{3-6}$cycloalkyl and —C(O)NHSO$_2$C$_{3-6}$cycloalkyl, wherein alkyl and cycloalkyl are unsubstituted or substituted with 1-3 substituents independently selected from $C_{1-6}$alkyl.

In another embodiment, X is selected from the group consisting of: —C(O)NHSO$_2$CF$_3$, —C(O)NHSO$_2$CH$_3$, —C(O)NHSO$_2$C(CH$_3$)$_3$, —C(O)NHSO$_2$CH$_2$C(CH$_3$)$_3$, —C(O)NHSO$_2$CH$_2$CH(CH$_3$)$_2$, —C(O)NHSO$_2$CH$_2$-cyclopropyl, —C(O)NHSO$_2$-cyclopropyl, and —C(O)NHSO$_2$-cyclopentyl, wherein alkyl and cycloalkyl are unsubstituted or substituted with 1-3 substituents independently selected from C$_{1-6}$alkyl.

In another embodiment, X is selected from the group consisting of: —C(O)NHSO$_2$CF$_3$, —C(O)NHSO$_2$CH$_3$, —C(O)NHSO$_2$C(CH$_3$)$_3$, —C(O)NHSO$_2$CH$_2$C(CH$_3$)$_3$, —C(O)NHSO$_2$CH$_2$CH(CH$_3$)$_2$, —C(O)NHSO$_2$CH$_2$-cyclopropyl, —C(O)NHSO$_2$-cyclopropyl, and —C(O)NHSO$_2$-cyclopentyl, wherein alkyl and cycloalkyl are unsubstituted or substituted with 1-3 CH$_3$ substituents.

In another embodiment of the present invention, X is selected from the group consisting of: —C(O)NHSO$_2$CH$_2$CF$_3$, —C(O)NHSO$_2$CHF$_2$, —C(O)NHSO$_2$C$_{1-6}$alkyl, —C(O)NHSO$_2$CH$_2$C$_{3-6}$cycloalkyl, and —C(O)NHSO$_2$C$_{3-6}$cycloalkyl, wherein alkyl and cycloalkyl are unsubstituted or substituted with 1-3 substituents independently selected from C$_{1-6}$alkyl.

In another embodiment of the present invention, X is selected from the group consisting of: —C(O)NHSO$_2$CHF$_2$, —C(O)NHSO$_2$C$_{1-6}$alkyl, —C(O)NHSO$_2$CH$_2$C$_{3-6}$cycloalkyl and —C(O)NHSO$_2$C$_{3-6}$cycloalkyl, wherein alkyl and cycloalkyl are unsubstituted or substituted with 1-3 substituents independently selected from C$_{1-6}$alkyl.

In another embodiment of the present invention, X is selected from the group consisting of: —C(O)NHSO$_2$C$_{1-6}$alkyl, —C(O)NHSO$_2$CH$_2$C$_{3-6}$cycloalkyl and —C(O)NHSO$_2$C$_{3-6}$cycloalkyl, wherein alkyl and cycloalkyl are unsubstituted or substituted with 1-3 substituents independently selected from C$_{1-6}$alkyl.

In another embodiment of the present invention, X is selected from the group consisting of: —C(O)NHSO$_2$CH$_2$CF$_3$, —C(O)NHSO$_2$CHF$_2$, —C(O)NHSO$_2$CH$_3$, —C(O)NHSO$_2$C(CH$_3$)$_3$, —C(O)NHSO$_2$CH$_2$C(CH$_3$)$_3$, —C(O)NHSO$_2$CH$_2$CH(CH$_3$)$_2$, —C(O)NHSO$_2$CH$_2$-cyclopropyl, —C(O)NHSO$_2$-cyclopropyl, and —C(O)NHSO$_2$-cyclopentyl, wherein alkyl and cycloalkyl are unsubstituted or substituted with 1-3 CH$_3$ substituents.

In another embodiment, X is selected from the group consisting of: —C(O)NHSO$_2$C$_{1-6}$alkyl, —C(O)NHSO$_2$CH$_2$C$_{3-6}$cycloalkyl and —C(O)NHSO$_2$C$_{3-6}$cycloalkyl, wherein alkyl and cycloalkyl are unsubstituted or substituted with 1-3 substituents independently selected from C$_{1-6}$alkyl.

In another embodiment, X is selected from the group consisting of: —C(O)NHSO$_2$CH$_3$, —C(O)NHSO$_2$C(CH$_3$)$_3$, —C(O)NHSO$_2$CH$_2$C(CH$_3$)$_3$, —C(O)NHSO$_2$CH$_2$CH(CH$_3$)$_2$, —C(O)NHSO$_2$CH$_2$-cyclopropyl, —C(O)NHSO$_2$-cyclopropyl and —C(O)NHSO$_2$-cyclopentyl, wherein alkyl and cycloalkyl are unsubstituted or substituted with 1-3 substituents independently selected from C$_{1-6}$alkyl.

In another embodiment, X is selected from the group consisting of: —C(O)NHSO$_2$CH$_3$, —C(O)NHSO$_2$C(CH$_3$)$_3$, —C(O)NHSO$_2$CH$_2$C(CH$_3$)$_3$, —C(O)NHSO$_2$CH$_2$CH(CH$_3$)$_2$, —C(O)NHSO$_2$CH$_2$-cyclopropyl, —C(O)NHSO$_2$-cyclopropyl, and —C(O)NHSO$_2$-cyclopentyl, wherein alkyl and cycloalkyl are unsubstituted or substituted with 1-3 CH$_3$ substituents.

In another embodiment of the present invention, X is selected from the group consisting of: —C(O)NHSO$_2$CF$_3$, —C(O)NHSO$_2$C$_{1-6}$alkyl, —C(O)NHSO$_2$CH$_2$C$_{3-6}$cycloalkyl and —C(O)NHSO$_2$C$_{3-6}$cycloalkyl, wherein alkyl and cycloalkyl are unsubstituted or substituted with 1-3 substituents independently selected from C$_{1-6}$alkyl.

In another embodiment of the present invention, X is selected from the group consisting of: —C(O)NHSO$_2$CF$_3$, —C(O)NHSO$_2$CH$_3$, —C(O)NHSO$_2$C(CH$_3$)$_3$, —C(O)NHSO$_2$CH$_2$C(CH$_3$)$_3$, —C(O)NHSO$_2$CH$_2$CH(CH$_3$)$_2$, —C(O)NHSO$_2$CH$_2$-cyclopropyl, —C(O)NHSO$_2$-cyclopropyl, and —C(O)NHSO$_2$-cyclopentyl, wherein alkyl and cycloalkyl are unsubstituted or substituted with 1-3 CH$_3$ substituents.

In another embodiment of the present invention, X is selected from the group consisting of: —C(O)NHSO$_2$C$_{1-6}$alkyl, —C(O)NHSO$_2$CH$_2$C$_{3-6}$cycloalkyl, and —C(O)NHSO$_2$C$_{3-6}$cycloalkyl, wherein alkyl and cycloalkyl are unsubstituted or substituted with 1-3 substituents independently selected from C$_{1-6}$alkyl.

In another embodiment of the present invention, X is selected from the group consisting of: —C(O)NHSO$_2$CH$_3$, —C(O)NHSO$_2$C(CH$_3$)$_3$, —C(O)NHSO$_2$CH$_2$C(CH$_3$)$_3$, —C(O)NHSO$_2$CH$_2$CH(CH$_3$)$_2$, —C(O)NHSO$_2$CH$_2$-cyclopropyl, —C(O)NHSO$_2$-cyclopropyl and —C(O)NHSO$_2$-cyclopentyl, wherein alkyl and cycloalkyl are unsubstituted or substituted with 1-3 CH$_3$ substituents.

In another embodiment of the present invention, X is selected from the group consisting of: —C(O)NHSO$_2$C$_{1-6}$alkyl and —C(O)NHSO$_2$C$_{3-6}$cycloalkyl, wherein alkyl and cycloalkyl are unsubstituted or substituted with 1-3 substituents independently selected from C$_{1-6}$alkyl.

In another embodiment of the present invention, X is selected from the group consisting of: —C(O)NHSO$_2$C(CH$_3$)$_3$ and —C(O)NHSO$_2$-cyclopropyl, wherein alkyl and cycloalkyl are unsubstituted or substituted with 1-3 CH$_3$ substituents.

In another embodiment of the present invention, X is selected from the group consisting of: —C(O)NHSO$_2$C$_{1-6}$alkyl and —C(O)NHSO$_2$C$_{3-6}$cycloalkyl, wherein alkyl and cycloalkyl are unsubstituted or substituted with 1-3 substituents independently selected from C$_{1-6}$alkyl. In another embodiment of the present invention, X is selected from the group consisting of: —C(O)NHSO$_2$C(CH$_3$)$_3$, and —C(O)NHSO$_2$-cyclopropyl, wherein alkyl and cycloalkyl are unsubstituted or substituted with 1-3 CH$_3$ substituents.

In another embodiment of the present invention, X is selected from the group consisting of: —C(O)NHSO$_2$CH$_2$CF$_3$, —C(O)NHSO$_2$C$_{2-4}$alkyl, and —C(O)NHSO$_2$CHF$_2$.

In another embodiment of the present invention, X is selected from the group consisting of: —C(O)NHSO$_2$CH$_2$CF$_3$, and —C(O)NHSO$_2$C$_{2-4}$alkyl.

In another embodiment of the present invention, Z is selected from the group consisting of: hydrogen, —C$_{1-6}$alkyl, and phenyl, wherein alkyl and phenyl are unsubstituted or substituted with 1-4 substituents independently selected from C$_{1-6}$alkyl. In another embodiment of the present invention, Z is selected from the group consisting of: hydrogen, and —C$_{1-6}$alkyl, wherein alkyl is unsubstituted or substituted with 1-4 substituents independently selected from C$_{1-6}$alkyl. In another embodiment of the present invention, Z is selected from the group consisting of: —C$_{1-6}$alkyl, and phenyl, wherein alkyl and phenyl are unsubstituted or substituted with 1-4 substituents independently selected from C$_{1-6}$alkyl. In another embodiment of the present invention, Z is —C$_{1-6}$alkyl, wherein alkyl is unsubstituted or substituted with 1-4 substituents independently selected from C$_{1-6}$alkyl. In another embodiment of the present invention, Z is —C$_{1-6}$alkyl.

In another embodiment of the present invention, Z is selected from the group consisting of: hydrogen, and phenyl, wherein phenyl is unsubstituted or substituted with 1-4 substituents independently selected from C$_{1-6}$alkyl. In another embodiment of the present invention, Z is selected from the group consisting of: hydrogen, and phenyl, wherein phenyl is unsubstituted or substituted with 1-4 CH$_3$ substituents.

In another embodiment of the present invention, Z is phenyl, wherein phenyl is unsubstituted or substituted with 1-4 substituents independently selected from C$_{1-6}$ alkyl. In another embodiment of the present invention, Z is phenyl, wherein phenyl is unsubstituted or substituted with 1-4 CH$_3$ substituents. In another embodiment of the present invention, Z is phenyl.

In another embodiment of the present invention, Z is hydrogen.

In another embodiment of the present invention, R$^a$ is selected from the group consisting of: hydrogen, and C$_{1-6}$ alkyl. In another embodiment of the present invention, R$^a$ is selected from the group consisting of: hydrogen, and CH$_3$. In another embodiment of the present invention, R$^a$ is hydrogen. In another embodiment of the present invention, R$^a$ is CH$_3$.

In another embodiment of the present invention, R$^b$ is selected from the group consisting of: hydrogen, and C$_{1-6}$alkyl. In another embodiment of the present invention, R$^b$ is selected from the group consisting of: hydrogen, and CH$_3$. In another embodiment of the present invention, R$^b$ is hydrogen. In another embodiment of the present invention, R$^b$ is CH$_3$.

In another embodiment of the present invention, the invention relates to compounds of structural formula Ia:

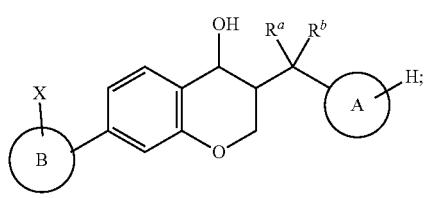

Ia or a pharmaceutically acceptable salt thereof.

In another embodiment of the present invention, the invention relates to compounds of structural formula Ib:

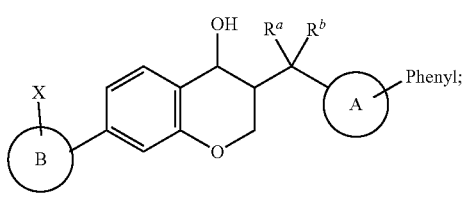

Ib or a pharmaceutically acceptable salt thereof.

In another embodiment of the present invention, the invention relates to compounds of structural formula Ic:

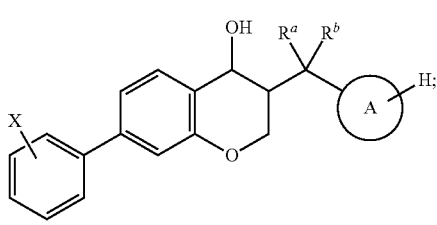

Ic or a pharmaceutically acceptable salt thereof.

In another embodiment of the present invention, the invention relates to compounds of structural formula Id:

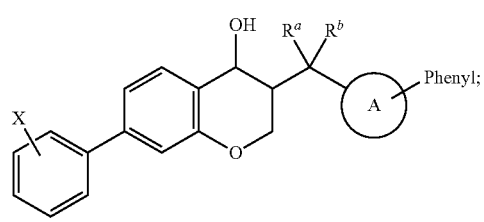

Id or a pharmaceutically acceptable salt thereof.

In another embodiment of the present invention, the invention relates to compounds of structural formula Ie:

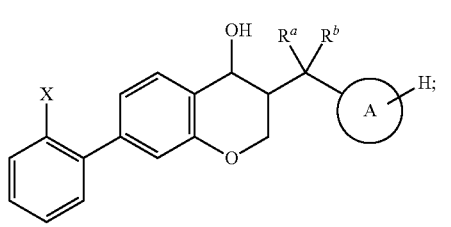

Ie or a pharmaceutically acceptable salt thereof.

In another embodiment of the present invention, the invention relates to compounds of structural formula If:

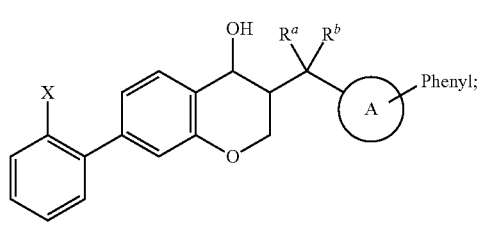

If or a pharmaceutically acceptable salt thereof.

In another embodiment of the present invention, the invention relates to compounds of structural formula Ig:

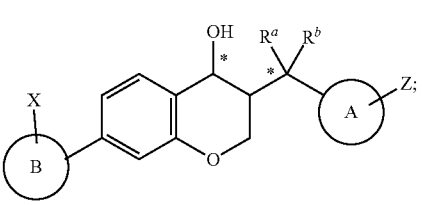

Ig wherein the "*" bonds are trans bonds, or a pharmaceutically acceptable salt thereof. In another embodiment of the present invention, the invention relates to compounds of structural formula Ig wherein the * bonds are cis bonds, or a pharmaceutically acceptable salt thereof.

In another embodiment of the present invention, the invention relates to compounds of structural formula Ih:

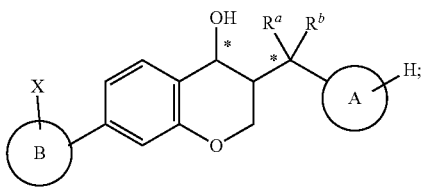

Ih wherein the "*" bonds are trans bonds, or a pharmaceutically acceptable salt thereof. In another embodiment of the present invention, the invention relates to compounds of structural formula Ih wherein the * bonds are cis bonds, or a pharmaceutically acceptable salt thereof.

In another embodiment of the present invention, the invention relates to compounds of structural formula Ii:

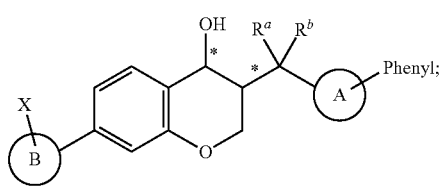

Ii wherein the "*" bonds are trans bonds, or a pharmaceutically acceptable salt thereof. In another embodiment of the present invention, the invention relates to compounds of structural formula Ii wherein the * bonds are cis bonds, or a pharmaceutically acceptable salt thereof.

In another embodiment of the present invention, the invention relates to compounds of structural formula Ij:

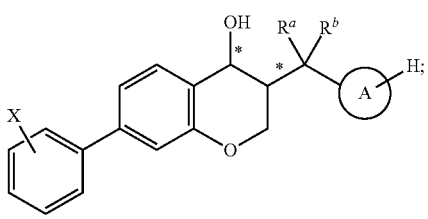

Ij wherein the "*" bonds are trans bonds, or a pharmaceutically acceptable salt thereof. In another embodiment of the present invention, the invention relates to compounds of structural formula Ij wherein the * bonds are cis bonds, or a pharmaceutically acceptable salt thereof.

In another embodiment of the present invention, the invention relates to compounds of structural formula Ik:

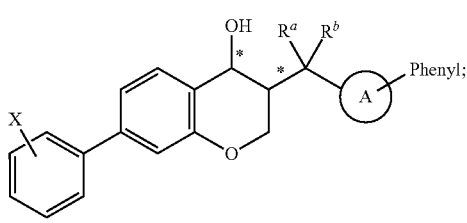

Ik wherein the "*" bonds are trans bonds, or a pharmaceutically acceptable salt thereof. In another embodiment of the present invention, the invention relates to compounds of structural formula Ik wherein the * bonds are cis bonds, or a pharmaceutically acceptable salt thereof.

In another embodiment of the present invention, the invention relates to compounds of structural formula Il:

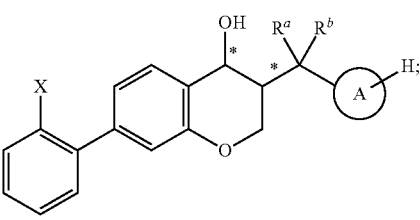

Il wherein the "*" bonds are trans bonds, or a pharmaceutically acceptable salt thereof. In another embodiment of the present invention, the invention relates to compounds of structural formula Il wherein the * bonds are cis bonds, or a pharmaceutically acceptable salt thereof.

In another embodiment of the present invention, the invention relates to compounds of structural formula Im:

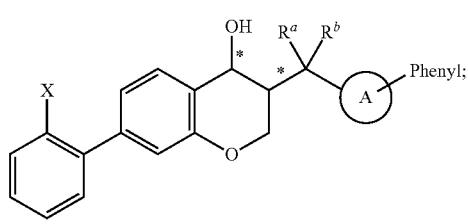

Im wherein the "*" bonds are trans bonds, or a pharmaceutically acceptable salt thereof. In another embodiment of the present invention, the invention relates to compounds of structural formula Im wherein the * bonds are cis bonds, or a pharmaceutically acceptable salt thereof.

The term "trans bonds" refers to bonds with the following stereochemistry:

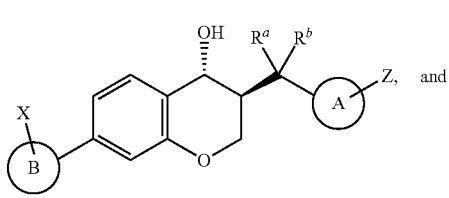

In

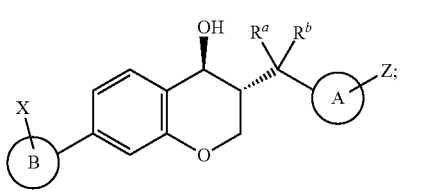

Io and pharmaceutically acceptable salts thereof.

In one embodiment of the present invention, the compounds of structural formula I have the following trans bond configuration:

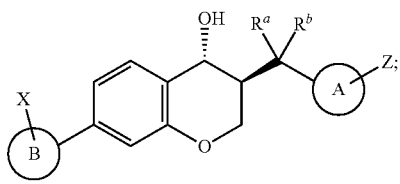

In or a pharmaceutically acceptable salt thereof.

In another embodiment of the present invention, the compound of structural formula I has the following trans bond configuration:

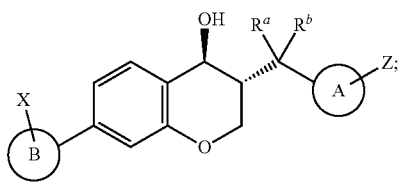

Io or a pharmaceutically acceptable salt thereof.

The term "cis bonds" refers to bonds with the following stereochemistry:

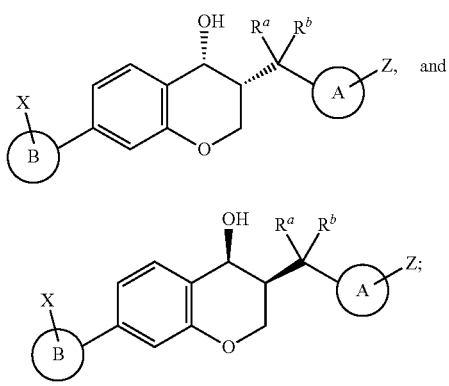

Ip

Iq and pharmaceutically acceptable salts thereof.

In one embodiment of the present invention, the compounds of structural formula I have the following cis bond configuration:

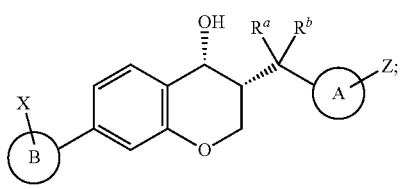

Ip or a pharmaceutically acceptable salt thereof.

In another embodiment of the present invention, the compound of structural formula I has the following cis bond configuration:

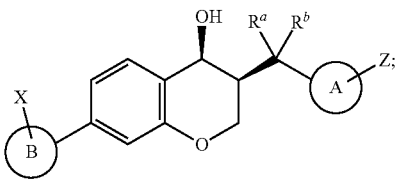

Iq or a pharmaceutically acceptable salt thereof.

The compound of structural formula I includes the compounds of structural formulas Ia, Ib, Ic, Id, Ie, If, Ig, Ih, Ii, Ij, Ik, Il, Im, In, Io, Ip, and Iq, and pharmaceutically acceptable salts, hydrates and solvates thereof.

Another embodiment of the present invention relates to compounds of structural formula I:

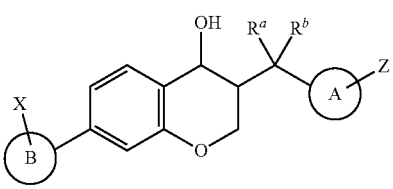

I wherein
A is aryl, wherein aryl is unsubstituted or substituted with 1-4 substituents independently selected from $C_{1-6}$alkyl and halogen;
B is aryl, wherein aryl is unsubstituted or substituted with 1-4 substituents independently selected from $C_{1-6}$alkyl and halogen;
X is selected from the group consisting of:
 (1) —C(O)NHSO$_2$CF$_3$,
 (2) —C(O)NHSO$_2$CH$_2$C$_{3-6}$cycloalkyl, and
 (3) —C(O)NHSO$_2$C$_{3-6}$cycloalkyl,
wherein alkyl and cycloalkyl are unsubstituted or substituted with 1-3 substituents independently selected from $C_{1-6}$alkyl;
Z is selected from the group consisting of:
 (1) hydrogen, and
 (2) phenyl,
wherein phenyl is unsubstituted or substituted with 1-4 substituents independently selected from $C_{1-6}$-alkyl; and
$R^a$ and $R^b$ are selected from the group consisting of: hydrogen, and $C_{1-6}$alkyl;
provided that when A is phenyl, B is phenyl and Z is hydrogen, then X is not —C(O)NHSO$_2$CF$_3$; or a pharmaceutically acceptable salt thereof.

Another embodiment of the present invention relates to compounds of structural formula I:

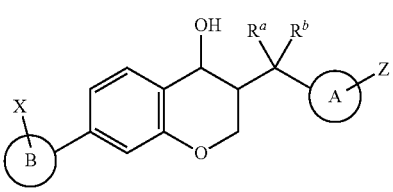

I wherein
A is phenyl, wherein phenyl is unsubstituted or substituted with 1-4 substituents independently selected from $C_{1-6}$alkyl and halogen;

B is phenyl, wherein phenyl is unsubstituted or substituted with 1-4 substituents independently selected from $C_{1-6}$alkyl and halogen;

X is selected from the group consisting of:
(1) —C(O)NHSO$_2$CF$_3$,
(2) —C(O)NHSO$_2$CH$_2$C$_{3-6}$cycloalkyl, and
(3) —C(O)NHSO$_2$C$_{3-6}$cycloalkyl, wherein alkyl and cycloalkyl are unsubstituted or substituted with 1-3 substituents independently selected from $C_{1-6}$alkyl;

Z is selected from the group consisting of:
(1) hydrogen,
(2) —C$_{1-6}$alkyl, and
(3) phenyl, wherein alkyl and phenyl are unsubstituted or substituted with 1-4 substituents independently selected from $C_{1-6}$alkyl; and $R^a$ and $R^b$ are selected from the group consisting of: hydrogen, and $C_{1-6}$alkyl;

provided that when A is phenyl, B is phenyl and Z is hydrogen, then X is not —C(O)NHSO$_2$CF$_3$;

or a pharmaceutically acceptable salt thereof.

Another embodiment of the present invention relates to compounds of structural formula I:

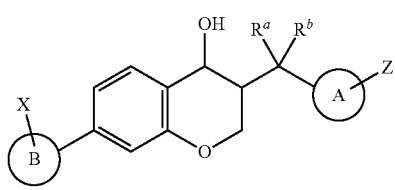

wherein

A is heteroaryl, wherein heteroaryl is unsubstituted or substituted with 1-3 substituents independently selected from $C_{1-6}$alkyl and halogen;

B is aryl, wherein aryl is unsubstituted or substituted with 1-4 substituents independently selected from $C_{1-6}$alkyl and halogen;

X is selected from the group consisting of:
(1) —C(O)NHSO$_2$CF$_3$,
(2) —C(O)NHSO$_2$C$_{1-6}$-alkyl,
(3) —C(O)NHSO$_2$CH$_2$C$_{3-6}$cycloalkyl, and
(4) —C(O)NHSO$_2$C$_{3-6}$cycloalkyl, wherein alkyl and cycloalkyl are unsubstituted or substituted with 1-3 substituents independently selected from $C_{1-6}$alkyl;

Z is selected from the group consisting of:
(1) hydrogen,
(2) —C$_{1-6}$ alkyl, and
(3) phenyl, wherein alkyl and phenyl are unsubstituted or substituted with 1-4 substituents independently selected from $C_{1-6}$alkyl; and $R^a$ and $R^b$ are selected from the group consisting of: hydrogen, and $C_{1-6}$alkyl;

or a pharmaceutically acceptable salt thereof.

Another embodiment of the present invention relates to compounds of structural Formula I:

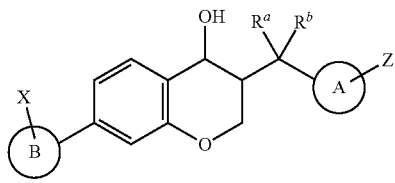

wherein

A is selected from the group consisting of: pyridine, oxazole, thiazole, thiadiazole, and pyrazole, wherein pyridine, oxazole, thiazole, thiadiazole, and pyrazole are unsubstituted or substituted with 1-3 substituents independently selected from $C_{1-6}$alkyl;

B is phenyl, wherein phenyl is unsubstituted or substituted with 1-4 substituents independently selected from halogen;

X is selected from the group consisting of:
(1) —C(O)NHSO$_2$CF$_3$,
(2) —C(O)NHSO$_2$C$_{1-6}$alkyl,
(3) —C(O)NHSO$_2$CH$_2$C$_{3-6}$cycloalkyl, and
(4) —C(O)NHSO$_2$C$_{3-6}$cycloalkyl, wherein alkyl and cycloalkyl are unsubstituted or substituted with 1-3 substituents independently selected from $C_{1-6}$alkyl;

Z is selected from the group consisting of:
(1) hydrogen,
(2) —C$_{1-6}$alkyl, and
(3) phenyl, wherein alkyl and phenyl are unsubstituted or substituted with 1-4 substituents independently selected from $C_{1-6}$alkyl; and $R^a$ and $R^b$ are hydrogen;

or a pharmaceutically acceptable salt thereof.

Another embodiment of the present invention relates to compounds of structural Formula I:

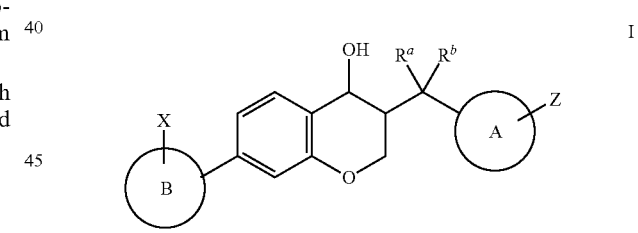

wherein

A is selected from the group consisting of: pyridine, oxazole, thiazole, thiadiazole, and pyrazole, wherein pyridine, oxazole, thiazole, thiadiazole, and pyrazole are unsubstituted or substituted with 1-3 substituents independently selected from $C_{1-6}$alkyl;

B is phenyl, wherein phenyl is unsubstituted or substituted with 1-4 substituents independently selected from halogen;

X is selected from the group consisting of:
(1) —C(O)NHSO$_2$CF$_3$,
(2) —C(O)NHSO$_2$C$_{1-6}$alkyl,
(3) —C(O)NHSO$_2$CH$_2$C$_{3-6}$cycloalkyl, and
(4) —C(O)NHSO$_2$C$_{3-6}$cycloalkyl, wherein alkyl and cycloalkyl are unsubstituted or substituted with 1-3 substituents independently selected from $C_{1-6}$alkyl;

Z is hydrogen; and $R^a$ and $R^b$ are hydrogen;

or a pharmaceutically acceptable salt thereof.

Another embodiment of the present invention relates to compounds of structural Formula I:

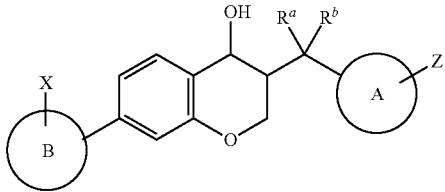

wherein
A is oxazole, wherein oxazole is unsubstituted or substituted with 1-3 substituents independently selected from $C_{1-6}$alkyl and halogen;
B is phenyl;
X is selected from the group consisting of:
(1) —C(O)NHSO$_2$C$_{1-6}$alkyl, and
(2) —C(O)NHSO$_2$C$_{3-6}$cycloalkyl,
wherein alkyl and cycloalkyl are unsubstituted or substituted with 1-3 substituents independently selected from $C_{1-6}$alkyl;
Z is phenyl, wherein phenyl is unsubstituted or substituted with 1-4 substituents independently selected from $C_{1-6}$alkyl; and
$R^a$ and $R^b$ are hydrogen;
or a pharmaceutically acceptable salt thereof.

Illustrative, but non-limiting, examples of the compounds of the present invention that are useful as antagonists of the leukotriene B$_4$ receptor 1 (BLT1) are the following compounds:

(1) 4-Fluoro-2-((3S,4R)-4-hydroxy-3-(pyridin-2-ylmethyl)chroman-7-yl)-N-((trifluoro-methyl)sulfonyl)benzamide;
(2) 4-Fluoro-2-((3R,4S)-4-hydroxy-3-(pyridin-2-ylmethyl)chroman-7-yl)-N-((trifluoro-methyl)sulfonyl)benzamide;
(3) 4-Fluoro-2-((3S,4R)-4-hydroxy-3-(pyridin-2-ylmethyl)chroman-7-yl)-N-(methyl-sulfonyl)benzamide;
(4) 4-Fluoro-2-((3R,4S)-4-hydroxy-3-(pyridin-2-ylmethyl)chroman-7-yl)-N-(methyl-sulfonyl)benzamide;
(5) N-(Cyclopropylsulfonyl)-2-((3S,4R)-4-hydroxy-3-(pyridin-2-ylmethyl)chroman-7-yl)benzamide;
(6) N-(Cyclopropylsulfonyl)-2-((3R,4S)-4-hydroxy-3-(pyridin-2-ylmethyl)chroman-7-yl)benzamide;
(7) 2-((3S,4R)-4-Hydroxy-3-(pyridin-2-ylmethyl)chroman-7-yl)-N-((1-methylcyclo-propyl)sulfonyl)benzamide;
(8) 2-((3R,4S)-4-Hydroxy-3-(pyridin-2-ylmethyl)chroman-7-yl)-N-((1-methylcyclo-propyl)sulfonyl)benzamide;
(9) 4-Fluoro-2-((3S,4R)-4-hydroxy-3-(pyridin-2-ylmethyl)chroman-7-yl)-N-((1-methyl-cyclopropyl)sulfonyl)benzamide;
(10) 4-Fluoro-2-((3R,4S)-4-hydroxy-3-(pyridin-2-ylmethyl)chroman-7-yl)-N-((1-methyl-cyclopropyl)sulfonyl)benzamide;
(11) N-(tert-Butylsulfonyl)-2-((3S,4R)-4-hydroxy-3-(pyridin-2-ylmethyl)chroman-7-yl)benzamide;
(12) N-(tert-Butylsulfonyl)-2-((3R,4S)-4-hydroxy-3-(pyridin-2-ylmethyl)chroman-7-yl)benzamide;
(13) N-(tert-Butylsulfonyl)-4-fluoro-2-((3S,4R)-4-hydroxy-3-(pyridin-2-ylmethyl)chroman-7-yl)benzamide;
(14) N-(tert-Butylsulfonyl)-4-fluoro-2-((3R,4S)-4-hydroxy-3-(pyridin-2-ylmethyl)chroman-7-yl)benzamide;
(15) N-(Cyclopropylsulfonyl)-4-fluoro-2-((3S,4R)-4-hydroxy-3-(pyridin-2-ylmethyl)chroman-7-yl)benzamide;
(16) N-(Cyclopropylsulfonyl)-4-fluoro-2-((3R,4S)-4-hydroxy-3-(pyridin-2-ylmethyl)chroman-7-yl)benzamide;
(17) 2-((3,4-trans)-4-Hydroxy-3-(pyridin-2-ylmethyl)chroman-7-yl)-N-(isobutylsulfonyl)-benzamide;
(18) N-((Cyclopropylmethyl)sulfonyl)-2-((3,4-trans)-4-hydroxy-3-(pyridin-2-ylmethyl)-chroman-7-yl)benzamide;
(19) N-(Cyclopentylsulfonyl)-2-((3,4-trans)-4-hydroxy-3-(pyridin-2-ylmethyl)chroman-7-yl)benzamide;
(20) 2-((3,4-trans)-4-Hydroxy-3-(pyridin-2-ylmethyl)chroman-7-yl)-N-(neopentylsulfonyl)-benzamide;
(21) 2-((3S,4R)-3-Benzyl-4-hydroxychroman-7-yl)-N-((1-methylcyclopropyl)sulfonyl)-benzamide;
(22) 2-((3R,4S)-3-Benzyl-4-hydroxychroman-7-yl)-N-((1-methylcyclopropyl)sulfonyl)-benzamide;
(23) 2-((3S,4R)-3-Benzyl-4-hydroxychroman-7-yl)-N-(cyclopropylsulfonyl)benzamide;
(24) 2-((3R,4S)-3-Benzyl-4-hydroxychroman-7-yl)-N-(cyclopropylsulfonyl)benzamide;
(25) 2-(Rac-trans) 4-Hydroxy-3-(thiazol-4-ylmethyl)chroman-7-yl)-N-((1-methyl-cyclopropyl)sulfonyl)benzamide;
(26) 2-((3S, 4R)-4-Hydroxy-3-(thiazol-4-ylmethyl)chroman-7-yl)-N-((1-methylcyclopropyl)-sulfonyl)benzamide;
(27) 2-((3R,4S)-4-Hydroxy-3-(thiazol-4-ylmethyl)chroman-7-yl)-N-((1-methylcyclopropyl)-sulfonyl)benzamide;
(28) 2-(Rac-trans)-4-Hydroxy-3-((i-methyl-1H-pyrazol-5-yl)methyl)chroman-7-yl)-N-((1-methylcyclopropyl)sulfonyl)benzamide;
(29) 2-((Rac-trans)-4-Hydroxy-3-((5-methyl-1,3,4-thiadiazol-2-yl)methyl)chroman-7-yl)-N-((1-methylcyclopropyl)sulfonyl)benzamide;
(30) 2-((Rac-trans)-3-((1-ethyl-1H-pyrazol-5-yl)methyl)-4-hydroxychroman-7-yl)-N-((1-methylcyclopropyl)sulfonyl)benzamide;
(31) N-(tert-Butylsulfonyl)-2-((rac-trans)-4-hydroxy-3-((5-methyl-1,3,4-thiadiazol-2-yl)methyl)chroman-7-yl)benzamide;
(32) N-(tert-Butylsulfonyl)-2-((rac-trans)-4-hydroxy-3-(thiazol-4-ylmethyl)chroman-7-yl)benzamide;
(33) N-(tert-Butylsulfonyl)-2-((3S,4R)-4-hydroxy-3-(thiazol-4-ylmethyl)chroman-7-yl)benzamide;
(34) N-(tert-Butylsulfonyl)-2-((3R,4S)-4-hydroxy-3-(thiazol-4-ylmethyl)chroman-7-yl)benzamide;
(35) N-(tert-Butylsulfonyl)-2-((rac-trans)-4-hydroxy-3-((1-methyl-1H-pyrazol-5-yl)methyl)chroman-7-yl)benzamide;
(36) N-(tert-Butylsulfonyl)-2-((rac-trans)-3-((1-ethyl-1H-pyrazol-5-yl)methyl)-4-hydroxychroman-7-yl)benzamide;
(37) N-(tert-Butylsulfonyl)-2-((3S,4R)-3-((1-ethyl-1H-pyrazol-5-yl)methyl)-4-hydroxychroman-7-yl)benzamide;
(38) N-(tert-Butylsulfonyl)-2-((3R,4S)-3-((1-ethyl-1H-pyrazol-5-yl)methyl)-4-hydroxychroman-7-yl)benzamide;
(39) 2-((Rac-cis)-3-([1,1'-Biphenyl]-4-ylmethyl)-4-hydroxychroman-7-yl)-4-fluoro-N-((trifluoromethyl)sulfonyl)benzamide;
(40) 2-((Rac-trans)-3-([1,1'-Biphenyl]-4-ylmethyl)-4-hydroxychroman-7-yl)-4-fluoro-N-((trifluoromethyl)sulfonyl)benzamide;
(41) 2-((3R,4S)-3-([1,1'-Biphenyl]-4-ylmethyl)-4-hydroxychroman-7-yl)-4-fluoro-N-((trifluoromethyl)sulfonyl)benzamide;
(42) 2-((3S,4R)-3-([1,1'-Biphenyl]-4-ylmethyl)-4-hydroxychroman-7-yl)-4-fluoro-N-((trifluoromethyl)sulfonyl)benzamide;

(43) 2-(Rac-trans)-4-hydroxy-3-((2-phenyloxazol-4-yl)methyl)chroman-7-yl)-N-((1-methylcyclopropyl)sulfonyl)benzamide;
(44) 2-((3R,4S or 3S,4R)-4-Hydroxy-3-((2-phenyloxazol-4-yl)methyl)chroman-7-yl)-N-((1-methylcyclopropyl)sulfonyl)benzamide;
(45) 2-((3S,4R or 3R,4S)-4-hydroxy-3-((2-phenyloxazol-4-yl)methyl)chroman-7-yl)-N-((1-methylcyclopropyl)sulfonyl)benzamide;
(46) 2-(Rac-trans)-4-Hydroxy-3-((2-phenyloxazol-4-yl)methyl)chroman-7-yl)-N-((1-methylcyclopropyl)sulfonyl)benzamide
(47) N-(tert-Butylsulfonyl)-2-((3R,4S)-4-hydroxy-3-((2-phenyloxazol-4-yl)methyl)chroman-7-yl)benzamide;
(48) N-(tert-Butylsulfonyl)-2-((3S,4R)-4-hydroxy-3-((2-phenyloxazol-4-yl)methyl)chroman-7-yl)benzamide;
(49) 2-((3,4-trans)-4-Hydroxy-3-((R)-1-(pyridin-2-yl)ethyl)chroman-7-yl)-N-((1-methylcyclopropyl)sulfonyl)benzamide; and
(50) 2-((3,4-trans)-4-Hydroxy-3-((S)-1-(pyridin-2-yl)ethyl)chroman-7-yl)-N-((1-methylcyclopropyl)sulfonyl)benzamide;
and pharmaceutically acceptable salts thereof.

Synthetic methods for making the compounds are disclosed in the Examples shown below. Where synthetic details are not provided in the examples, the compounds are readily made by a person of ordinary skill in the art of medicinal chemistry or synthetic organic chemistry by applying the synthetic information provided herein.

Definitions

"Ac" is acetyl, which is $CH_3C(=O)—$.

"Alkyl" means saturated carbon chains which may be linear or branched or combinations thereof, unless the carbon chain is defined otherwise. Other groups having the prefix "alk", such as alkoxy and alkanoyl, also may be linear or branched, or combinations thereof, unless the carbon chain is defined otherwise. The term $—C_2alkyl$ is ethyl. Examples of alkyl groups include methyl, ethyl, propyl, isopropyl, butyl, sec- and tert-butyl, pentyl, neopentyl, hexyl, heptyl, octyl, nonyl, and the like. In one embodiment, alkyl is methyl, tert-butyl, $CH_2$-tert-butyl and neopentyl. In another embodiment, alkyl is methyl and ethyl.

"Cycloalkyl" means a saturated monocyclic, bicyclic or bridged carbocyclic ring, having a specified number of carbon atoms. Examples of cycloalkyl include cyclopropyl, cyclopentyl, cyclohexyl, cycloheptyl, and the like. In one embodiment, cycloalkyl is selected from: cyclopropyl and cyclopentyl. In another embodiment, cycloalkyl is cyclopropyl. In another embodiment, cycloalkyl is cyclopentyl.

"Cycloheteroalkyl" means a saturated monocyclic, bicyclic or bridged carbocyclic ring or ring system containing at least one ring heteroatom selected from N, NH, S (including SO and $SO_2$) and O. The cycloheteroalkyl ring may be substituted on the ring carbons and/or the ring nitrogen(s). Examples of cycloheteroalkyl include tetrahydrofuran, pyrrolidine, tetrahydrothiophene, azetidine, piperazine, piperidine, morpholine, oxetane and tetrahydropyran.

"Aryl" means a monocyclic or bicyclic carbocyclic aromatic ring or ring system containing 5-14 carbon atoms, wherein at least one of the rings is aromatic. Examples of aryl include phenyl and naphthyl. In one embodiment of the present invention, aryl is phenyl.

"Heteroaryl" means monocyclic, or bicyclic ring or ring system containing 3-14 carbon atoms and containing at least one ring heteroatom selected from N, NH, S (including SO and $SO_2$) and O, wherein at least one of the heteroatom containing rings is aromatic. Examples of heteroaryl include pyrazole, pyridine, thiophene, thiazole and benzothiophene. In one embodiment, heteroaryl is pyridine, oxazole, thiazole, or pyrazole. In another embodiment, heteroaryl is pyridine, thiazole, or pyrazole. In another embodiment, heteroaryl is pyridine or pyrazole. In another embodiment, heteroaryl is pyridine. In another embodiment, heteroaryl is pyrazole. In another embodiment, heteroaryl is oxazole, pyrazole or thiazole. In another embodiment, heteroaryl is oxazole, or pyrazole. In another embodiment, heteroaryl is oxazole or thiazole. In another embodiment, heteroaryl is oxazole. In another embodiment, heteroaryl is pyrazole. In another embodiment, heteroaryl is thiazole.

"Halogen" includes fluorine, chlorine, bromine and iodine. In one embodiment of the present invention, halogen is bromine, chlorine or fluorine. In another embodiment of the present invention, halogen is chlorine or fluorine. In another embodiment of the present invention, halogen is bromine. In another embodiment of the present invention, halogen is chlorine. In another embodiment of the present invention, halogen is fluorine.

"Me" represents methyl.

"Oxo" is $=O$.

When any variable (e.g., $R^1$, $R^a$, etc.) occurs more than one time in any constituent or in formula I, its definition on each occurrence is independent of its definition at every other occurrence. Also, combinations of substituents and/or variables are permissible only if such combinations result in stable compounds. A squiggly line across a bond in a substituent variable represents the point of attachment.

Under standard nomenclature used throughout this disclosure, the terminal portion of the designated side chain is described first, followed by the adjacent functionality toward the point of attachment. For example, a $C_{1-5}$ alkylcarbonylamino $C_{1-6}$alkyl substituent is equivalent to:

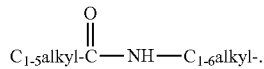

Unless expressly depicted or described otherwise, substituents depicted in a structural formula with a "floating" bond, such as but not limited to Z, are permitted on any available carbon atom in the ring to which the substituent is attached. In one embodiment of the present invention, Z may be substituted on any CH in the ring to which Z is attached.

In choosing compounds of the present invention, one of ordinary skill in the art will recognize that the various substituents, i.e. $R^1$, $R^2$, etc., are to be chosen in conformity with well-known principles of chemical structure connectivity and stability.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

The phrase "pharmaceutically acceptable" is employed herein to refer to those compounds, materials, compositions, salts and/or dosage forms which are, using sound medical judgment, and following all applicable government regulations, safe and suitable for administration to a human being or an animal.

The term "% enantiomeric excess" (abbreviated "ee") shall mean the % major enantiomer less the % minor enantiomer. Thus, a 70% enantiomeric excess corresponds to formation of 85% of one enantiomer and 15% of the other. The term "enantiomeric excess" is synonymous with the term "optical purity."

Compounds of Formula I may contain one or more asymmetric centers and can thus occur as racemates and racemic mixtures, single enantiomers, diastereomeric mixtures and individual diastereomers. The present invention is meant to comprehend all such isomeric forms of the compounds of Formula I.

The present invention encompasses all stereoisomeric forms of the compounds of Formula I. Unless a specific stereochemistry is indicated, the present invention is meant to comprehend all such isomeric forms of these compounds. Centers of asymmetry that are present in the compounds of Formula I can all independently of one another have (R) configuration or (S) configuration. When bonds to the chiral carbon are depicted as straight lines in the structural Formulas of the invention, it is understood that both the (R) and (S) configurations of the chiral carbon, and hence both enantiomers and mixtures thereof, are embraced within the Formula. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. Unless a particular isomer, salt, solvate (including hydrates) or solvated salt of such racemate, enantiomer, diastereomer or tautomer is indicated, the present invention includes all such isomers, as well as salts, solvates (including hydrates) and solvated salts of such racemates, enantiomers, diastereomers and tautomers and mixtures thereof.

Some of the compounds described herein contain olefinic double bonds, and unless specified otherwise, are meant to include both E and Z geometric isomers.

Tautomers are defined as compounds that undergo rapid proton shifts from one atom of the compound to another atom of the compound. Some of the compounds described herein may exist as tautomers with different points of attachment of hydrogen. Such an example may be a ketone and its enol form known as keto-enol tautomers. The individual tautomers as well as mixture thereof are encompassed with compounds of Formula I.

In the compounds of general formula I, the atoms may exhibit their natural isotopic abundances, or one or more of the atoms may be artificially enriched in a particular isotope having the same atomic number, but an atomic mass or mass number different from the atomic mass or mass number predominately found in nature. The present invention is meant to include all suitable isotopic variations of the compounds of structural formula I. For example, different isotopic forms of hydrogen (H) include protium ($^1$H), deuterium ($^2$H), and tritium ($^3$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Tritium is radioactive and may therefore provide for a radiolabeled compound, useful as a tracer in metabolic or kinetic studies. Isotopically-enriched compounds within structural formula I, can be prepared without undue experimentation by conventional techniques well known to those skilled in the art or by processes analogous to those described in the Schemes and Examples herein using appropriate isotopically-enriched reagents and/or intermediates.

The independent syntheses of optical isomers and diastereoisomers or their chromatographic separations may be achieved as known in the art by appropriate modification of the methodology disclosed herein. Their absolute stereochemistry may be determined by the X-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well-known in the art, such as the coupling of a racemic mixture of compounds to an enantiomerically pure compound to form a diastereoisomeric mixture, followed by separation of the individual diastereoisomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

It is generally preferable to administer compounds of the present invention as enantiomerically pure formulations. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

Salts:

It will be understood that, as used herein, references to the compounds of the present invention are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide, trifluoroacetate, and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

Solvates, and in particular, the hydrates of the compounds of the present invention are included in the present invention as well.

Utilities

The compounds of the present invention are potent antagonists of the leukotriene $B_4$ receptor 1 (BLT1) receptor. The compounds, and pharmaceutically acceptable salts thereof, may be efficacious in the treatment of diseases that are modulated by BLT1 ligands. Many of these diseases are summarized below.

One or more of these diseases may be treated by the administration of a therapeutically effective amount of a compound of the present invention, or a pharmaceutically acceptable salt thereof, to a patient in need of treatment. Also, the compounds of the present invention may be used for the manufacture of a medicament which may be useful for treating one or more of these diseases: (1) non-insulin dependent diabetes mellitus (Type 2 diabetes); (2) obesity; (3) hypertension; (4) dyslipidemia and lipid disorders; (5) cancer; (6) Metabolic Syndrome; (7) myocardial infarction; (8) stroke; (9) insulin resistance; (10) hyperglycemia; (11) Non-alcoholic fatty liver disease/nonalcoholic steatohepatitis; and (12) atherosclerosis.

Preferred uses of the compounds may be for the treatment of one or more of the following diseases by administering a therapeutically effective amount to a patient in need of treatment. The compounds may be used for manufacturing a medicament for the treatment of one or more of these diseases: (1) Type 2 diabetes, and specifically hyperglycemia associated with Type 2 diabetes; (2) Metabolic Syndrome; (3) obesity; and (4) hypercholesterolemia.

The compounds may be effective in lowering glucose and lipids in diabetic patients and in non-diabetic patients who have impaired glucose tolerance and/or are in a pre-diabetic condition. The compounds may ameliorate hyperinsulinemia, which often occurs in diabetic or pre-diabetic patients, by modulating the swings in the level of serum glucose that often occurs in these patients. The compounds may also be effective in treating or reducing insulin resistance. The compounds may be effective in treating or preventing gestational diabetes.

The compounds may also be effective in treating or preventing lipid disorders. The compounds may be effective in treating or preventing diabetes related disorders. The compounds may also be effective in treating or preventing obesity related disorders.

The invention also includes pharmaceutically acceptable salts of the compounds, and pharmaceutical compositions comprising the compounds and a pharmaceutically acceptable carrier. The compounds may be useful in treating insulin resistance, Type 2 diabetes, hyperglycemia, and dyslipidemia that is associated with Type 2 diabetes and insulin resistance. The compounds may also be useful for the treatment of obesity A compound of the present invention, or a pharmaceutically acceptable salt thereof, may be used in the manufacture of a medicament for the treatment of Type 2 diabetes in a human or other mammalian patient.

A method of treating Type 2 diabetes comprises the administration of a therapeutically effective amount of a compound of the present invention, or a pharmaceutically acceptable salt thereof, or a pharmaceutical composition comprising the compound, to a human or other mammalian subject or patient in need of treatment. Other medical uses of the compounds of the present invention are described herein.

The term "diabetes," as used herein, includes both insulin-dependent diabetes mellitus (i.e., IDDM, also known as type 1 diabetes) and non-insulin-dependent diabetes mellitus (i.e., NIDDM, also known as Type 2 diabetes). Type 1 diabetes, or insulin-dependent diabetes, is the result of an absolute deficiency of insulin, the hormone which regulates glucose utilization. Type 2 diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type 2 diabetics are also obese. The compositions of the present invention may be useful for treating both Type 1 and Type 2 diabetes. The term "diabetes associated with obesity" refers to diabetes caused by obesity or resulting from obesity.

Diabetes is characterized by a fasting plasma glucose level of greater than or equal to 126 mg/dl. A diabetic subject has a fasting plasma glucose level of greater than or equal to 126 mg/dl. A pre diabetic subject is someone suffering from prediabetes. Prediabetes is characterized by an impaired fasting plasma glucose (FPG) level of greater than or equal to 110 mg/dl and less than 126 mg/dl; or impaired glucose tolerance; or insulin resistance. A prediabetic subject is a subject with impaired fasting glucose (a fasting plasma glucose (FPG) level of greater than or equal to 110 mg/dl and less than 126 mg/dl); or impaired glucose tolerance (a 2 hour plasma glucose level of >140 mg/dl and <200 mg/dl); or insulin resistance, resulting in an increased risk of developing diabetes.

Treatment of diabetes mellitus refers to the administration of a compound or combination of the present invention to treat a diabetic subject. One outcome of treatment may be decreasing the glucose level in a subject with elevated glucose levels. Another outcome of treatment may be decreasing insulin levels in a subject with elevated insulin levels. Another outcome of treatment may be decreasing plasma triglycerides in a subject with elevated plasma triglycerides. Another outcome of treatment is decreasing LDL cholesterol in a subject with high LDL cholesterol levels. Another outcome of treatment may be increasing HDL cholesterol in a subject with low HDL cholesterol levels. Another outcome of treatment is increasing insulin sensitivity. Another outcome of treatment may be enhancing glucose tolerance in a subject with glucose intolerance. Yet another outcome of treatment may be decreasing insulin resistance in a subject with increased insulin resistance or elevated levels of insulin. Prevention of diabetes mellitus, in particular diabetes associated with obesity, refers to the administration of a compound or combination of the present invention to prevent the onset of diabetes in a subject in need thereof. A subject in need of preventing diabetes is a prediabetic subject that is overweight or obese.

The term "diabetes related disorders" should be understood to mean disorders that are associated with, caused by, or result from diabetes. Examples of diabetes related disorders include retinal damage, kidney disease, and nerve damage.

The term "atherosclerosis" as used herein encompasses vascular diseases and conditions that are recognized and understood by physicians practicing in the relevant fields of medicine. Atherosclerotic cardiovascular disease, coronary heart disease (also known as coronary artery disease or ischemic heart disease), cerebrovascular disease and peripheral vessel disease are all clinical manifestations of atherosclerosis and are therefore encompassed by the terms "atherosclerosis" and "atherosclerotic disease." The combination comprised of a therapeutically effective amount of a BLT1 antagonist in combination with a therapeutically effective amount of an anti-hypertensive agent may be administered to prevent or reduce the risk of occurrence, or recurrence where the potential exists, of a coronary heart disease event, a cerebrovascular event, or intermittent claudication. Coronary heart disease events are intended to include CHD death, myocardial infarction (i.e., a heart attack), and coronary revascularization procedures. Cerebrovascular events are intended to include ischemic or hemorrhagic stroke (also known as cerebrovascular accidents) and transient ischemic attacks. Intermittent claudication is a clinical manifestation of peripheral vessel disease. The term "atherosclerotic disease event" as used herein is intended to encompass coronary heart disease events, cerebrovascular events, and intermittent claudication. It is intended that persons who have previously experienced one or more non-fatal atherosclerotic disease events are those for whom the potential for recurrence of such an event exists. The term "atherosclerosis related disorders" should be understood to mean disorders associated with, caused by, or resulting from atherosclerosis.

The term "hypertension" as used herein includes essential, or primary, hypertension wherein the cause is not known or where hypertension is due to greater than one cause, such as changes in both the heart and blood vessels; and secondary hypertension wherein the cause is known. Causes of secondary hypertension include, but are not limited to obesity; kidney disease; hormonal disorders; use of certain drugs, such as oral contraceptives, corticosteroids, cyclosporin, and the like. The term "hypertension" encompasses high blood pressure, in which both the systolic and diastolic pressure levels are elevated (>140 mmHg/>90 mmHg), and isolated systolic hypertension, in which only the systolic pressure is elevated to greater than or equal to 140 mm Hg, while the diastolic pressure is less than 90 mm Hg. Normal blood pressure may be defined as less than 120 mmHg systolic and less than 80 mmHg diastolic. A hypertensive subject is a subject with hypertension. A pre-hypertensive subject is a subject with a blood pressure that is between 120 mmHg over 80 mmHg and 139 mmHg over 89 mmHg. One outcome of treatment is decreasing blood pressure in a subject with high blood pressure. Treatment of hypertension refers to the administration of the compounds and combinations of the present invention to treat hypertension in a hypertensive subject. Treatment of hypertension-related disorder refers to the administration of a compound or combination of the present invention to treat the hypertension-related disorder. Prevention of hypertension, or a hypertension related disorder, refers to the administration of the combinations of the present invention to a pre-hypertensive subject to prevent the onset of hypertension or a hypertension related disorder. The hypertension-related disorders herein are associated with, caused by, or result from hypertension. Examples of hypertension-related disorders include, but are not limited to: heart disease, heart failure, heart attack, kidney failure, and stroke.

Dyslipidemias and lipid disorders are disorders of lipid metabolism including various conditions characterized by abnormal concentrations of one or more lipids (i.e. cholesterol and triglycerides), and/or apolipoproteins (i.e., apolipoproteins A, B, C and E), and/or lipoproteins (i.e., the macromolecular complexes formed by the lipid and the apolipoprotein that allow lipids to circulate in blood, such as LDL, VLDL and IDL). Hyperlipidemia is associated with abnormally high levels of lipids, LDL and VLDL cholesterol, and/or triglycerides. Treatment of dyslipidemia refers to the administration of the combinations of the present invention to a dyslipidemic subject. Prevention of dyslipidemia refers to the administration of the combinations of the present invention to a pre-dyslipidemic subject. A pre-dyslipidemic subject is a subject with higher than normal lipid levels, that is not yet dyslipidemic.

The terms "dyslipidemia related disorders" and "lipid disorder related disorders" should be understood to mean disorders associated with, caused by, or resulting from dyslipidemia or lipid disorders. Examples of dylipidemia related disorder and lipid disorder related disorders include, but are not limited to: hyperlipidemia, hypertriglyceridemia, hypercholesterolemia, low high density lipoprotein (HDL) levels, high plasma low density lipoprotein (LDL) levels, atherosclerosis and its sequelae, coronary artery or carotid artery disease, heart attack, and stroke.

The term "obesity" as used herein is a condition in which there is an excess of body fat. The operational definition of obesity is based on the Body Mass Index (BMI), which is calculated as body weight per height in meters squared ($kg/m^2$). "Obesity" refers to a condition whereby an otherwise healthy subject has a Body Mass Index (BMI) greater than or equal to 30 $kg/m^2$, or a condition whereby a subject with at least one co-morbidity has a BMI greater than or equal to 27 $kg/m^2$. An "obese subject" is an otherwise healthy subject with a Body Mass Index (BMI) greater than or equal to 30 $kg/m^2$ or a subject with at least one co-morbidity with a BMI greater than or equal to 27 $kg/m^2$. An overweight subject is a subject at risk of obesity. A "subject at risk of obesity" is an otherwise healthy subject with a BMI of 25 $kg/m^2$ to less than 30 $kg/m^2$ or a subject with at least one co-morbidity with a BMI of 25 $kg/m^2$ to less than 27 $kg/m^2$.

The increased risks associated with obesity occur at a lower Body Mass Index (BMI) in Asians. In Asian countries, including Japan, "obesity" refers to a condition whereby a subject with at least one obesity-induced or obesity-related co-morbidity, that requires weight reduction or that would be improved by weight reduction, has a BMI greater than or equal to 25 $kg/m^2$. In Asian countries, including Japan, an "obese subject" refers to a subject with at least one obesity-induced or obesity-related co-morbidity that requires weight reduction or that would be improved by weight reduction, with a BMI greater than or equal to 25 $kg/m^2$. In Asia-Pacific, a "subject at risk of obesity" is a subject with a BMI of greater than 23 $kg/m^2$ to less than 25 $kg/m^2$.

As used herein, the term "obesity" is meant to encompass all of the above definitions of obesity.

Obesity-induced or obesity-related co-morbidities include, but are not limited to, diabetes mellitus, non-insulin dependent diabetes mellitus—type 2, diabetes associated with obesity, impaired glucose tolerance, impaired fasting glucose, insulin resistance syndrome, dyslipidemia, hypertension, hypertension associated with obesity, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, and other obesity-related conditions.

Treatment of obesity and obesity-related disorders refers to the administration of the compounds of the present invention to reduce or maintain the body weight of an obese subject. One outcome of treatment may be reducing the body weight of an obese subject relative to that subject's body weight immediately before the administration of the compounds of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in patients in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

Prevention of obesity and obesity-related disorders refers to the administration of the compounds of the present invention to reduce or maintain the body weight of a subject at risk of obesity. One outcome of prevention may be reducing the body weight of a subject at risk of obesity relative to that subject's body weight immediately before the administration of the compounds of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type II diabetes, polycystic ovarian disease, cardiovascular diseases, osteoarthritis, dermatological disorders, hypertension, insulin resistance, hypercholesterolemia, hypertriglyceridemia, and cholelithiasis.

The obesity-related disorders herein are associated with, caused by, or result from obesity. Examples of obesity-related disorders include overeating and bulimia, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovarian disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia. Further examples of obesity-related disorders are metabolic syndrome, also known as syndrome X, insulin resistance syndrome, sexual and reproductive dysfunction, such as infertility, hypogonadism in males and hirsutism in females, gastrointestinal motility disorders, such as obesity-related gastro-esophageal reflux, respiratory disorders, such as obesity-hypoventilation syndrome (Pickwickian syndrome), cardiovascular disorders, inflammation, such as systemic inflammation of the vasculature, arteriosclerosis, hypercholesterolemia, hyperuricaemia, lower back pain, gallbladder disease, gout, and kidney cancer. The compounds of the present invention are also useful for reducing the risk of secondary outcomes of obesity, such as reducing the risk of left ventricular hypertrophy.

The term "metabolic syndrome", also known as syndrome X, is defined in the Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. E. S. Ford et al., JAMA, vol. 287 (3), Jan. 16, 2002, pp 356-359. Briefly, a person is defined as having metabolic syndrome if the person has three or more of the following disorders: abdominal obesity, hypertriglyceridemia, low HDL cholesterol, high blood pressure, and high fasting plasma glucose. The criteria for these are defined in ATP-III. Treatment of metabolic syndrome refers to the administration of the combinations of the present invention to a subject with metabolic syndrome. Prevention of metabolic syndrome refers to the administration of the combinations of the present invention to a subject with two of the disorders that define metabolic syndrome. A subject with two of the disorders that define metabolic syndrome is a subject that has developed two of the disorders that define metabolic syndrome, but has not yet developed three or more of the disorders that define metabolic syndrome.

The terms "administration of" and or "administering a" compound should be understood to mean providing a compound of the invention or a prodrug of a compound of the invention to a human or other mammal in need of treatment.

The term "patient" should be understood to mean a human or other mammal in need of treatment.

The administration of the compound of structural formula I in order to practice the present methods of therapy is carried out by administering a therapeutically effective amount of the compound of structural formula I to the mammal (human or other mammal) in need of such treatment or prophylaxis. The need for a prophylactic administration according to the methods of the present invention is determined via the use of well known risk factors. The therapeutically effective amount of an individual compound is determined, in the final analysis, by the physician or veterinarian in charge of the case, but depends on factors such as the exact disease to be treated, the severity of the disease and other diseases or conditions from which the patient suffers, the chosen route of administration other drugs and treatments which the patient may concomitantly require, and other factors in the physician's judgment.

The usefulness of the present compounds in these diseases or disorders may be demonstrated in animal disease models that have been reported in the literature.

Administration and Dose Ranges

Any suitable route of administration may be employed for providing a mammal, especially a human, with a therapeutically effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of the present invention are administered orally.

In the treatment or prevention of conditions which require antagonism of BLT1 receptor activity, an appropriate dosage level will generally be about 0.01 to 500 mg per kg patient body weight per day which may be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions may preferably be provided in the form of tablets containing 1.0 to 1000 mg of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient for the symptomatic adjustment of the dosage to the patient to be treated. The compounds may be administered on a regimen of 1 to 4 times per day, preferably once or twice per day.

When treating or preventing diabetes mellitus and/or hyperglycemia or hypertriglyceridemia or other diseases for which compounds of the present invention may be indicated, generally satisfactory results could be obtained when the compounds of the present invention are administered at a daily dosage of from about 0.1 mg to about 100 mg per kilogram of animal body weight, preferably given as a single daily dose or in divided doses two to six times a day, or in sustained release form. For most large mammals, the total daily dosage is from about 1.0 mg to about 1000 mg, preferably from about 1 mg to about 50 mg. In the case of a 70 kg adult human, the total daily dose will generally be from about 7 mg to about 350 mg. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the patient undergoing therapy.

The compounds of this invention may be used in pharmaceutical compositions comprising (a) the compound(s) or a pharmaceutically acceptable salt thereof, and (b) a pharmaceutically acceptable carrier. The compounds of this invention may be used in pharmaceutical compositions that include one or more other active pharmaceutical ingredients. The compounds of this invention may also be used in pharmaceutical compositions in which the compound of the present invention or a pharmaceutically acceptable salt thereof is the only active ingredient.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

Combination Therapy

The compounds of the present invention may be useful in methods for the prevention or treatment of the aforementioned diseases, disorders and conditions in combination with other therapeutic agents.

The compounds of the present invention may be useful in combination with one or more other drugs in the treatment, prevention, suppression or amelioration of diseases or conditions for which compounds of formula I or the other drugs may have utility, where the combination of the drugs together are safer, more effective or more therapeutically effective than either drug alone. Such other drug(s) may be administered, by a route and in an amount commonly used therefore, contemporaneously or sequentially with a compound of formula I. When a compound of formula I is used contemporaneously with one or more other drugs, a pharmaceutical composition in unit dosage form containing such other drugs and the compound of formula I is preferred. However, the combination therapy may also include therapies in which the compound of formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of formula I.

Examples of other active ingredients that may be administered separately or in the same pharmaceutical composition in combination with a compound of the formulas described herein include, but are not limited to: (1) dipeptidyl peptidase-IV (DPP-4) inhibitors (e.g., sitagliptin, omarigliptin, trelagliptin, teneligliptin, bisegliptin, anagliptin, vildagliptin, saxagliptin, alogliptin, melogliptin, linagliptin, gosogliptin, evogliptin, and gemigliptin), (2) insulin sensitizers, including (i) PPARγ agonists, such as the glitazones (e.g. pioglitazone, AMG 131, MBX2044, mitoglitazone, lobeglitazone, IDR-105, rosiglitazone, and balaglitazone), and other PPAR ligands, including (1) PPARα/γ dual agonists (e.g., ZYH2, ZYH1, GFT505, chiglitazar, muraglitazar, aleglitazar, sodelglitazar, and naveglitazar); (2) PPARα agonists such as fenofibric acid derivatives (e.g., gemfibrozil, clofibrate, ciprofibrate, fenofibrate, bezafibrate), (3) selective PPARγ modulators (SPPARγM's), (e.g., such as those disclosed in WO 02/060388, WO 02/08188, WO 2004/019869, WO 2004/020409, WO 2004/020408, and WO 2004/066963); and (4) PPARγ partial agonists; (ii) biguanides, such as metformin and its pharmaceutically acceptable salts, in particular, metformin hydrochloride, and extended-release formulations thereof, such as Glumetza™, Fortamet™, and GlucophageXR™; and (iii) protein tyrosine phosphatase-1B (PTP-1B) inhibitors (e.g., ISIS-113715 and TP814); (3) insulin or insulin analogs (e.g., insulin detemir, insulin glulisine, insulin degludec, insulin glargine, insulin lispro and inhalable formulations of each); (4) leptin and leptin derivatives and agonists; (5) amylin and amylin analogs (e.g., pramlintide); (6) sulfonylurea and non-sulfonylurea insulin secretagogues (e.g., tolbutamide, glyburide, glipizide, glimepiride, mitiglinide, meglitinides, nateglinide and repaglinide); (7) α-glucosidase inhibitors (e.g., acarbose, voglibose and miglitol); (8) glucagon receptor antagonists (e.g., MK-3577, MK-0893, LY-2409021 and KT6-971); (9) incretin mimetics, such as GLP-1, GLP-1 analogs, derivatives, and mimetics; and GLP-1 receptor agonists (e.g., dulaglutide, semaglutide, albiglutide, exenatide, liraglutide, lixisenatide, taspoglutide, CJC-1131, and BIM-51077, including intranasal, transdermal, and once-weekly formulations thereof); (10) LDL cholesterol lowering agents such as (i) HMG-CoA reductase inhibitors (e.g., simvastatin, lovastatin, pravastatin, crivastatin, fluvastatin, atorvastatin, pitavastatin and rosuvastatin), (ii) bile acid sequestering agents (e.g., colestilan, colestimide, colesevalam hydrochloride, colestipol, cholestyramine, and dialkylaminoalkyl derivatives of a cross-linked dextran), (iii) inhibitors of cholesterol absorption, (e.g., ezetimibe), and (iv) acyl CoA: cholesterol acyltransferase inhibitors, (e.g., avasimibe); (11) HDL-raising drugs, (e.g., niacin and nicotinic acid receptor agonists, and extended-release versions thereof; (12) anti-obesity compounds; (13) agents intended for use in inflammatory conditions, such as aspirin, non-steroidal anti-inflammatory drugs or NSAIDs, glucocorticoids, and selective cyclooxygenase-2 or COX-2 inhibitors; (14) antihypertensive agents, such as ACE inhibitors (e.g., lisinopril, enalapril, ramipril, captopril, quinapril, and tandolapril), A-II receptor blockers (e.g., losartan, candesartan, irbesartan, olmesartan, medoxomil, valsartan, telmisartan, and eprosartan), renin inhibitors (e.g., aliskiren), beta blockers, and calcium channel blockers; (15) glucokinase activators (GKAs) (e.g., AZD6370); (16) inhibitors of 11β-hydroxysteroid dehydrogenase type 1; (17) CETP inhibitors (e.g., anacetrapib, evacetrapib, torcetrapib, and AT-03); (18) inhibitors of fructose 1,6-bisphosphatase; (19) inhibitors of acetyl CoA carboxylase-1 or 2 (ACC1 or ACC2); (20) AMP-activated Protein Kinase (AMPK) activators (e.g., MB-11055); (21) other agonists of the G-protein-coupled receptors: (i) GPR-109, (ii) GPR-119 (e.g., MBX2982 and PSN821), (iii) GPR-40 (e.g., fasiglifam, JTT-851, TAK-875, and P-11187, and (iv) GPR-120 (e.g., KDT-501); (22) SSTR3 antagonists (e.g., pasireotide, and such as those disclosed in WO 2009/011836); (23) neuromedin U receptor agonists (e.g., such as those disclosed in WO 2009/042053, including, but not limited to, neuromedin S (NMS)); (24) SCD inhibitors; (25) GPR-105 antagonists (e.g., such as those disclosed in WO 2009/000087); (26) SGLT inhibitors (e.g., LIK-066, ASP1941, SGLT-3, ertugliflozin, empagliflozin, dapagliflozin, canagliflozin, BI-10773, PF-04971729, remogliflozin, luseogliflozin, tofogliflozin, ipragliflozin, and LX-4211); (27) inhibitors of (i) acyl coenzyme A:diacylglycerol acyltransferase 1, DGAT-1 (e.g., pradigastat, and P-7435) and acyl coenzyme A:diacylglycerol acyltransferase 2, DGAT-2; (28) inhibitors of fatty acid synthase; (29) inhibitors of acyl coenzyme A:monoacylglycerol acyltransferase 1 and 2 (MGAT-1 and MGAT-2); (30) agonists of the TGR5 receptor (also known as GPBAR1, BG37, GPCR19, GPR131, and M-BAR) (eg., sodium taurocholate); (31) ileal bile acid transporter inhibitors (eg., elobixibat); (32) PACAP, PACAP mimetics, and PACAP receptor 3 agonists; (33) PPAR agonists; (34) protein tyrosine phosphatase-1B (PTP-1B) inhibitors; (35) IL-1b antibodies and inhibitors, (e.g., gevokizumab, canakinumab, danazol, AC-201, and BLX-1002); and (36) bromocriptine mesylate and rapid-release formulations thereof.

Of particular interest are dipeptidyl peptidase-IV (DPP-4) inhibitors that may be useful in combination with compounds of the present invention. Such inhibitors include, without limitation, sitagliptin (disclosed in U.S. Pat. No. 6,699,871), omarigliptin, trelagliptin, teneligliptin, bisegliptin, anagliptin, LC15-0444, vildagliptin, saxagliptin, alogliptin, melogliptin, linagliptin, gosogliptin, evogliptin, gemigliptin, and pharmaceutically acceptable salts thereof, and fixed-dose combinations of these compounds with metformin hydrochloride, pioglitazone, rosiglitazone, simvastatin, atorvastatin, rosuvastatin, or a sulfonylurea.

GPR-40 agonists that may be useful in combination with compounds of the formulas described herein include, but are not limited to: (1) 5-[4-[[(1R)-4-[6-(3-hydroxy-3-methylbutoxy)-2-methylpyridine-3-yl]-2,3-dihydro-1H-indene-1-yl] oxy]phenyl]isothiazole-3-ol 1-oxide; (2) 5-(4-((3-(2,6-dimethyl-4-(3-(methylsulfonyl)propoxy)phenyl)phenyl)-methoxy)-phenyl)isothiazole-3-ol 1-oxide; and (3) 5-(4-((3-

(2-methyl-6-(3-hydroxypropoxy)-pyridine-3-yl)-2-methylphenyl)methoxy)-phenyl)isothiazole-3-ol 1-oxide; and (4) 5-[4-[[3-[4-(3-aminopropoxy)-2,6-dimethylphenyl]phenyl]-methoxy]phenyl]isothiazole-3-ol 1-oxide, and pharmaceutically acceptable salts thereof.

Antiobesity compounds that may be combined with compounds of formula I include topiramate; zonisamide; naltrexone; phentermine; bupropion; the combination of bupropion and naltrexone; the combination of bupropion and zonisamide; the combination of topiramate and phentermine; fenfluramine; dexfenfluramine; sibutramine; lipase inhibitors, such as orlistat and cetilistat; melanocortin receptor agonists, in particular, melanocortin-4 receptor agonists; CCK-1 agonists; melanin-concentrating hormone (MCH) receptor antagonists; neuropeptide $Y_1$ or $Y_5$ antagonists (such as MK-0557); $β_3$ adrenergic receptor agonists; CB-1 receptor inverse agonists and antagonists; ghrelin antagonists; bombesin receptor agonists (such as bombesin receptor subtype-3 agonists); and 5-hydroxytryptamine-2c (5-HT2c) agonists, such as lorcaserin. For a review of anti-obesity compounds that may be useful in combination with a compound of the present invention, see S. Chaki et al., "Recent advances in feeding suppressing agents: potential therapeutic strategy for the treatment of obesity," Expert Opin. Ther. Patents, 11: 1677-1692 (2001); D. Spanswick and K. Lee, "Emerging antiobesity drugs," Expert Opin. Emerging Drugs, 8: 217-237 (2003); J. A. Femandez-Lopez, et al., "Pharmacological Approaches for the Treatment of Obesity," Drugs, 62: 915-944 (2002); and K. M. Gadde, et al., "Combination pharmaceutical therapies for obesity," Exp. Opin. Pharmacother., 10: 921-925 (2009).

Glucagon receptor antagonists that may be useful in combination with the compounds of formula I include, but are not limited to: (1) N-[4-((1S)-1-{3-(3,5-dichlorophenyl)-5-[6-(trifluoromethoxy)-2-naphthyl]-1H-pyrazol-1-yl}ethyl)benzoyl]-β-alanine; (2) N-[4-((1R)-1-{3-(3,5-dichlorophenyl)-5-[6-(trifluoromethoxy)-2-naphthyl]-1H-pyrazol-1-yl}ethyl)benzoyl]-β-alanine; (3) N-(4-{1-[3-(2,5-dichlorophenyl)-5-(6-methoxy-2-naphthyl)-1H-pyrazol-1-yl]ethyl}benzoyl)-β-alanine; (4) N-(4-{(1S)-1-[3-(3,5-dichlorophenyl)-5-(6-methoxy-2-naphthyl)-1H-pyrazol-1-yl]ethyl}benzoyl)-β-alanine; (5) N-(4-{(1S)-1-[(R)-(4-chlorophenyl(7-fluoro-5-methyl-1H-indol-3-yl)methyl]butyl}benzoyl)-β-alanine; and (6) N-(4-{((1S)-1-[(4-chlorophenyl)(6-chloro-8-methylquinolin-4-yl)methyl]butyl}benzoyl)-β-alanine; and pharmaceutically acceptable salts thereof.

Another embodiment of the present invention relates to a pharmaceutical composition comprising one or more of the following agents: (a) a compound of structural formula I; (b) one or more compounds selected from the group consisting of: (1) dipeptidyl peptidase-IV (DPP-4) inhibitors (e.g., sitagliptin, omarigliptin, trelagliptin, teneligliptin, bisegliptin, anagliptin, vildagliptin, saxagliptin, alogliptin, melogliptin, linagliptin, gosogliptin, evogliptin, and gemigliptin); (2) insulin sensitizers, including (i) PPARγ agonists, such as the glitazones (e.g. AMG 131, MBX2044, mitoglitazone, lobeglitazone, IDR-105, pioglitazone, rosiglitazone, and balaglitazone) and other PPAR ligands, including (1) PPARα/γ dual agonists, such as ZYH1, YYH2, chiglitazar, GFT505, muraglitazar, aleglitazar, sodelglitazar, and naveglitazar, (2) PPARα agonists, such as fenofibric acid derivatives (e.g., gemfibrozil, clofibrate, ciprofibrate, fenofibrate and bezafibrate), (3) selective PPARγ modulators (SPPARγM's), (4) PPARγ partial agonists; (ii) biguanides, such as metformin and its pharmaceutically acceptable salts, in particular, metformin hydrochloride, and extended-release formulations thereof, such as Glumetza®, Fortamet®, and GlucophageXR®; (iii) protein tyrosine phosphatase-1B (PTP-1B) inhibitors, such as ISI-13715, and TP814; (3) sulfonylurea and non-sulfonylurea insulin secretagogues, (e.g., tolbutamide, glyburide, glipizide, glimepiride, mitiglinide, and meglitinides, such as nateglinide and repaglinide); (4) α-glucosidase inhibitors (e.g., acarbose, voglibose and miglitol); (5) glucagon receptor antagonists; (6) LDL cholesterol lowering agents such as (i) HMG-CoA reductase inhibitors (e.g., lovastatin, simvastatin, pravastatin, cerivastatin, fluvastatin, atorvastatin, pitavastatin, and rosuvastatin), (ii) bile acid sequestering agents (e.g., colestilan, cholestyramine, colestimide, colesevelam hydrochloride, colestipol, and dialkylaminoalkyl derivatives of a cross-linked dextran), (iii) inhibitors of cholesterol absorption, (e.g., ezetimibe), and (iv) acyl CoA:cholesterol acyltransferase inhibitors (e.g., avasimibe); (7) HDL-raising drugs, such as niacin or a salt thereof; and extended-release versions thereof; and nicotinic acid receptor agonists; (8) antiobesity compounds; (9) agents intended for use in inflammatory conditions, such as aspirin, non-steroidal anti-inflammatory drugs (NSAIDs), glucocorticoids, and selective cyclooxygenase-2 (COX-2) inhibitors; (10) antihypertensive agents, such as ACE inhibitors (e.g., enalapril, lisinopril, ramipril, captopril, quinapril, and tandolapril), A-II receptor blockers (e.g., losartan, candesartan, irbesartan, olmesartan medoxomil, valsartan, telmisartan, and eprosartan), renin inhibitors (e.g., aliskiren), beta blockers (e.g., calcium channel blockers); (11) glucokinase activators (GKAs) (e.g., AZD6370, GKM-001, TMG-123, HMS-5552, DS-7309, PF-04937319, TTP-399, ZYGK-1); (12) inhibitors of 11β-hydroxysteroid dehydrogenase type 1; (13) inhibitors of cholesteryl ester transfer protein (CETP), (e.g., torcetrapib, evacetrapib, anacetrapib, and AT-03); (14) inhibitors of fructose 1,6-bisphosphatase; (15) inhibitors of acetyl CoA carboxylase-1 or 2 (ACC1 or ACC2); (16) AMP-activated Protein Kinase (AMPK) activators (e.g., MB-11055); (17) agonists of the G-protein-coupled receptors: (i) GPR-109, (ii) GPR-119 (e.g., MBX2982, and PSN821), (iii) GPR-40 (e.g., fasiglifam, JTT-851, P-11187, and (iv) GPR-120 (e.g., KDT-501); (18) SSTR3 antagonists (e.g., pasireotide, and such as those disclosed in WO 2009/011836); (19) neuromedin U receptor agonists (e.g., such as those disclosed in WO2009/042053, including, but not limited to, neuromedin S (NMS)); (20) inhibitors of stearoyl-coenzyme A delta-9 desaturase (SCD); (21) GPR-105 antagonists (e.g., such as those disclosed in WO 2009/000087); (22) inhibitors of glucose uptake, such as sodium-glucose transporter (SGLT) inhibitors and its various isoforms, such as SGLT-1; SGLT-2 (e.g., LIK-066, ertuglifozin, ASP1941, luseogliflozin, BI10773, tofogliflozin, LX4211, canagliflozin, dapagliflozin, remogliflozin and ipragliflozin; and SGLT-3); (23) inhibitors of (i) acyl coenzyme A:diacylglycerol acyltransferase 1, DGAT-1 (e.g., pradigastat, and P-7435) and acyl coenzyme A:diacylglycerol acyltransferase 2, DGAT-2; (24) inhibitors of fatty acid synthase; (25) inhibitors of acyl coenzyme A:monoacylglycerol acyltransferase 1 and 2 (MGAT-1 and MGAT-2); (26) agonists of the TGR5 receptor (also known as GPBAR1, BG37, GPCR19, GPR131, and M-BAR) (eg., sodium taurocholate); (28) bromocriptine mesylate and rapid-release formulations thereof, and (29) IL-1b antibodies and inhibitors (e.g., gevokizumab, canakinumab, danazol, AC-201, and BLX-1002); and (c) a pharmaceutically acceptable carrier.

Specific compounds that may be useful in combination with a compound of the present invention include: simvastatin, mevastatin, ezetimibe, atorvastatin, rosuvastatin, sitagliptin, omarigliptin, metformin, sibutramine, orlistat, topiramate, naltrexone, bupriopion, phentermine, losartan, losartan with hydrochlorothiazide, olmesartan, canagliflozin, dapagliflozin, ipragliflozin and ertugliflozin.

The above combinations include combinations of a compound of the present invention not only with one other active compound, but also with two or more other active compounds. Non-limiting examples include combinations of compounds with two or more active compounds selected from biguanides, sulfonylureas, HMG-CoA reductase inhibitors, PPARγ agonists, DPP-4 inhibitors, anti-obesity compounds, and anti-hypertensive agents.

The present invention may also provide a method for the treatment or prevention of a leukotriene $B_4$ receptor 1 (BLT1) mediated disease, which method comprises administration to a patient in need of such treatment or at risk of developing a BLT1 mediated disease of an amount of a BLT1 antagonist and an amount of one or more active ingredients, such that together they give effective relief.

In a further aspect of the present invention, there is provided a pharmaceutical composition comprising a BLT1 antagonist and one or more active ingredients, together with at least one pharmaceutically acceptable carrier or excipient.

Thus, according to a further aspect of the present invention there is provided the use of a BLT1 antagonist and one or more active ingredients for the manufacture of a medicament for the treatment or prevention of a BLT1 mediated disease. In a further or alternative aspect of the present invention, there is therefore provided a product comprising a BLT1 antagonist and one or more active ingredients as a combined preparation for simultaneous, separate or sequential use in the treatment or prevention of a BLT1 mediated disease. Such a combined preparation may be, for example, in the form of a twin pack.

For the treatment or prevention of diabetes, obesity, hypertension, Metabolic Syndrome, dyslipidemia, cancer, atherosclerosis, and related disorders thereof, a compound of the present invention may be used in conjunction with another pharmaceutical agent effective to treat that disorder.

The present invention may also provide a method for the treatment or prevention of diabetes, obesity, hypertension, Metabolic Syndrome, dyslipidemia, cancer, atherosclerosis, and related disorders thereof, which method comprises administration to a patient in need of such treatment an effective amount of a compound of the present invention and an amount of another pharmaceutical agent effective to threat that disorder, such that together they give effective relief.

The present invention may also provide a method for the treatment or prevention of diabetes, obesity, hypertension, Metabolic Syndrome, dyslipidemia, cancer, atherosclerosis, and related disorders thereof, which method comprises administration to a patient in need of such treatment an amount of a compound of the present invention and an amount of another pharmaceutical agent useful in treating that particular condition, such that together they give effective relief.

The term "therapeutically effective amount" or "a therapeutically effective dose" means the amount the compound of structural formula I that will elicit the biological or medical response of a tissue, system, animal, mammal or human that is being sought by the researcher, veterinarian, medical doctor or other clinician, which includes alleviation of the symptoms of the disorder being treated. The novel methods of treatment of this invention are for disorders known to those skilled in the art. The term "mammal" includes, but is not limited to, humans, and companion animals such as dogs and cats.

The weight ratio of the compound of the Formula I to the second active ingredient may be varied and will depend upon the effective dose of each ingredient. Generally, a therapeutically effective dose of each will be used. Thus, for example, when a compound of the Formula I is combined with a DPIV inhibitor the weight ratio of the compound of the Formula I to the DPIV inhibitor will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

Methods of Synthesis of the Compounds of the Present Invention:

The following reaction schemes and Examples illustrate methods which may be employed for the synthesis of the compounds of structural formula I described in this invention. Those skilled in the art will readily understand that known variations of protecting groups, as well as of the conditions and processes of the following preparative procedures, can be used to prepare these compounds. It is also understood that whenever a chemical reagent such as a boronic acid or a boronate is not commercially available, such a chemical reagent can be readily prepared following one of numerous methods described in the literature. All temperatures are degrees Celsius unless otherwise noted. Mass spectra (MS) were measured either by electrospray ion-mass spectroscopy (ESMS) or by atmospheric pressure chemical ionization mass spectroscopy (APCI). All temperatures are degrees Celsius unless otherwise noted.

List of Abbreviations 3,4-cis means 3S,4S or 3R,4R; 3,4-trans means 3S,4R or 3R,4S; Racemic trans or trans racemic or Rac-trans or rac trans means a mixture of 3S,4R and 3R,4S; Racemic cis or cis racemic or Rac-cis or rac cis means a mixture of 3S,4S and 3R,4R; Ac is acetyl; AcCN is acetonitrile; $Ac_2O$ is acetic anhydride; Alk is alkyl; anh. is anhydrous; aq or aq. is aqueous; Ar is aryl; atm is atmosphere; Boc is tert-butoxycarbonyl; Bn-O is phenyl-$CH_2$—O or benzyloxy; n-BuLi is n-butyl lithium; t-BuOK is potassium tert-butoxide; ° C. is degrees celsius; calcd. is calculated; Cbz is benzyloxycarbonyl; $CH_2Cl_2$ is dichloromethane; $ClSO_2Me$ is methanesulfonyl chloride; conc or conc. is concentrated; CPME is cyclopropyl methyl ether; CV is column volumes; DCM is dichloromethane; DEA is diethyl amine; DIPEA is N,N-diisopropylethylamine; DIPA is diisopropyl amine; DMAP is 4-dimethylaminopyridine; DMF is N,N-dimethylformamide; DMS is dimethyl sulfide; DMSO is dimethylsulfoxide; EA or EtOAc is ethyl acetate; Et is ethyl; $Et_3N$ is triethyl amine; $Et_2O$ is diethyl ether; EtMgBr is ethyl magnesium bromide; EtOH is ethanol; g is gram(s); h or hr or hrs is hour(s); hex is hexanes; HPLC is high pressure liquid chromatography; HOAc or AcOH is acetic acid; kg is kilogram(s); IPA is isopropanol; KOAc is potassium acetate; KOtBu is potassium tert-butoxide; KHMDS is potassium hexamethyl disilazide; L is liter; LAH is lithium aluminum hydride; M is molar; LC-MS,LCMS or LC/MS is liquid chromatography-mass spectroscopy; LDA is lithium diisopropyl amide; Me is methyl; MeO is methoxy; m-CPBA, MCPBA, or mCPBA is meta chloroperbenzoic acid; ml or mL is milliliter; min or mins is minute(s); mol is mole(s); mmol is mmole(s); mg is milligram(s); MeOH is methyl alcohol or methanol; MPLC is medium pressure liquid chromatography; MS is mass spectroscopy; MsCl or Ms-Cl is methane sulfonyl chloride; MeCN is acetonitrile; MeI is methyl iodide; MTBE is methyl tert-butyl ether; N is normal; NaHMDS is sodium hexamethyl disilazide; NH₄OAc is ammonium acetate; NBS is N-bromo succinamide; NEt₃ is triethyl amine; NMP is 1-methyl-2-pyrrolidinone; NMR is nuclear magnetic resonance spectroscopy; o.n. or ON is overnight; Pd(PPh₃)₄ is tetrakis(triphenylphosphine)palladium; PE is petroleum ether; i-PrOH is isopropanol; Pd(OAc)₂ is palladium acetate; prep is preparative; prep. TLC or prep-TLC, or prep TCL is preparative thin layer chromatography; psi is pounds per square inch; rac is racemic; rt or r.t. or RT is room temperature; $R_f$ is retention factor; sat or sat. is saturated; SFC is supercritical fluid chromatography; TBAF is tetrabutylammonium fluoride; TBSCl is tert-butyl dimethylsilyl chloride; TEA is triethyl amine; Tf is trifluoromethane sulfonyl; 2-Me THF is 2-methyltetrahydrofuran; THF is tetrahydrofuran; TFA is trifluoroacetic acid; TLC is thin-layer chromatography; p-Tos, Tos and Ts is p-toluene sulfonyl; TosCl and TsCl is p-toluene sulfonyl chloride; pTSA, pTsOH and TsOH is p-toluenesulfonic acid; Ts₂O is tosic anhydride or p-toluene sulfonic anhydride; and 2$^{nd}$ Generation Xphos precatalyst is chloro(2-dicyclohexyl-phosphino-2',4',6'-triisopropyl-1,1'-biphenyl)[2-(2'-amino-1,1'-biphenyl)]palladium(II).

Several methods for preparing the compounds of this invention are illustrated in the following Scheme and Examples. Starting materials are either commercially available or made by known procedures in the literature or as illustrated. The present invention further provides processes for the preparation of compounds of structural formula I as defined above. In some cases the order of carrying out the foregoing reaction schemes may be varied to facilitate the reaction or to avoid unwanted reaction products. The following Schemes and Examples are provided to illustrate the invention and are not to be construed as limiting the invention in any manner. The scope of the invention is defined by the appended claims.

Intermediates 1 and 2

Synthesis of (3S,4R or 3R,4S)-3-(pyridin-2-ylmethyl)-7-(4,4,5,5-tetramethyl-1,3,2-dioxaborolan-2-yl)chroman-4-ol (1) and (3R,4S or 3S,4R)-3-(pyridin-2-ylmethyl)-7-(4,4,5,5-tetramethyl-1,3,2-dioxaborolan-2-yl)chroman-4-ol (2)

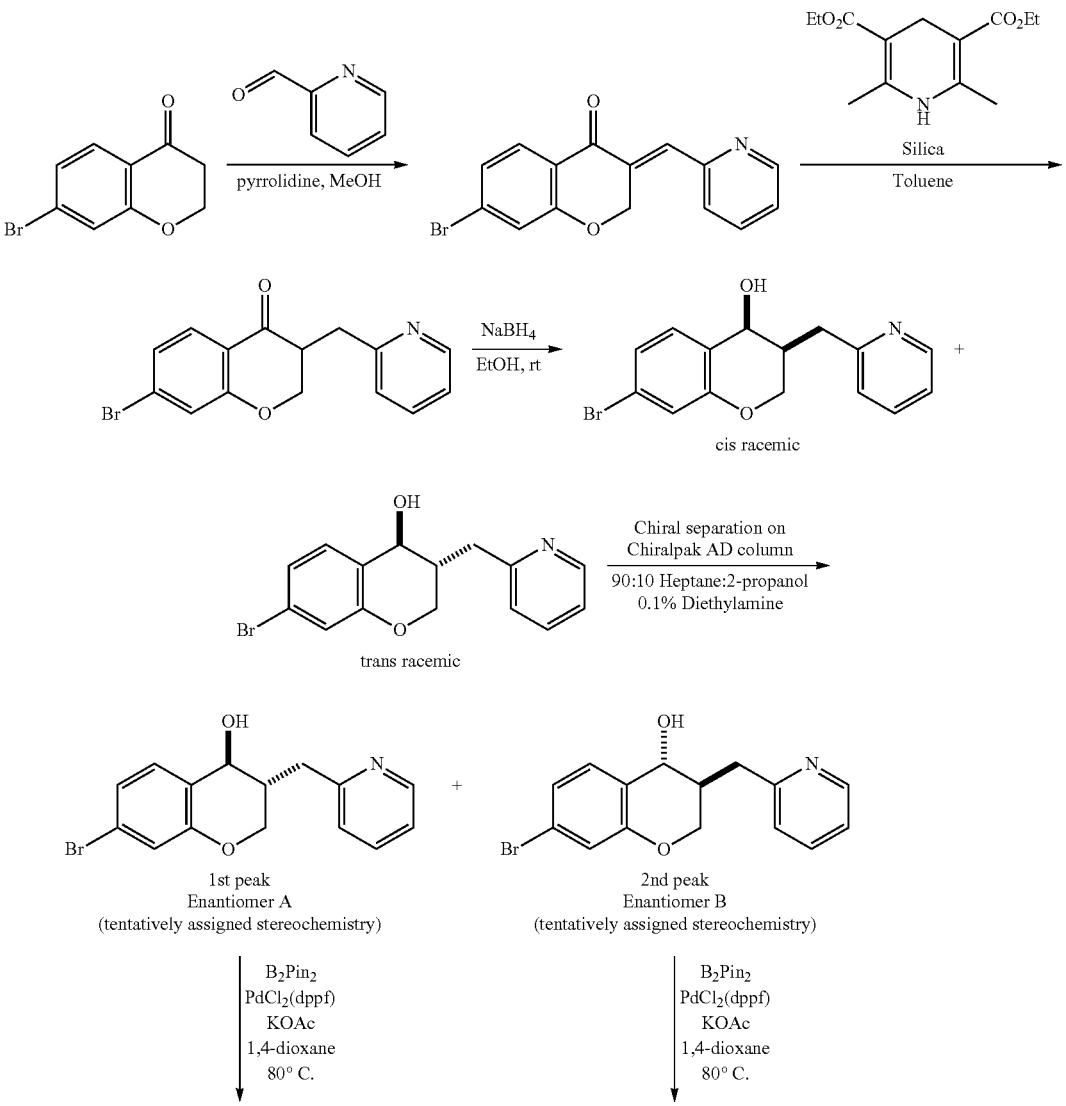

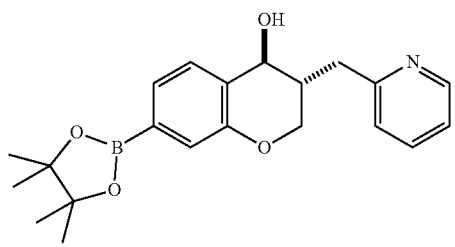

Intermediate 1 Enantiomer A
(tentatively assigned stereochemistry)

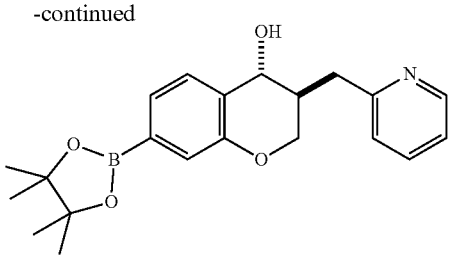

Intermediate 2 Enantiomer B
(tentatively assigned stereochemistry)

Step 1: (E)-7-bromo-3-(pyridin-2-ylmethylene)chroman-4-one

7-Bromochroman-4-one (15.0 g, 66.1 mmol), picolinaldehyde (8.49 g, 79 mmol), pyrrolidine (6.56 ml, 79 mmol) and MeOH (50 ml) were combined, placed under an argon atmosphere, and stirred for 16 hours. The resulting solid was filtered, washed with MeOH (30 ml) and dried under vacuum to obtain the title compound. $^1$H NMR (400 MHz, CDCl$_3$) δ 8.72-8.71 (m, 1H), 7.87 (d, J=9.6 Hz, 1H), 7.78-7.69 (m, 2H), 7.50 (d, J=8.4 Hz, 1H), 7.28-7.17 (m, 3H), 5.92 (s, 2H).

Step 2: 7-bromo-3-(pyridin-2-ylmethyl)chroman-4-one (E)-7-Bromo-3-(pyridin-2-ylmethylene)chroman-4-one (18.3 g, 57.9 mmol), diethyl 2,6-dimethyl-1,4-dihydropyridine-3,5-dicarboxylate (19.06 g, 75 mmol), silica (110 g, 1.83 mol) and degassed toluene (180 mL) were combined. The mixture was placed under a nitrogen atmosphere and refluxed for 20 hours. Then the reaction mixture was filtered and the filtrate was concentrated under reduced pressure. The resulting residue was purified by column chromatography on silica (0-50% EtOAc/hexanes) to obtain the title compound. MS ESI calcd. for C$_{15}$H$_{13}$BrNO$_2$ [M+H]$^+$ 319, found 319.

Step 3

7-Bromo-3-(pyridin-2-ylmethyl)chroman-4-one (14.5 g, 45.6 mmol), sodium borohydride (3.45 g, 91 mmol) and methanol (80 mL) were combined. The solution was placed under a nitrogen atmosphere and stirred for 3 hours. Then the reaction mixture was poured into saturated aqueous ammonium chloride (30 mL), extracted with ethyl acetate (30 mL×2). The combined organic layers were dried over anhydrous magnesium sulfate, filtered and concentrated under reduced pressure. The resulting residue was purified by column chromatography on silica (0-70% EtOAc/hexanes) to obtain (rac-cis)-7-bromo-3-(pyridin-2-ylmethyl)chroman-4-ol (first eluting): MS ESI calcd. for C$_{15}$H$_{15}$BrNO$_2$ [M+H]$^+$ 321, found 321, and (rac-trans)-7-bromo-3-(pyridin-2-ylmethyl)chroman-4-ol (second eluting): MS ESI calcd. for C$_{15}$H$_{15}$BrNO$_2$ [M+H]$^+$ 321, found 321.

Step 4

(Rac-trans)-7-bromo-3-(pyridin-2-ylmethyl)chroman-4-ol (1.0 g, 3.12 mmol) was separated into single enantiomers using preparative chiral HPLC (Chiralpak AD column (5-10% IPA/n-heptane, 0.1% diethylamine) to give: (3R,4S or 3S,4R)-7-bromo-3-(pyridin-2-ylmethyl)chroman-4-ol (Enantiomer A, 1st eluted enantiomer, MS ESI calcd. for C$_{15}$H$_{15}$BrNO$_2$ [M+H]$^+$ 321, found 321), and (3S,4R or 3R,4S)-7-bromo-3-(pyridin-2-ylmethyl)chroman-4-ol (Enantiomer B, 2nd eluted enantiomer; MS ESI calcd. for C$_{15}$H$_{15}$BrNO$_2$ [M+H]$^+$ 321, found 321).

Step 5: (3R,4S or 3S,4R)-3-(pyridin-2-ylmethyl)-7-(4,4,5,5-tetramethyl-1,3,2-dioxaborolan-2-yl)chroman-4-ol (3R,4S or 3S,4R)-7-Bromo-3-(pyridin-2-ylmethyl)chroman-4-ol (1.5 g, 4.68 mmol; Enantiomer A, Step 4), bis(pinacolato)diboron (1.31 g, 5.16 mmol), [1,1'-bis(diphenylphosphino)-ferrocene]dichloropalladium(II) (0.343 g, 0.468 mmol), potassium acetate (1.15 g, 11.73 mmol) and 1,4-dioxane (30 ml) were combined. The solution was stirred at 80° C. for 16 hours. Then the solution was concentrated, diluted with water (30 ml) and extracted with ethyl acetate (30 ml×2). The combined organic layer was dried over sodium sulfate, filtered and concentrated under reduced pressure. The resulting residue was purified by column chromatography on silica (0-70% EtOAc-Hexanes) to obtain (3R,4S or 3S,4R)-3-(pyridin-2-ylmethyl)-7-(4,4,5,5-tetramethyl-1,3,2-dioxaborolan-2-yl)chroman-4-ol. $^1$H NMR (400 MHz, CDCl$_3$) δ 8.53-8.52 (m, 1H), 7.65-7.62 (m, 1H), 7.46 (d, J=7.6 Hz, 1H), 7.38 (d, J=7.6 Hz, 1H), 7.26 (s, 1H), 7.17-7.15 (m, 1H), 4.63 (d, J=6.4 Hz, 1H), 4.24 (dd, J=11.6 Hz, 3.2 Hz, 1H), 3.98 (dd, J=11.2 Hz, 7.6 Hz, 1H), 2.94 (dd, J=14.0 Hz, 7.2 Hz, 1H), 2.78 (dd, J=14.4 Hz, 6.4 Hz, 1H), 2.51-2.49 (m, 1H), 1.33 (s, 12H).

(3S,4R or 3R,4S)-3-(pyridin-2-ylmethyl)-7-(4,4,5,5-tetramethyl-1,3,2-dioxaborolan-2-yl)chroman-4-ol The title compound was synthesized following the same procedure described for Enantiomer A (1st eluted enantiomer of Step 4) starting from (3S,4R or 3R,4S)-7-bromo-3-(pyridin-2-ylmethyl)chroman-4-ol (Enantiomer B, 2nd eluted enantiomer of Step 4). $^1$H NMR (400 MHz, CDCl$_3$) δ 8.54-8.53 (m, 1H), 7.65-7.61 (m, 1H), 7.46 (d, J=7.6 Hz, 1H), 7.38 (d, J=7.6 Hz, 1H), 7.27 (s, 1H), 7.18-7.15 (m, 1H), 4.62 (d, J=6.4 Hz, 1H), 4.25 (dd, J=11.2 Hz, 3.2 Hz, 1H), 3.98 (dd, J=11.2 Hz, 8.0 Hz, 1H), 2.94 (dd, J=14.8 Hz, 7.2 Hz, 1H), 2.78 (dd, J=14.8 Hz, 6.4 Hz, 1H), 2.51-2.49 (m, 1H), 1.33 (s, 12H).

Example 1

4-Fluoro-2-((3R,4S or 3S,4R)-4-hydroxy-3-(pyridin-2-ylmethyl)chroman-7-yl)-N-((trifluoromethyl)sulfonyl)benzamide

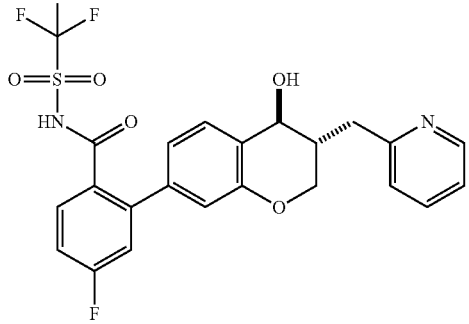

Step 1: 2-bromo-4-fluoro-N-((trifluoromethyl)sulfonyl)benzamide

2-Bromo-4-fluorobenzoyl chloride (3.19 g, 13.4 mmol), trifluoromethanesulfonamide (2 g, 13.4 mmol), triethylamine (5.6 ml, 40 mmol) and MTBE (10 mL) were combined under argon atmosphere and the reaction was heated to 50° C. for 16 h. Then the reaction mixture was cooled to room temperature and concentrated under reduced pressure. The resulting residue was purified by column chromatography on silica (30-80% EtOAc/hexanes) to obtain the title compound. $^1$H NMR (400 MHz, CD$_3$OD) δ 7.64-7.59 (m, 1H), 7.56-7.51 (dd, J=8.5 Hz, 2.4 Hz, 1H), 7.28-7.21 (m, 1H).

Step 2: (3R,4S or 3S,4R)-3-(pyridin-2-ylmethyl)-7-(4,4,5,5-tetramethyl-1,3,2-dioxaborolan-2-yl)chroman-4-ol (3R,4S or 3S,4R)-3-(pyridin-2-ylmethyl)-7-(4,4,5,5-tetramethyl-1,3,2-dioxaborolan-2-yl)chroman-4-ol (53 mg, 0.143 mmol), 2-bromo-4-fluoro-N-((trifluoromethyl)sulfonyl)benzamide (50 mg, 0.143 mmol), 2M Na$_2$CO$_3$ (0.35 mL, 0.70 mmol) and 1,4-dioxane (2 mL) were combined. The mixture was placed under an argon atmosphere by performing 2 vacuum/argon cycles. Then Pd(PPh$_3$)$_4$ (32.0 mg, 0.028 mmol) was added and the reaction was stirred at 100° C. for 14 h. Then the reaction mixture was concentrated, diluted with water (6 mL), acidified to pH~5 using 2N HCl and extracted with ethyl acetate (10 mL×3). The combined organic layers were dried over anhydrous magnesium sulfate, filtered and concentrated under reduced pressure. The resulting residue was purified by column chromatography on silica (0-10% DCM-MeOH) to provide the title compound. MS ESI calcd. for C$_{23}$H$_{17}$F$_4$N$_2$O$_5$S [M−H]$^-$ 509, found 509.

Example 2

4-Fluoro-2-((3S,4R or 3R,4S)-4-hydroxy-3-(pyridin-2-ylmethyl)chroman-7-yl)-N-((trifluoromethyl)sulfonyl)benzamide

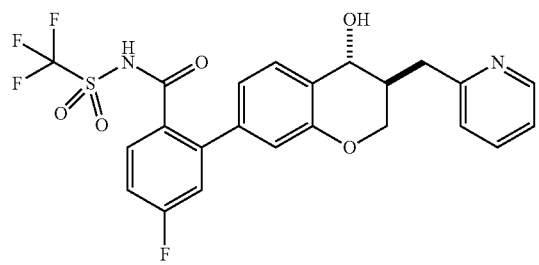 [SMILES: O=C(NS(=O)(=O)C(F)(F)F)c1ccc(F)cc1-c1ccc2c(c1)OC[C@H](Cc1ccccn1)[C@H]2O]

The title compound was synthesized according to the procedure of Example 1 using (3S,4R or 3R,4S)-3-(pyridin-2-ylmethyl)-7-(4,4,5,5-tetramethyl-1,3,2-dioxaborolan-2-yl)chroman-4-ol and 2-bromo-4-fluoro-N-((trifluoromethyl)sulfonyl)benzamide. MS ESI calcd. for C$_{23}$H$_{17}$F$_4$N$_2$O$_5$S [M−H]$^-$ 509, found 509.

Example 3

4-Fluoro-2-((3R,4S or 3S,4R)-4-hydroxy-3-(pyridin-2-ylmethyl)chroman-7-yl)-N-(methylsulfonyl)benzamide

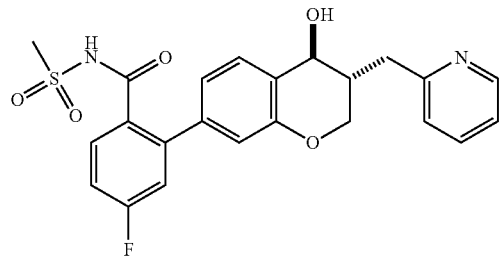 [SMILES: CS(=O)(=O)NC(=O)c1ccc(F)cc1-c1ccc2c(c1)OC[C@@H](Cc1ccccn1)[C@@H]2O]

The title compound was synthesized according to the procedure of Example 1 using (3R,4S or 3S,4R)-3-(pyridin-2-ylmethyl)-7-(4,4,5,5-tetramethyl-1,3,2-dioxaborolan-2-yl)chroman-4-ol and 2-bromo-4-fluoro-N-(methylsulfonyl)benzamide. MS ESI calcd. for C$_{23}$H$_{22}$FN$_2$O$_5$S [M+H]$^+$ 457, found 457.

Example 4

4-Fluoro-2-((3S,4R or 3R,4S)-4-hydroxy-3-(pyridin-2-ylmethyl)chroman-7-yl)-N-(methylsulfonyl)benzamide

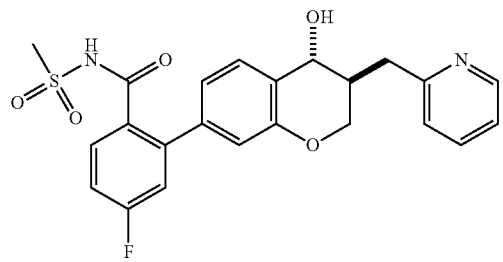 [SMILES: CS(=O)(=O)NC(=O)c1ccc(F)cc1-c1ccc2c(c1)OC[C@H](Cc1ccccn1)[C@H]2O]

The title compound was synthesized according to the procedure described for Example 1 starting from (3S,4R or 3R,4S)-3-(pyridin-2-ylmethyl)-7-(4,4,5,5-tetramethyl-1,3,2-dioxaborolan-2-yl)chroman-4-ol and 2-bromo-4-fluoro-N-(methylsulfonyl)benzamide. MS ESI calcd. for $C_{23}H_{20}FN_2O_5S$ [M−H]⁻ 455, found 455.

Example 5

N-(Cyclopropylsulfonyl)-2-((3R,4S or 3S,4R)-4-hydroxy-3-(pyridin-2-ylmethyl)chroman-7-yl)benzamide

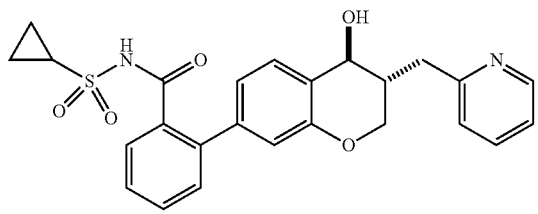 [SMILES: O=C(NS(=O)(=O)C1CC1)c1ccccc1-c1ccc2c(c1)OC[C@@H](Cc1ccccn1)[C@@H]2O]

The title compound was synthesized according to the procedure of Example 1 using (3R,4S or 3S,4R)-3-(pyridin-2-ylmethyl)-7-(4,4,5,5-tetramethyl-1,3,2-dioxaborolan-2-yl)chroman-4-ol and 2-bromo-N-(cyclopropylsulfonyl)benzamide. MS ESI calcd. for $C_{25}H_{25}N_2O_5S$ [M+H]⁺ 465, found 465.

Example 6

N-(Cyclopropylsulfonyl)-2-((3S,4R or 3R,4S)-4-hydroxy-3-(pyridin-2-ylmethyl)chroman-7-yl)benzamide

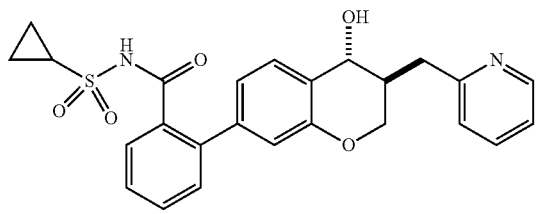 [SMILES: O=C(NS(=O)(=O)C1CC1)c1ccccc1-c1ccc2c(c1)OC[C@H](Cc1ccccn1)[C@H]2O]

The title compound was synthesized according to the procedure of Example 1 using (3S,4R or 3R,4S)-3-(pyridin-2-ylmethyl)-7-(4,4,5,5-tetramethyl-1,3,2-dioxaborolan-2-yl)chroman-4-ol and 2-bromo-N-(cyclopropylsulfonyl)benzamide MS ESI calcd. for $C_{25}H_{23}N_2O_5S$ [M−H]⁻ 463, found 463.

Example 7

2-((3R,4S or 3S,4R)-4-Hydroxy-3-(pyridin-2-ylmethyl)chroman-7-yl)-N-((1-methylcyclopropyl)sulfonyl)benzamide

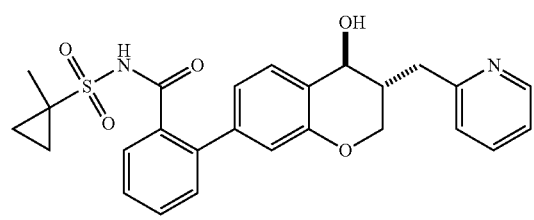 [SMILES: CC1(S(=O)(=O)NC(=O)c2ccccc2-c2ccc3c(c2)OC[C@@H](Cc2ccccn2)[C@@H]3O)CC1]

The title compound was synthesized according to the procedure of Example 1 using (3R,4S or 3S,4R)-3-(pyridin-2-ylmethyl)-7-(4,4,5,5-tetramethyl-1,3,2-dioxaborolan-2-yl)chroman-4-ol and 2-bromo-N-((1-methylcyclopropyl)sulfonyl)benzamide. MS ESI calcd. for $C_{26}H_{27}N_2O_5S$ [M+H]⁺ 479, found 479.

Example 8

2-((3S,4R or 3R,4S)-4-Hydroxy-3-(pyridin-2-ylmethyl)chroman-7-yl)-N-((1-methylcyclopropyl)sulfonyl)benzamide

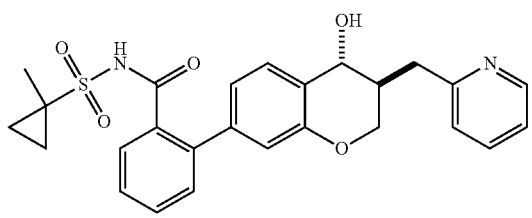 [SMILES: CC1(S(=O)(=O)NC(=O)c2ccccc2-c2ccc3c(c2)OC[C@H](Cc2ccccn2)[C@H]3O)CC1]

The title compound was synthesized according to the procedure of Example 1 using ((3S,4R or 3R,4S)-3-(pyridin-2-ylmethyl)-7-(4,4,5,5-tetramethyl-1,3,2-dioxaborolan-2-yl)chroman-4-ol and 2-bromo-N-((1-methylcyclopropyl)sulfonyl)-benzamide. MS ESI calcd. for $C_{26}H_{27}N_2O_5S$ [M+H]⁺ 479, found 479.

Example 9

4-Fluoro-2-((3S,4R or 3R,4S)-4-hydroxy-3-(pyridin-2-ylmethyl)chroman-7-yl)-N-((1-methylcyclopropyl)sulfonyl)benzamide

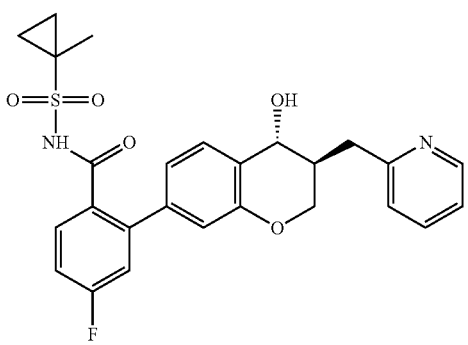 [SMILES: CC1(S(=O)(=O)NC(=O)c2ccc(F)cc2-c2ccc3c(c2)OC[C@H](Cc2ccccn2)[C@H]3O)CC1]

The title compound was synthesized according to the procedure of Example 1 using (3S,4R or 3R,4S)-3-(pyridin-2-ylmethyl)-7-(4,4,5,5-tetramethyl-1,3,2-dioxaborolan-2-yl)chroman-4-ol and 2-bromo-4-fluoro-N-((1-methylcyclopropyl)sulfonyl)benzamide. MS ESI calcd. for $C_{26}H_{26}FN_2O_5S$ [M+H]⁺ 497, found 497.

Example 10

4-Fluoro-2-((3R,4S or 3S,4R)-4-hydroxy-3-(pyridin-2-ylmethyl)chroman-7-yl)-N-((1-methylcyclopropyl)sulfonyl)benzamide

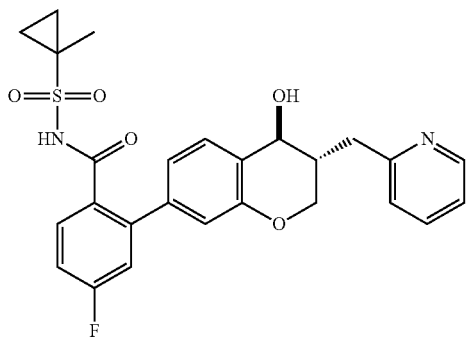 [SMILES: CC1(S(=O)(=O)NC(=O)c2ccc(F)cc2-c2ccc3c(c2)OC[C@@H](Cc2ccccn2)[C@@H]3O)CC1]

The title compound was synthesized according to the procedure of Example 1 using (3R,4S or 3S,4R)-3-(pyridin-2-ylmethyl)-7-(4,4,5,5-tetramethyl-1,3,2-dioxaborolan-2-yl)chroman-4-ol and 2-bromo-4-fluoro-N-((1-methylcyclopropyl)sulfonyl)benzamide. MS ESI calcd. for $C_{26}H_{24}FN_2O_5S$ [M–H]$^-$ 495, found 495.

Example 11

N-(tert-Butylsulfonyl)-2-((3R,4S or 3S,4R)-4-hydroxy-3-(pyridin-2-ylmethyl)chroman-7-yl)benzamide

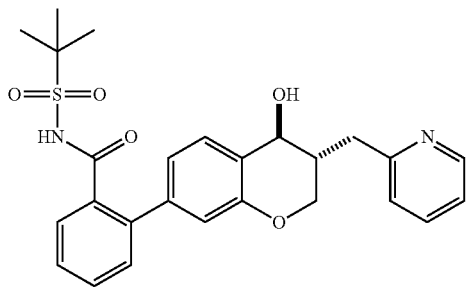 [SMILES: CC(C)(C)S(=O)(=O)NC(=O)c1ccccc1-c1ccc2c(c1)OC[C@@H](Cc1ccccn1)[C@@H]2O]

The title compound was synthesized according to the procedure of Example 1 using (3R,4S or 3S,4R)-3-(pyridin-2-ylmethyl)-7-(4,4,5,5-tetramethyl-1,3,2-dioxaborolan-2-yl)chroman-4-ol and 2-bromo-N-(tert-butylsulfonyl)benzamide. MS ESI calcd. for $C_{26}H_{29}N_2O_5S$ [M+H]$^+$ 481, found 481.

Example 12

N-(tert-Butylsulfonyl)-2-((3S,4R or 3R,4S)-4-hydroxy-3-(pyridin-2-ylmethyl)chroman-7-yl)benzamide

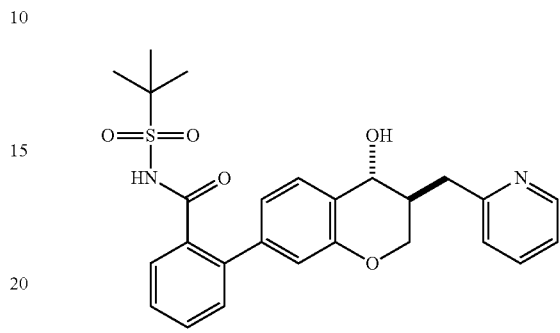

The title compound was synthesized according to the procedure of Example 1 using (3S,4R or 3R,4S)-3-(pyridin-2-ylmethyl)-7-(4,4,5,5-tetramethyl-1,3,2-dioxaborolan-2-yl)chroman-4-ol 2-bromo-N-(tert-butylsulfonyl)benzamide. MS ESI calcd. for $C_{26}H_{29}N_2O_5S$ [M+H]$^+$ 481, found 481.

Example 13

N-(tert-Butylsulfonyl)-4-fluoro-2-((3R,4S or 3S,4R)-4-hydroxy-3-(pyridin-2-ylmethyl)chroman-7-yl)benzamide

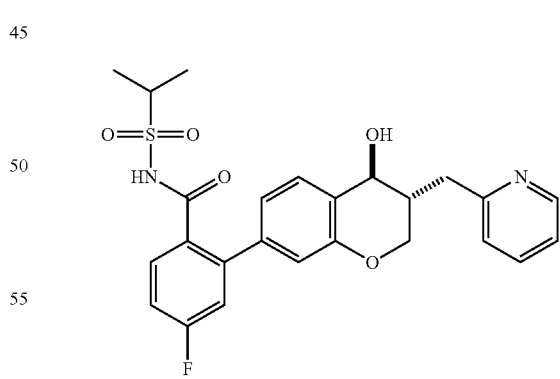

The title compound was synthesized according to the procedure of Example 1 using (3R,4S or 3S,4R)-3-(pyridin-2-ylmethyl)-7-(4,4,5,5-tetramethyl-1,3,2-dioxaborolan-2-yl)chroman-4-ol and 2-bromo-N-(tert-butylsulfonyl)-4-fluorobenzamide. MS ESI calcd. for $C_{26}H_{26}FN_2O_5S$ [M–H]$^-$ 497, found 497.

Example 14

N-(tert-Butylsulfonyl)-4-fluoro-2-((3S,4R or 3R,4S)-4-hydroxy-3-(pyridin-2-ylmethyl)chroman-7-yl)benzamide

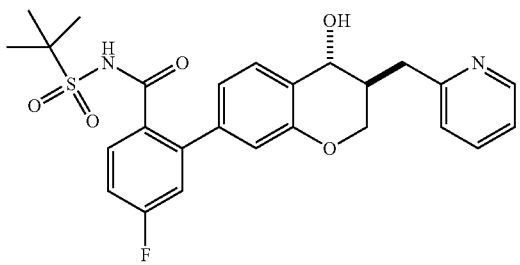 [SMILES: CC(C)(C)S(=O)(=O)NC(=O)c1ccc(F)cc1-c1ccc2c(c1)OC[C@H](Cc1ccccn1)[C@H]2O]

The title compound was synthesized according to the procedure of Example 1 using (3S,4R or 3R,4S)-3-(pyridin-2-ylmethyl)-7-(4,4,5,5-tetramethyl-1,3,2-dioxaborolan-2-yl)chroman-4-ol and 2-bromo-N-(tert-butylsulfonyl)-4-fluorobenzamide. MS ESI calcd. for $C_{26}H_{28}FN_2O_5S$ $[M+H]^+$ 499, found 499.

Example 15

N-(Cyclopropylsulfonyl)-4-fluoro-2-((3R,4S or 3S,4R)-4-hydroxy-3-(pyridin-2-ylmethyl)chroman-7-yl)benzamide

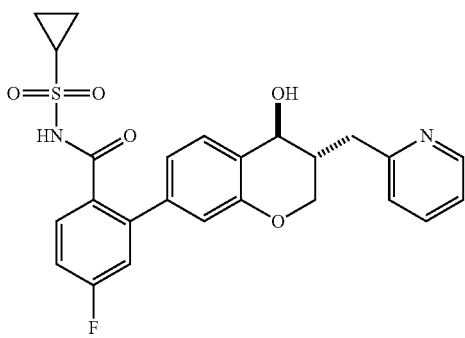 [SMILES: O=C(NS(=O)(=O)C1CC1)c1ccc(F)cc1-c1ccc2c(c1)OC[C@@H](Cc1ccccn1)[C@@H]2O]

The title compound was synthesized according to the procedure of Example 1 using (3R,4S or 3S,4R)-3-(pyridin-2-ylmethyl)-7-(4,4,5,5-tetramethyl-1,3,2-dioxaborolan-2-yl)chroman-4-ol and 2-bromo-N-(cyclopropylsulfonyl)-4-fluorobenzamide. MS ESI calcd. for $C_{25}H_{24}FN_2O_5S$ $[M+H]^+$ 483, found 483.

Example 16

N-(Cyclopropylsulfonyl)-4-fluoro-2-((3S,4R or 3R,4S)-4-hydroxy-3-(pyridin-2-ylmethyl)chroman-7-yl)benzamide

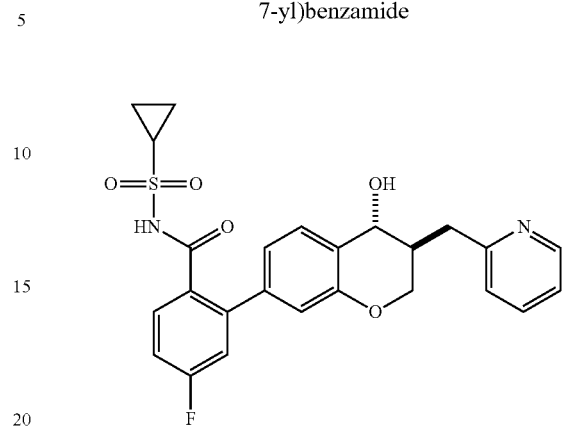

The title compound was synthesized according to the procedure of Example 1 using (3S,4R or 3R,4S)-3-(pyridin-2-ylmethyl)-7-(4,4,5,5-tetramethyl-1,3,2-dioxaborolan-2-yl)chroman-4-ol and 2-bromo-N-(cyclopropylsulfonyl)-4-fluorobenzamide. MS ESI calcd. for $C_{25}H_{24}FN_2O_5S$ $[M+H]^+$ 483, found 483.

Example 17

2-((3,4-trans)-4-Hydroxy-3-(pyridin-2-ylmethyl)chroman-7-yl)-N-(isobutylsulfonyl)benzamide

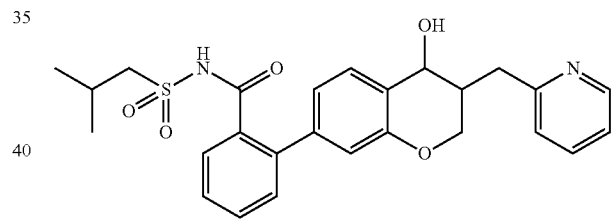

The title compound was synthesized according to the procedure of Example 1 using (3R,4S or 3S,4R)-3-(pyridin-2-ylmethyl)-7-(4,4,5,5-tetramethyl-1,3,2-dioxaborolan-2-yl)chroman-4-ol and 2-bromo-N-(isobutylsulfonyl)benzamide. MS ESI calcd. for $C_{26}H_{27}N_2O_5S$ $[M-H]^-$ 479, found 479.

Example 18

N-((Cyclopropylmethyl)sulfonyl)-2-((3,4-trans)-4-hydroxy-3-(pyridin-2-ylmethyl)chroman-7-yl)benzamide

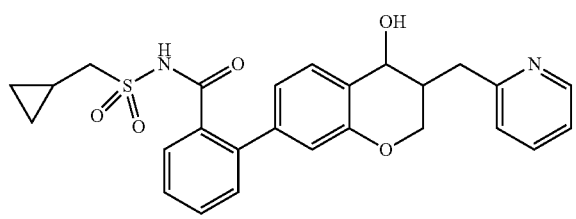 [SMILES: O=C(NS(=O)(=O)CC1CC1)c1ccccc1-c1ccc2c(c1)OCC(Cc1ccccn1)C2O]

The title compound was synthesized according to the procedure of Example 1 using (3R,4S or 3S,4R)-3-(pyridin-2-ylmethyl)-7-(4,4,5,5-tetramethyl-1,3,2-dioxaborolan-2-yl)chroman-4-ol and 2-bromo-N-((cyclopropylmethyl)sulfonyl)benzamide. MS ESI calcd. for $C_2H_{27}N_2O_5S$ [M+H]$^+$ 479, found 479.

Example 19

N-(Cyclopentylsulfonyl)-2-((3,4-trans)-4-hydroxy-3-(pyridin-2-ylmethyl)chroman-7-yl)benzamide

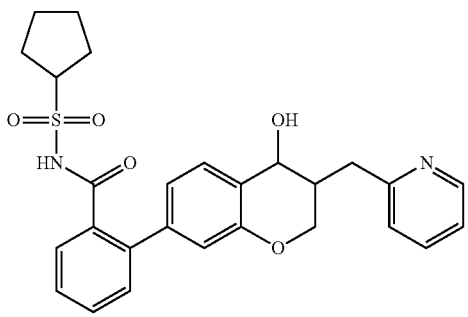 [SMILES: O=C(NS(=O)(=O)C1CCCC1)c1ccccc1-c1ccc2c(c1)OCC(Cc1ccccn1)C2O]

The title compound was synthesized according to the procedure of Example 1 using (3S,4R or 3R,4S)-3-(pyridin-2-ylmethyl)-7-(4,4,5,5-tetramethyl-1,3,2-dioxaborolan-2-yl)chroman-4-ol and 2-bromo-N-(cyclopentylsulfonyl)benzamide. MS ESI calcd. for $C_{27}H_{29}N_2O_5S$ [M+H]$^+$ 493, found 493.

Example 20

2-((3,4-trans)-4-Hydroxy-3-(pyridin-2-ylmethyl)chroman-7-yl)-N-(neopentylsulfonyl)benzamide

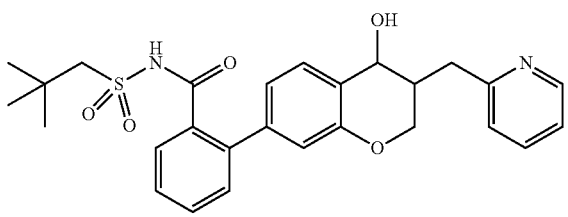 [SMILES: CC(C)(C)CS(=O)(=O)NC(=O)c1ccccc1-c1ccc2c(c1)OCC(Cc1ccccn1)C2O]

The title compound was synthesized according to the procedure of Example 1 using (3S,4R or 3R,4S)-3-(pyridin-2-ylmethyl)-7-(4,4,5,5-tetramethyl-1,3,2-dioxaborolan-2-yl)chroman-4-ol and 2-bromo-N-(neopentylsulfonyl)benzamide. MS ESI calcd. for $C_{27}H_{31}N_2O_5S$ [M+H]$^+$ 495, found 495.

Example 21

2-((3R,4S or 3S,4R)-3-Benzyl-4-hydroxychroman-7-yl)-N-((1-methylcyclopropyl)sulfonyl)benzamide

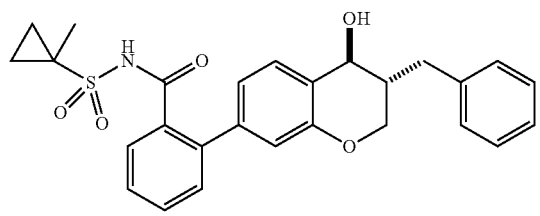 [SMILES: CC1(S(=O)(=O)NC(=O)c2ccccc2-c2ccc3c(c2)OC[C@@H](Cc2ccccc2)[C@@H]3O)CC1]

The title compound was synthesized according to the procedure of Example 1 by the Suzuki coupling of 2-bromo-N-((1-methylcyclopropyl)sulfonyl)benzamide and (3R,4S or 3S,4R)-3-benzyl-7-(4,4,5,5-tetramethyl-1,3,2-dioxaborolan-2-yl)chroman-4-ol derived from benzaldehyde and. MS ESI calcd. for $C_{27}H_{26}NO_5S$ [M−H]$^-$ 476, found 476.

Example 22

2-((3S,4R or 3R,4S)-3-Benzyl-4-hydroxychroman-7-yl)-N-((1-methylcyclopropyl)sulfonyl)benzamide

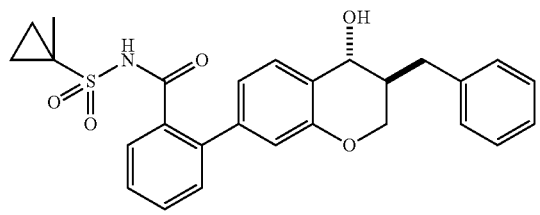 [SMILES: CC1(S(=O)(=O)NC(=O)c2ccccc2-c2ccc3c(c2)OC[C@H](Cc2ccccc2)[C@H]3O)CC1]

The title compound was synthesized according to the procedure of Example 1 by the Suzuki coupling of 2-bromo-N-((1-methylcyclopropyl)sulfonyl)benzamide and (3S,4R or 3R,4S)-3-benzyl-7-(4,4,5,5-tetramethyl-1,3,2-dioxaborolan-2-yl)chroman-4-ol derived from benzaldehyde. MS ESI calcd. for $C_{27}H_{26}NO_5S$ [M−H]$^-$ 476, found 476.

Example 23

2-((3R,4S or 3S,4R)-3-Benzyl-4-hydroxychroman-7-yl)-N-(cyclopropylsulfonyl)benzamide

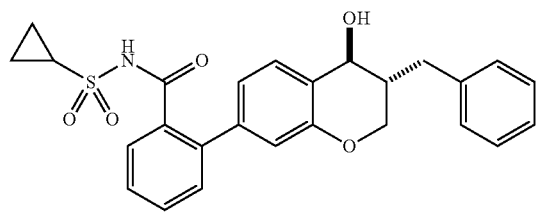 [SMILES: O=C(NS(=O)(=O)C1CC1)c1ccccc1-c1ccc2c(c1)OC[C@@H](Cc1ccccc1)[C@@H]2O]

The title compound was synthesized according to the procedure of Example 1 by the Suzuki coupling of 2-bromo-N-((1-methylcyclopropyl)sulfonyl)benzamide and (3R,4S or 3S,4R)-3-benzyl-7-(4,4,5,5-tetramethyl-1,3,2-dioxaborolan-2-yl)chroman-4-ol derived from benzaldehyde. MS ESI calcd. for $C_{26}H_{24}NO_5S$ [M−H]$^-$ 462, found 462.

Example 24

2-((3S,4R or 3R,4S)-3-Benzyl-4-hydroxychroman-7-yl)-N-(cyclopropylsulfonyl)benzamide

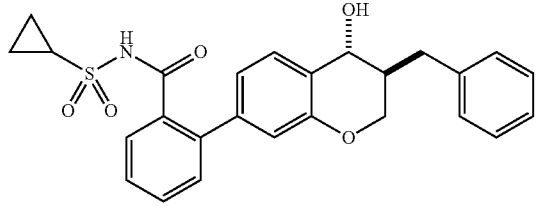 [SMILES: O=C(NS(=O)(=O)C1CC1)c1ccccc1-c1ccc2c(c1)OC[C@H](Cc1ccccc1)[C@H]2O]

The title compound was synthesized according to the procedure of Example 1 by the Suzuki coupling of 2-bromo-N-((1-methylcyclopropyl)sulfonyl)benzamide and (3S,4R or 3R,4S)-3-benzyl-7-(4,4,5,5-tetramethyl-1,3,2-dioxaborolan-2-yl)chroman-4-ol derived from benzaldehyde. MS ESI calcd. for $C_{26}H_{24}NO_5S$ [M−H]$^-$ 462, found 462.

Examples 25, 26 and 27

2-(Rac-trans)-4-Hydroxy-3-(thiazol-4-ylmethyl) chroman-7-yl)-N-((1-methylcyclopropyl)sulfonyl) benzamide (25)

2-((3R, 4S or 3S, 4R)-4-Hydroxy-3-(thiazol-4-ylmethyl)chroman-7-yl)-N-((1-methylcyclopropyl)sulfonyl)benzamide (26), and 2-((3S, 4R or 3R,4S)-4-hydroxy-3-(thiazol-4-ylmethyl)chroman-7-yl)-N-((1-methylcyclopropyl)sulfonyl)benzamide (27)

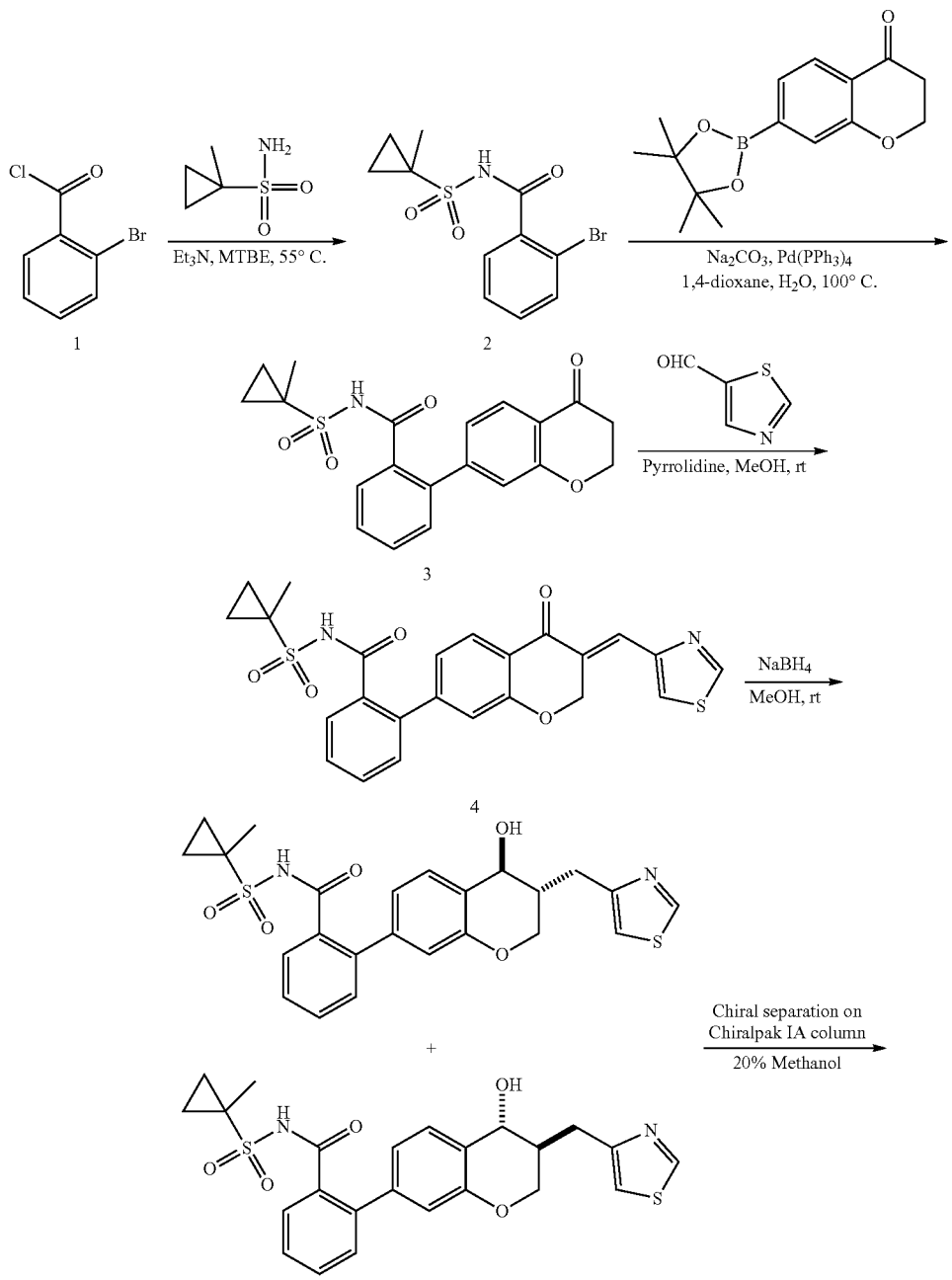

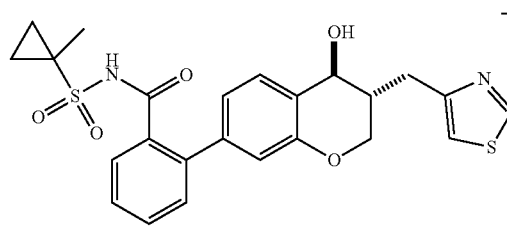 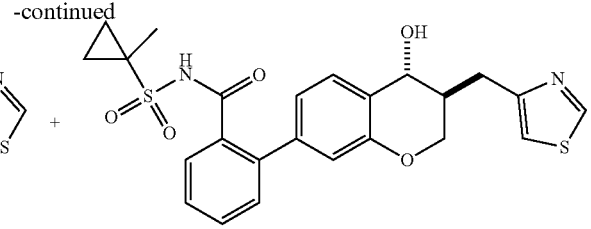

26  27

Step 1: 2-bromo-N-((1-methylcyclopropyl)sulfonyl)benzamide

2-Bromobenzoyl chloride (5.90 g, 26.88 mmol), cyclopropylmethylsulfonamide (3.60 g, 26.88 mmol), triethylamine (11.5 mL, 80.6 mmol) and MTBE (60 mL) were combined under argon atmosphere and heated to 50° C. for 24 h. Then the reaction mixture was cooled to room temperature and washed with water (30 mL). The organic layer was separated, dried over $Na_2SO_4$ and concentrated under reduced pressure. The resulting residue was purified by column chromatography on silica (0-80% EtOAc/hexanes) to afford the title compound. MS ESI calcd. for $C_{11}H_{11}BrNO_3S$ [M–H]⁻ 315, found 315.

Step 2: N-((1-methylcyclopropyl)sulfonyl)-2-(4-oxochroman-7-yl)benzamide 7-(4,4,5,5-Tetramethyl-1,3,2-dioxaborolan-2-yl)chroman-4-one (168 mg, 0.613 mmol), 2-bromo-N-((trifluoromethyl)sulfonyl)-benzamide (195 mg, 0.613 mmol), 2M $Na_2CO_3$ (0.306 mL, 0.613 mmol) and 1,4-dioxane (2 mL) were combined. The mixture was placed under an argon atmosphere by performing 2 vacuum/argon cycles. Then $Pd(PPh_3)_4$ (70.8 mg, 0.01 mmol) was added and the reaction was stirred at 100° C. for 16 h. Then the reaction mixture was diluted with water (6 mL), and extracted with ethyl acetate (10 mL×2). The combined organic layers were dried over sodium sulfate, filtered and concentrated under reduced pressure. The resulting residue was purified by column chromatography on silica (0-10% MeOH/DCM) to afford the title compound. MS ESI calcd. for $C_{20}H_{18}NO_5S$ [M–H]⁻ 384, found 384.

Step 3: (E)-N-((1-methylcyclopropyl)sulfonyl)-2-(4-oxo-3-(thiazol-4-ylmethylene)chroman-7-yl)benzamide N-((1-Methylcyclopropyl)sulfonyl)-2-(4-oxochroman-7-yl)benzamide (300 mg, 0.778 mmol), thiazole-5-carbaldehyde (88 mg, 0.778 mmol), pyrrolidine (0.064 ml, 0.778 mmol) and MeOH (4 ml) were combined, placed under an argon atmosphere and stirred for 16 hours. Then the reaction mixture was concentrated and purified by column chromatography on silica (0-10% MeOH/DCM) to afford the title compound. MS ESI calcd. for $C_{24}H_{19}N_2O_5S_2$[M–H]⁻ 479, found 479.

Step 4

(E)-N-((1-Methylcyclopropyl)sulfonyl)-2-(4-oxo-3-(thiazol-4-ylmethylene)chroman-7-yl)benzamide (290 mg, 0.601 mmol), sodium borohydride (45.5 mg, 1.202 mmol) and ethanol (3 mL) were combined. The reaction mixture was placed under nitrogen atmosphere and stirred for 3 hours. Then the reaction mixture was poured into saturated aqueous ammonium chloride (30 mL), and extracted with ethyl acetate (10 mL×2). The combined organic layers were dried over anhydrous magnesium sulfate, filtered and concentrated under reduced pressure. The resulting residue was purified by column chromatography on silica (0-70% EtOAc/hexanes) to afford 2-(rac-cis)-4-hydroxy-3-(thiazol-4-ylmethyl)chroman-7-yl)-N-((1-methylcyclopropyl)sulfonyl)benzamide as the first eluting peak (MS ESI calcd. for $C_{24}H_{25}N_2O_5S$ [M+H]⁺ 485, found 485); and 2-(rac-trans)-4-hydroxy-3-(thiazol-4-ylmethyl)chroman-7-yl)-N-((1-methylcyclopropyl)sulfonyl)benzamide 25 as the second eluting peak (MS ESI calcd. for $C_{24}H_{25}N_2O_5S$ [M+H]⁺ 485, found 485).

Step 5

2-(Rac-trans)-4-hydroxy-3-(thiazol-4-ylmethyl)chroman-7-yl)-N-((1-methylcyclopropyl)sulfonyl)-benzamide 25 (40 mg, 0.083 mmol) was separated into single enantiomers on Chiralpak IA SFC column (20% Methanol) to obtain 2-((3R,4S or 3S,4R)-4-hydroxy-3-(thiazol-4-ylmethyl)chroman-7-yl)-N-((1-methylcyclopro-pyl)sulfonyl)benzamide 26 (Enantiomer A, 1st eluting enantiomer, MS ESI calcd. for $C_{24}H_{25}N_2O_5S$ [M+H]⁺ 485, found 485, ¹H NMR (400 MHz, $CD_3OD$) δ 9.05 (d, J=2.02 Hz, 1H), 7.58-7.51 (m, 2H), 7.47-7.38 (m, 3H), 7.31 (d, J=1.9 Hz, 1H), 7.03-7.00 (dd, J=7.8 Hz, 1.7 Hz, 1H), 6.89 (d, J=1.9 Hz, 1H), 4.46 (d, J=4.5 Hz, 1H), 4.27 (dd, J=10.9 Hz, 2.6 Hz, 1H), 3.98 (dd, J=10.9, 5.1 Hz, 1H), 2.96 (dd, J=15.0 Hz, 6.9 Hz 1H), 2.82 (dd, J=14.8 Hz, 8.7 Hz 1H), 2.41 (m, 1H), 1.56-1.45 (m, 2H), 1.34 (s, 3H), 0.87-0.85 (m, 2H)); and 2-((3S,4R or 3R,4S)-4-hydroxy-3-(thiazol-4-ylmethyl)chroman-7-yl)-N-((1-methylcyclopropyl)sulfonyl)benzamide 27 (Enantiomer B, 2nd eluting enantiomer, MS ESI calcd. for $C_{24}H_{25}N_2O_5S$ [M+H]⁺ 485, found 485; ¹H NMR (400 MHz, $CD_3OD$) δ 9.04 (d, J=1.9 Hz, 1H), 7.58-7.51 (m, 3H), 7.31 (d, J=1.9 Hz, 1H), 7.02 (dd, J=7.81 Hz, 1.79 Hz, 1H), 6.88 (d, J=1.7 Hz, 1H), 4.45 (d, J=4.4 Hz, 1H), 4.27 (dd, J=11.0 Hz, 2.8 Hz, 1H), 3.99 (dd, J=11.3, 4.8 Hz, 1H), 2.95 (dd, J=14.6 Hz, 6.5 Hz 1H), 2.81 (dd, J=14.7 Hz, 8.2 Hz 1H), 2.42-2.39 (m, 1H), 1.55-1.47 (m, 2H), 1.34 (s, 3H), 0.87-0.85 (m, 2H)).

Example 28

2-(Rac-trans)-4-Hydroxy-3-((1-methyl-1H-pyrazol-5-yl)methyl)chroman-7-yl)-N-((1-methylcyclopropyl)sulfonyl)benzamide

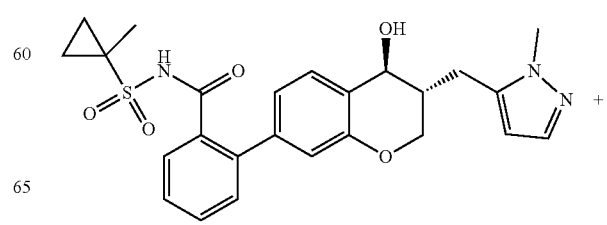

-continued

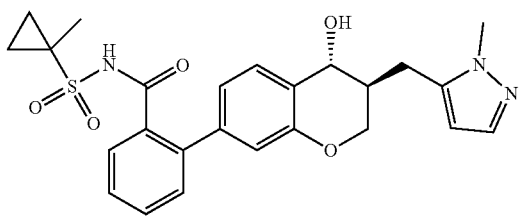

The title compounds were synthesized according to a procedure similar to the procedure for Example 25 using the appropriate starting materials. MS ESI calcd. for $C_{25}H_{26}N_3O_5S$ [M−H]$^+$ 480, found 480.

Example 29

2-((Rac-trans)-4-Hydroxy-3-((5-methyl-1,3,4-thiadiazol-2-yl)methyl)chroman-7-yl)-N-((1-methylcyclopropyl)sulfonyl)benzamide

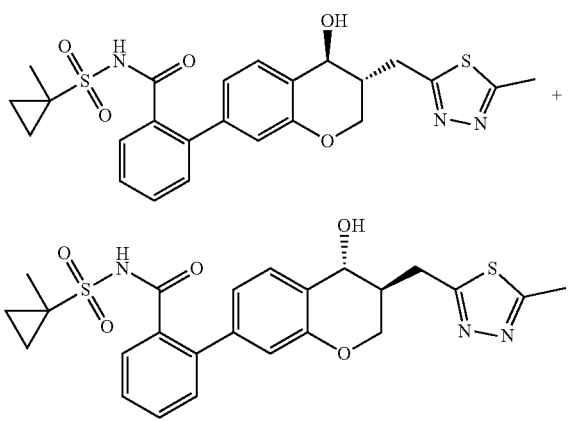

The title compounds were synthesized according to a procedure similar to the procedure for Example 25 using the appropriate starting materials. MS ESI calcd. for $C_{24}H_{24}N_3O_5S_2$ [M−H]$^-$ 498, found 498.

Example 30

2-((Rac-trans)-3-((1-ethyl-1H-pyrazol-5-yl)methyl)-4-hydroxychroman-7-yl)-N-((1-methylcyclopropyl)sulfonyl)benzamide

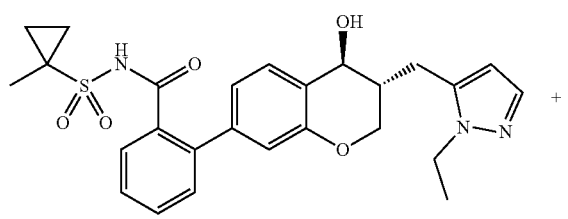

-continued

The title compounds were synthesized according to a procedure similar to the procedure for Example 25 using the appropriate starting materials. MS ESI calcd. for $C_{26}H_{30}N_3O_5S$ [M+H]$^+$ 496, found 496.

Example 31

N-(tert-Butylsulfonyl)-2-((rac-trans)-4-hydroxy-3-((5-methyl-1,3,4-thiadiazol-2-yl)methyl)chroman-7-yl)benzamide The title compounds were synthesized according to a procedure similar to the procedure for Example 25 using the appropriate starting materials. MS ESI calcd. for $C_{24}H_{26}N_3O_5S_2$ [M−H]$^-$ 500, found 500.

Example 32

N-(tert-Butylsulfonyl)-2-((rac-trans)-4-hydroxy-3-(thiazol-4-ylmethyl)chroman-7-yl)benzamide

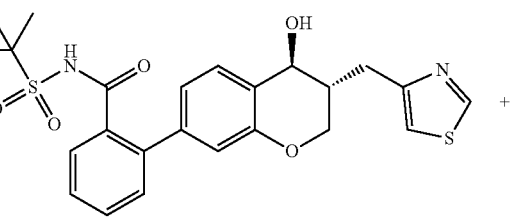

-continued

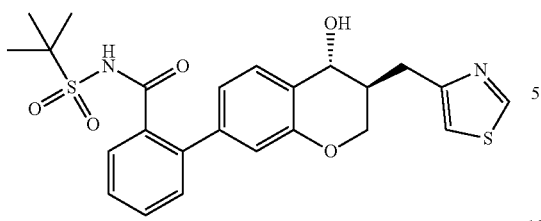

The title compounds were synthesized according to a procedure similar to the procedure for Example 25 using the appropriate starting materials. MS ESI calcd. for $C_{24}H_{25}N_2O_5S_2$ [M−H]⁻ 485, found 485.

Example 33

N-(tert-Butylsulfonyl)-2-((3R,4S or 3S,4R)-4-hydroxy-3-(thiazol-4-ylmethyl)chroman-7-yl)benzamide

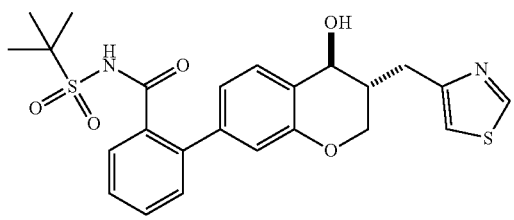 [SMILES: CC(C)(C)S(=O)(=O)NC(=O)c1ccccc1-c1ccc2c(c1)OC[C@@H](Cc1cscn1)[C@@H]2O]

The title compound was synthesized according to a procedure similar to the procedure for Example 27 using the appropriate starting materials. MS ESI calcd. for $C_{24}H_{25}N_2O_5S_2$ [M−H]⁻ 485, found 485.

Example 34

N-(tert-Butylsulfonyl)-2-((3S,4R or 3R,4S)-4-hydroxy-3-(thiazol-4-ylmethyl)chroman-7-yl)benzamide

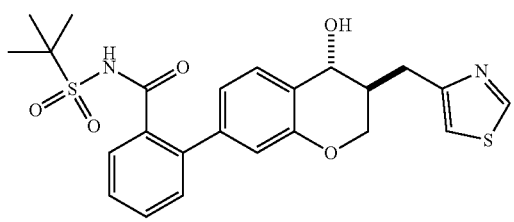 [SMILES: CC(C)(C)S(=O)(=O)NC(=O)c1ccccc1-c1ccc2c(c1)OC[C@H](Cc1cscn1)[C@H]2O]

The title compound was synthesized using a procedure similar to the procedure for Example 26. MS ESI calcd. for $C_{24}H_{25}N_2O_5S_2$ [M−H]⁻ 485, found 485.

Example 35

N-(tert-Butylsulfonyl)-2-((rac-trans)-4-hydroxy-3-((1-methyl-1H-pyrazol-5-yl)methyl)chroman-7-yl)benzamide

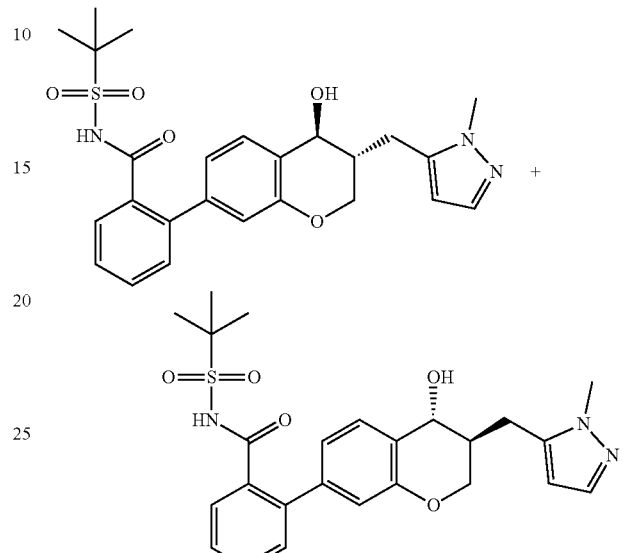

The title compounds were synthesized according to a procedure similar to the procedure for Example 25 using the appropriate starting materials. MS ESI calcd. for $C_{25}H_{30}N_3O_5S$ [M+H]⁺ 484, found 484.

Example 36

N-(tert-Butylsulfonyl)-2-((rac-trans)-3-((1-ethyl-1H-pyrazol-5-yl)methyl)-4-hydroxychroman-7-yl)benzamide

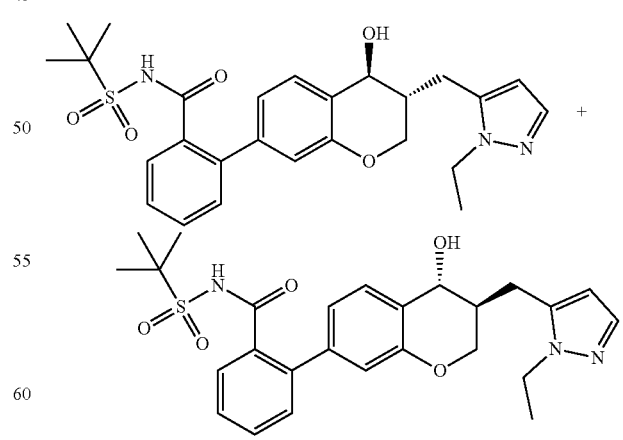

The title compounds were synthesized according to a procedure similar to the procedure for Example 25 using the appropriate starting materials. MS ESI calcd. for $C_{26}H_{30}N_3O_5S$ [M−H]⁻ 496, found 496.

Example 37

N-(tert-Butylsulfonyl)-2-((3S,4R or 3R,4S)-3-((1-ethyl-1H-pyrazol-5-yl)methyl)-4-hydroxychroman-7-yl)benzamide

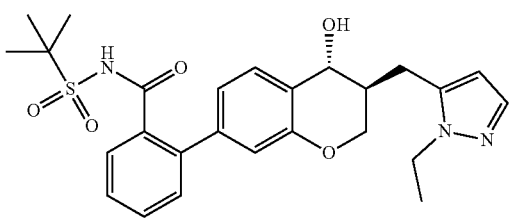 [SMILES: CCn1nccc1C[C@H]1COc2cc(-c3ccccc3C(=O)NS(=O)(=O)C(C)(C)C)ccc2[C@@H]1O]

The title compound was synthesized according to a procedure similar to the procedure for Example 27 using the appropriate starting materials. MS ESI calcd. for $C_{26}H_{30}N_3O_5S$ [M–H]⁻ 496, found 496.

Example 38

N-(tert-Butylsulfonyl)-2-((3R,4S or 3S,4R)-3-((1-ethyl-1H-pyrazol-5-yl)methyl)-4-hydroxychroman-7-yl)benzamide

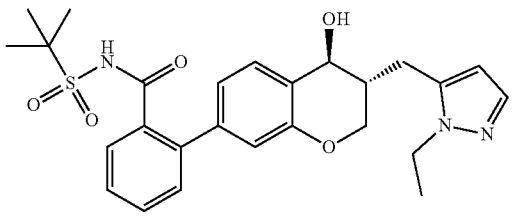 [SMILES: CCn1nccc1C[C@@H]1COc2cc(-c3ccccc3C(=O)NS(=O)(=O)C(C)(C)C)ccc2[C@H]1O]

The title compound was synthesized according to a procedure similar to the procedure for Example 26 using the appropriate starting materials. MS ESI calcd. for $C_{26}H_{30}N_3O_5S$ [M–H]⁻ 496, found 496.

Example 39

2-((Rac-cis)-3-([1,1'-Biphenyl]-4-ylmethyl)-4-hydroxychroman-7-yl)-4-fluoro-N-((trifluoromethyl)sulfonyl)benzamide

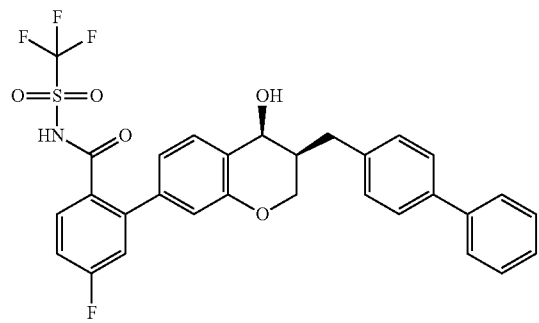

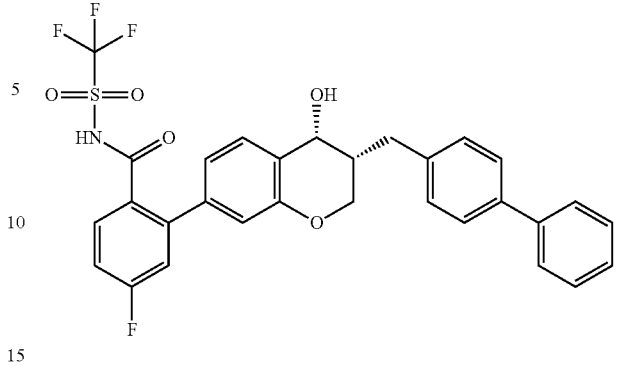

The title compounds were synthesized according to a procedure similar to the procedure for Example 25 using the appropriate starting materials. MS ESI calcd. for $C_{30}H_{22}F_4NO_5S$ [M–H]⁻ 584, found 584.

Example 40

2-((Rac-trans)-3-([1,1'-Biphenyl]-4-ylmethyl)-4-hydroxychroman-7-yl)-4-fluoro-N-((trifluoromethyl)sulfonyl)benzamide

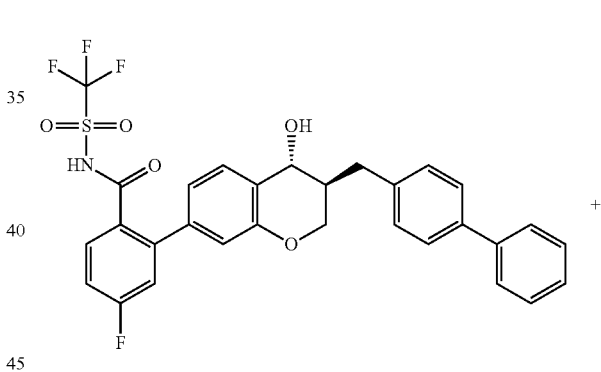

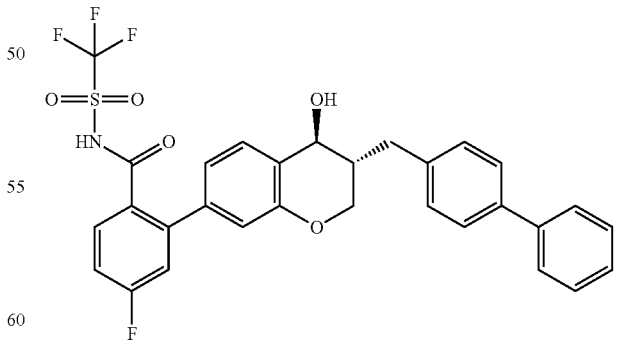

The title compounds were synthesized according to a procedure similar to the procedure for Example 25 using the appropriate starting materials. MS ESI calcd. for $C_{30}H_{22}F_4NO_5S$ [M–H]⁻ 584, found 584.

Examples 41 and 42

2-((3R,4S or 3S,4R)-3-([1,1'-Biphenyl]-4-ylmethyl)-4-hydroxychroman-7-yl)-4-fluoro-N-((trifluoromethyl)sulfonyl)benzamide 41, and 2-((3S,4R or 3R,4S)-3-([1,1'-Biphenyl]-4-ylmethyl)-4-hydroxychroman-7-yl)-4-fluoro-N-((trifluoromethyl)sulfonyl)benzamide 42

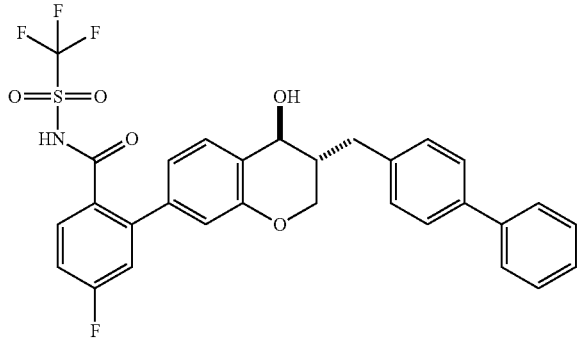

41

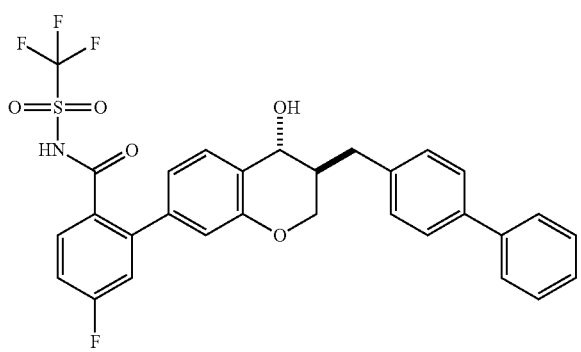

42

2-((Rac-trans)-3-([1,1'-Biphenyl]-4-ylmethyl)-4-hydroxychroman-7-yl)-4-fluoro-N-((trifluoro-methy)sulfonyl)benzamide (Example 40) was subjected to SFC chiral separation using chiralcel OD-H 21×250 (mm) with methanol +0.25% dimethyl ethyl amine and $CO_2$ as eluents to afford 2-((3R,4S or 3S,4R)-3-([1,1'-Biphenyl]-4-ylmethyl)-4-hydroxy chroman-7-yl)-4-fluoro-N-((trifluoromethyl) sulfonyl)-benzamide 41 (MS ESI calcd. for $C_{30}H_{22}F_4NO_5S$ [M+Na]$^+$ 608, found 608); and 2-((3S,4R or 3R,4S)-3-([1,1'-Biphenyl]-4-ylmethyl)-4-hydroxychroman-7-yl)-4-fluoro-N-((trifluoromethyl)sulfonyl)benzamide 42 (MS ESI calcd. for $C_{30}H_{22}F_4NO_5S$ [M+Na]$^+$ 608, found 608).

Examples 43, 44 and 45

2-(Rac-trans)-4-hydroxy-3-((2-phenyloxazol-4-yl)methy)chroman-7-yl)-N-((1-methylcyclopropyl)sulfonyl)benzamide 43

2-((3R,4S or 3S,4R)-4-Hydroxy-3-((2-phenyloxazol-4-yl)methy)chroman-7-yl)-N-((1-methylcyclopropyl)sulfonyl)benzamide 44, and 2-((3S,4R or 3R,4S)-4-hydroxy-3-((2-phenyloxazol-4-yl)methy)chroman-7-yl)-N-((1-methylcyclopropyl)sulfonyl)benzamide 45

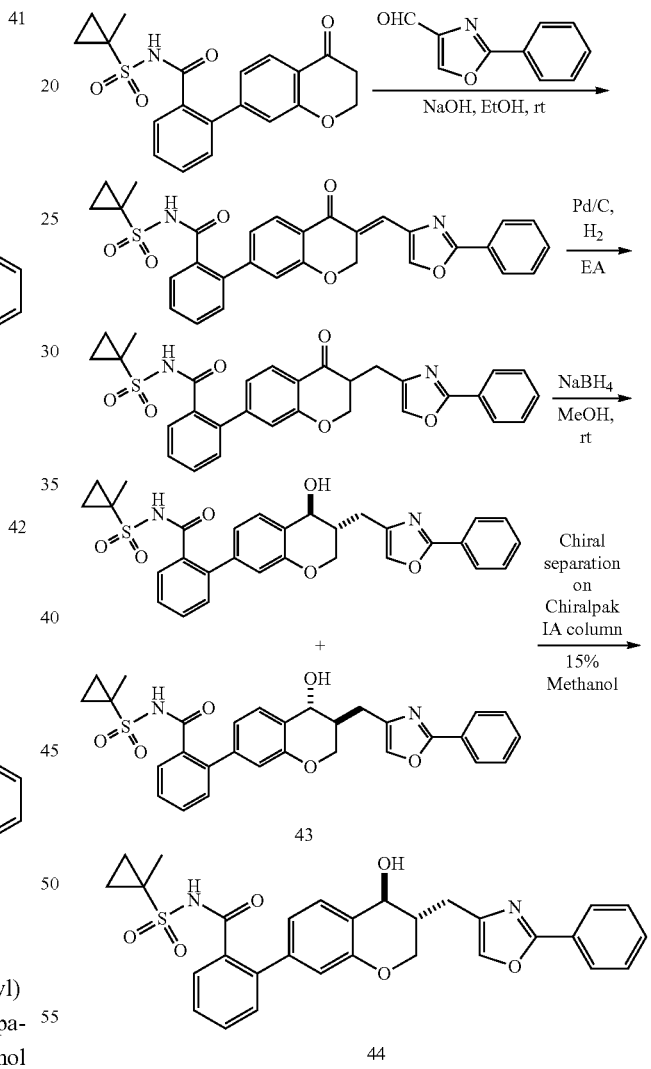

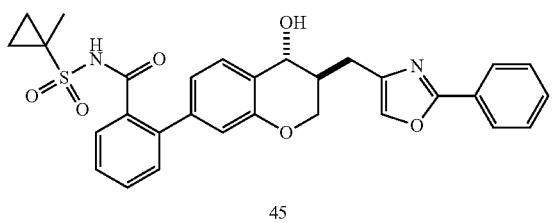

45

Step 1: (E)-N-((1-methylcyclopropyl)sulfonyl)-2-(4-oxo-3-((2-phenyloxazol-4-yl)methylene)chroman-7-yl)benzamide N-((1-Methylcyclopropyl)sulfonyl)-2-(4-oxochroman-7-yl)benzamide (300 mg, 0.778 mmol), 2-phenyloxazole-4-carbaldehyde (202 mg, 1.168 mmol), 2M NaOH (0.973 ml, 1.946 mmol) and EtOH (6 ml) were combined and stirred for 16 hours. Then the reaction mixture was concentrated, washed with water (10 mL) and extracted with ethyl acetate (10 mL×2), and purified by column chromatography on silica (0-10% MeOH/DCM) to afford the title compound. MS ESI calcd. for $C_{30}H_{23}N_2O_6S$ [M−H]$^-$ 539, found 539.

Step 2: N-((1-methylcyclopropyl)sulfonyl)-2-(4-oxo-3-((2-phenyloxazol-4-yl)methy)chroman-7-yl)benzamide (E)-N-((1-methylcyclopropyl)sulfonyl)-2-(4-oxo-3-((2-phenyloxazol-4-yl)methylene)-chroman-7-yl)benzamide (300 mg, 0.555 mmol), 10% palladium on carbon (5.9 mg, 0.055 mmol) and degassed ethyl acetate (4 mL) were combined. The mixture was placed under a hydrogen atmosphere, and 2 vacuum/hydrogen cycles were performed. The reaction mixture was stirred for 30 minutes under a hydrogen atmosphere (balloon). Then the reaction mixture was diluted with ethyl acetate, filtered through Celite™, and the filtrate was concentrated under reduced pressure. The resulting residue was purified by column chromatography on silica (0-10% MeOH/DCM) to afford the title compound. MS ESI calcd. for $C_{30}H_{25}N_2O_6S$ [M−H]$^+$ 541, found 541.

Step 3

2-(Rac-trans)-4-hydroxy-3-((2-phenyloxazol-4-yl)methy)chroman-7-yl)-N-((1-methylcyclopropyl)sulfonyl)benzamide 43 was synthesized using a NaBH$_4$ reduction procedure similar to the procedure described in Example 25, Step 4. MS ESI calcd. for $C_{30}H_{27}N_2O_6S$ [M−H]$^-$ 543, found 543.

Step 4

2-(Rac-trans)-4-hydroxy-3-((2-phenyloxazol-4-yl)methy)chroman-7-yl)-N-((1-methylcyclopropyl)-sulfonyl)benzamide 45 (50 mg, 0.092 mmol) was separated into single enantiomers on Chiralpak IA SFC column (15% Methanol) to obtain 2-((3R,4S or 3S,4R)-4-hydroxy-3-((2-phenyloxazol-4-yl)methy)chroman-7-yl)-N-((1-methylcyclopropyl)sulfonyl)benzamide 44 (Enantiomer A, 1$^{st}$ eluting enantiomer; MS ESI calcd. for $C_{30}H_{29}N_2O_6S$ [M+H]$^+$ 545, found 545. $^1$H NMR (400 MHz, CD$_3$OD) δ 8.02-8.01 (m, 2H), 7.74 (s, 1H), 7.58-7.40 (m, 8H), 7.02 (dd, J=7.9 Hz, 2.0 Hz, 1H), 6.91 (d, J=1.67 Hz, 1H), 4.55 (d, J=4.3 Hz, 1H), 4.34 (dd, J=11.0 Hz, 2.9 Hz, 1H), 4.10 (dd, J=10.8, 4.5 Hz, 1H), 2.71 (dd, J=15.4 Hz, 6.7 Hz 1H), 2.59 (dd, J=14.8 Hz, 8.8 Hz 1H), 2.39-2.36 (m, 1H), 1.57-1.47 (m, 2H), 1.34 (s, 3H), 0.87-0.85 (m, 2H); and 2-((3S,4R or 3R,4S)-4-hydroxy-3-((2-phenyloxazol-4-yl)methy)chroman-7-yl)-N-((1-methylcyclopropyl)sulfonyl)-benzamide 45 (Enantiomer B, 2$^{nd}$ eluting enantiomer; MS ESI calcd. for $C_{30}H_{29}N_2O_6S$ [M+H]$^+$ 545, found 545; $^1$H NMR (400 MHz, CD$_3$OD) δ 8.02-8.01 (m, 2H), 7.74 (s, 1H), 7.58-7.40 (m, 8H), 7.03-7.01 (dd, J=7.9 Hz, 2.0 Hz, 1H), 6.90 (d, J=1.67 Hz, 1H), 4.53 (d, J=4.3 Hz, 1H), 4.35 (dd, J=11.0 Hz, 2.9 Hz, 1H), 4.09 (dd, J=10.8, 4.5 Hz, 1H), 2.71 (dd, J=15.4 Hz, 6.7 Hz 1H), 2.58 (dd, J=14.8 Hz, 8.8 Hz 1H), 2.39-2.37 (m, 1H), 1.57-1.47 (m, 2H), 1.34 (s, 3H), 0.87-0.85 (m, 2H)).

Example 46

2-(Rac-trans)-4-Hydroxy-3-((2-phenyloxazol-4-yl)methyl)chroman-7-yl)-N-((1-methylcyclopropyl)sulfonyl)benzamide

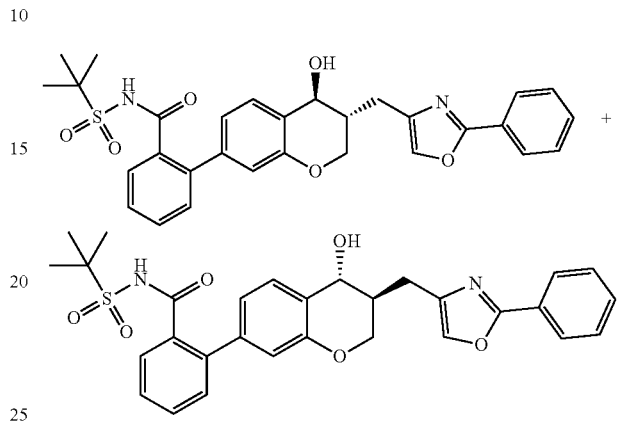

The title compounds were synthesized according to a procedure similar to the procedure for Example 43 using the appropriate starting materials. ESI calcd. for $C_{30}H_{29}N_2O_6S$ [M−H]$^+$ 545, found 545.

Example 47

N-(tert-Butylsulfonyl)-2-((3R,4S or 3S,4R)-4-hydroxy-3-((2-phenyloxazol-4-yl)methyl)chroman-7-yl)benzamide

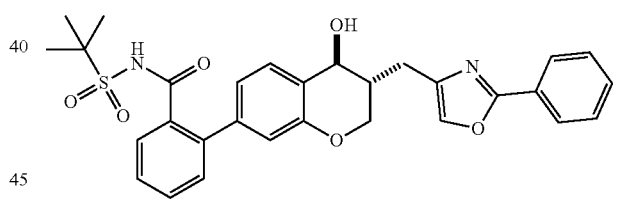

The title compound was synthesized according to a procedure similar to the procedure for Example 44 using the appropriate starting materials. ESI calcd. for $C_{30}H_{29}N_2O_6S$ [M−H]$^+$ 545, found 545.

Example 48

N-(tert-Butylsulfonyl)-2-((3S,4R or 3R,4S)-4-hydroxy-3-((2-phenyloxazol-4-yl)methyl)chroman-7-yl)benzamide

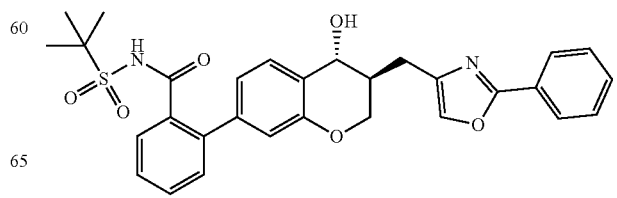

The title compound was synthesized according to a procedure similar to the procedure for Example 45 using the appropriate starting materials. ESI calcd. for $C_{30}H_{29}N_2O_6S$ [M−H]+ 545, found 545.

Examples 49 and 50

2-((3,4-trans)-4-Hydroxy-3-((R)-1-(pyridin-2-yl)ethyl)chroman-7-yl)-N-((1-methylcyclopropyl)sulfonyl)benzamide 49, and 2-((3,4-trans)-4-Hydroxy-3-((S)-1-(pyridin-2-yl)ethyl)chroman-7-yl)-N-((1-methylcyclopropyl)sulfonyl)benzamide 50

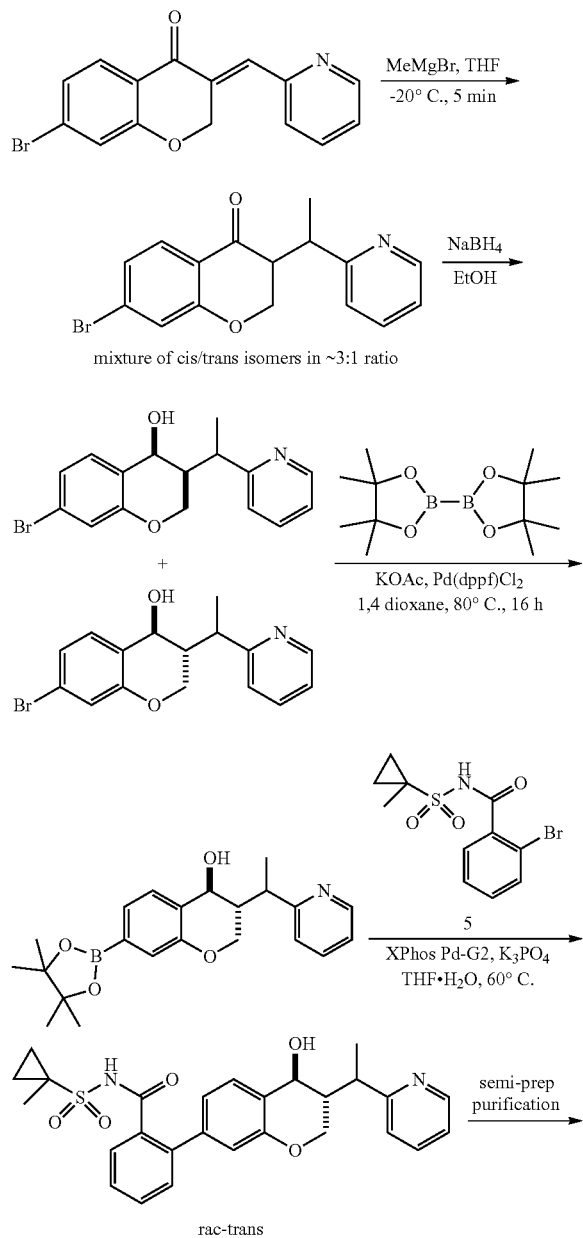

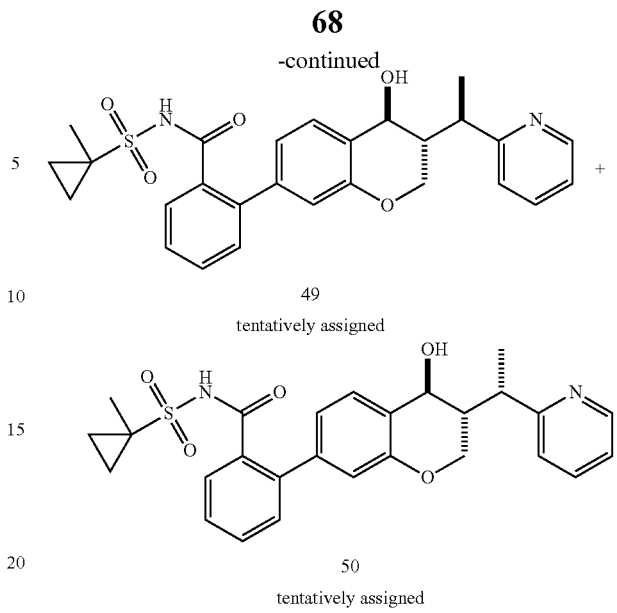

49
tentatively assigned 50
tentatively assigned

Step 1: 7-bromo-3-(1-(pyridin-2-yl)ethyl)chroman-4-one (E)-7-Bromo-3-(pyridin-2-ylmethylene)chroman-4-one (2.00 g, 6.33 mmol) in THF (8 mL) was cooled to −20° C., then methyl magnesium bromide (1.50 g, 12.65 mmol) was added dropwise. The reaction was stirred for 5 minutes, then quenched by adding brine (10 ml) and extracted with EtOAc (2×10 mL). The combined organic layers were dried over sodium sulfate, and concentrated. The resulting crude residue was purified on silica by combi-flash (EtOAc/n-hexanes: 20-40%) to obtain the title compound as mixture of cis/trans isomer in ~3:1 ratio. MS ESI calcd. for $C_{16}H_{13}BrNO_2$ [M−H]− 330, found 330.

Step 2: 7-bromo-3-(1-(pyridin-2-yl)ethyl)chroman-4-ol 7-bromo-3-(1-(pyridin-2-yl)ethyl)chroman-4-one (1.2 g, 3.61 mmol) was dissolved in MeOH (10 ml) and cooled to 0° C. Then sodium tetrahydroborate (0.342 g, 9.03 mmol) was added and the reaction was allowed to warm to room temperature. After 1 hour, reaction mixture was concentrated, diluted with water (10 mL)/saturated $Na_2SO_4$ (5 ml) and extracted with EtOAc (2×10 mL). The combined organic layers were dried over sodium sulfate, and concentrated. The resulting residue was purified on reverse phase column (C18 RediSep gold column, acetonitrile/water: 10-50%) to afford (rac-cis)-7-bromo-3-(1-(pyridin-2-yl)ethyl)chroman-4-ol as the first eluting peak as single stereoisomer [(+−) cis-syn or (+−) cis-anti] (MS ESI calcd. for $C_{16}H_{15}BrNO_2$ [M−H]− 332, found 332); and (rac-trans)-7-bromo-3-(1-(pyridin-2-yl)ethyl)chroman-4-ol as the second eluting peak as a mixture of (+−) trans-syn and (+−) trans-anti in ~4:1 (MS ESI calcd. for $C_{16}H_{15}BrNO_2$ [M−H]− 332, found 332).

Step 3: (rac-trans)-3-(1-(pyridin-2-yl)ethyl)-7-(4,4,5,5-tetramethyl-1,3,2-dioxaborolan-2-yl)chroman-4-ol (Rac-trans)-7-bromo-3-(1-(pyridin-2-yl)ethyl)chroman-4-ol [(490 mg, 1.46 mmol); mixture of (+−) trans-syn and (+−) trans-anti in ~4:1 ratio], 4,4,4',4',5,5,5',5'-octamethyl-2,2'-bi(1,3,2-dioxaborolane) (484 mg, 1.90 mmol), potassium acetate (432 mg, 4.4 mmol) and degassed 1,4-dioxane (15 mL) were combined. The reaction mixture was placed under an argon atmosphere, and 2 vacuum/argon cycles were performed. Then 1, 1'-bis (diphenylphosphino) ferrocene-palladium (II) dichloride dichloromethane complex (215 mg, 0.293 mmol) was added and the reaction was stirred at 80° C. for 16 h. Then the reaction mixture was filtered through Celite™ and the filtrate was concentrated under reduced pressure. The resulting residue was purified by column chromatography on silica (0-70% EtOAc/hexanes) to afford the title compound as mixture of (+−) trans-syn and (+−) trans-anti in ~4:1 ratio. MS ESI calcd. For $C_{22}H_{27}BNO_4$ $[M-H]^+$ 380 and found 380.

Step 4

(Rac-trans)-3-(1-(pyridin-2-yl)ethyl)-7-(4,4,5,5-tetramethyl-1,3,2-dioxaborolan-2-yl)chroman-4-ol. [(217 mg, 0.570 mmol; mixture of (+−) trans-syn and (+−) trans-anti in ~4:1 ratio], 2-bromo-N-((1-methylcyclopropyl)sulfonyl)benzamide (165 mg, 0.519 mmol), potassium phosphate tribasic (330 mg, 1.556 mmol), THF (8 mL) and water (1 mL) were combined. The mixture was placed under an argon atmosphere by performing 2 vacuum/argon cycles. Then $2^{nd}$ generation Xphos precatalyst (40.8 mg, 0.052 mmol) was added and the reaction was stirred at 60° C. for 16 h. Then the reaction mixture was diluted with water (6 mL), extracted with ethyl acetate (10 mL×2), dried over sodium sulfate, filtered and concentrated under reduced pressure. The resulting residue was purified by column chromatography on silica (0-10% MeOH/DCM), followed by semi-prep HPLC HPLC (Luna 5u C18(2) 100 A Column 250 mm×4.60 mm, acetonitrile/water: 10-50%, 0.1% TFA) to obtain $1^{st}$ eluted peak [pair of enantiomers of either (+−) trans-syn or (+−) trans-anti] 2-4-hydroxy-3-(1-(pyridin-2-yl)ethyl)chroman-7-yl)-N-((1-methylcyclopropyl)-sulfonyl)benzamide ($C_{27}H_{27}N_2O_5S$ $[M-H]^-$ 491, found 491; $^1H$ NMR (400 MHz, $CD_3OD$) δ 8.65-8.62 (m, 1H), 8.37-8.33 (m, 1H), 7.93-7.90 (m, 1H), 7.79-7.75 (m, 1H), 7.59-7.38 (m, 5H), 7.05-6.98 (m, 1H), 6.87-6.80 (m, 1H), 4.92-4.87 (m, 1H), 4.27 (dd, J=11.6 Hz, 2.1 Hz, 1H), 3.76-3.72 (m, 1H), 3.14-3.07 (m, 1H), 2.36-2.32 (m, 1H), 1.59-1.51 (m, 5H), 1.44-1.34 (m, 3H), 0.93-0.84 (m, 2H)); and $2^{nd}$ eluted peak [pair of enantiomers of either (+−) trans-anti or (+−) trans-syn] 2-((3R,4S or 3S,4R)-4-hydroxy-3-((S)-1-(pyridin-2-yl)ethyl)chroman-7-yl)-N-((1-methylcyclopropyl)sulfonyl)benzamide ($C_{27}H_{27}N_2O_5S$ $[M-H]^-$ 491, found 491; $^1H$ NMR (400 MHz, $CD_3OD$) δ 8.6 (d, J=5.0 Hz 1H), 8.36 (s, 1H), 7.93 (s, 1H), 7.76 (s, 1H), 7.57-7.38 (m, 5H), 7.02-6.99 (dd, J=7.77 Hz, 1.75 Hz, 1H), 6.81 (d, J=1.55 Hz, 1H), 4.92 (s, 1H), 4.10-4.04 (t, J=10.7 Hz, 1H), 3.65 (d, J=10.3 Hz, 1H), 3.42-3.38 (m, 1H), 2.44-2.37 (m, 1H), 1.59-1.58 (m, 3H), 1.55-1.50 (m, 2H), 1.34 (s, 3H), 0.87-0.85 (m, 2H)).

Example of a Pharmaceutical Composition

As a specific embodiment of an oral pharmaceutical composition, a 100 mg potency tablet is composed of 100 mg of any one of the examples, 268 mg microcrystalline cellulose, 20 mg of croscarmellose sodium, and 4 mg of magnesium stearate. The active, microcrystalline cellulose, and croscarmellose are blended first. The mixture is then lubricated by magnesium stearate and pressed into tablets.

Biological Assay

BLT-1 cAMP Assay

The ability of compounds to antagonize the human BLT1 receptor was determined using a kit to measure changes in intracellular cyclic AMP levels (cAMP dynamic assay kit, Cisbio Cat. No. 62AM4PEC). HEK293 cells recombinantly expressing human BLT1 receptor, previously frozen in Recovery Medium (Life Technologies, Cat. No. 12648-010) were thawed and diluted into assay medium (HBSS (Hyclone SH 30268.01), 20 mM HEPES (Gibco 15630-106), 800 μM IBMX (Sigma I5879), 0.1% DTPA BSA (Perkin Elmer CR84-100)). The cell suspension was centrifuged at 200×g for 10 min and then resuspended in fresh assay medium to a density of $2.5×10^5$ cells/mL. A Labcyte Echo 550 acoustic dispenser was used to transfer 25 nL of test compound dissolved in DMSO into the wells of a dry 384-well plate (Greiner 784075). All subsequent liquid additions were performed using a BIORAPTR (FRD; Beckman Coulter). Next, 5 μL of cell suspension was added and incubated for 20 min. at 37° C. and 5% $CO_2$ in a humidified plastic tray. To test for agonist activity 51 μL of assay buffer containing forskolin (Sigma F-6886. 4 μM for BLT1) was added and incubated for 30 minutes at 37° C. and 5% $CO_2$ in a humidified plastic tray. To test for antagonist activity 5 μL of assay buffer containing forskolin (Sigma F-6886. 4 μM for BLT1) and either $LTB_4$ (Sigma Aldrich L0517; 2 nM BLT1) was added and incubated for 30 minutes at 37° C. and 5% $CO_2$ in a humidified plastic tray.

The levels of cAMP were detected using the CisBio kit following the manufacturer's instructions: cAMP-d2 vial was reconstituted with distilled water and then diluted accordingly with conjugate & lysis buffer. 5 μL of cAMP-d2 working solution was added to all of the wells of the assay plate. cAMP-Cryptate vial was reconstituted with distilled water and then diluted accordingly with conjugate & lysis buffer. 5 μL of cAMP-Cryptate working solution were added to the assay plate. The assay plate was shaken for 3 minutes and incubated at room temperature for 45 minutes, then read on Perkin Elmer Envision. cAMP standard curve and fit data were plotted using a 4 parameter dose response curve fitting algorithm to fit curve. A 4-parameter curve fit (Max, min, log EC50 and slope) was used to transform fluorescent 665 nm/615 nm ratio signal to cAMP concentration. After normalization to treated and untreated controls, the percent effect of signal at each compound concentration was calculated. The plot of percent effect versus the log of compound concentration was fit with a 4-parameter concentration response equation to calculate $EC_{50}$ values. Compound concentrations tested were 10 000, 3 333, 1 111, 370.4, 123.4, 41.2, 13.7, 4.6, 1.5 and 0.5 nM with 0.25% residual DMSO.

The compounds of the present invention, including the compounds in Examples 1-50, have $EC_{50}$ values less than ≤5000 nanomolar (nM) in the BLT-1 cAMP Assay described above. Specific $EC_{50}$ values in the BLT-1 cAMP Assay are shown in Table I.

TABLE I

| Example Number | $EC_{50}$ (nM) BLT-1 cAMP Assay |
|---|---|
| 1 | 650 |
| 2 | 6 |
| 3 | 1717 |
| 4 | 93 |
| 5 | 2171 |
| 6 | 28 |
| 7 | 1266 |
| 8 | 22 |
| 9 | 4 |
| 10 | 870 |
| 11 | 144 |
| 12 | 17 |
| 13 | 441 |
| 14 | 2 |
| 15 | 480 |
| 16 | 4 |
| 17 | 24 |
| 18 | 23 |
| 19 | 48 |
| 20 | 44 |
| 21 | 2037 |
| 22 | 15 |
| 23 | 2818 |
| 24 | 17 |
| 25 | 16 |
| 26 | 770 |
| 27 | 26 |
| 28 | 360 |
| 29 | 740 |
| 30 | 538 |
| 31 | 556 |
| 32 | 11 |
| 33 | 808 |
| 34 | 9 |
| 35 | 95 |
| 36 | 81 |
| 37 | 36 |
| 38 | 1162 |
| 39 | 37 |
| 40 | 9 |
| 41 | 11 |
| 42 | 35 |
| 43 | 19 |
| 44 | 60 |
| 45 | 3 |
| 46 | 15 |
| 47 | 75 |
| 48 | 5 |
| 49 | 154 |
| 50 | 67 |

While the invention has been described and illustrated with reference to certain particular embodiments thereof, those skilled in the art will appreciate that various adaptations, changes, modifications, substitutions, deletions, or additions of procedures and protocols may be made without departing from the scope of the invention. For example, effective dosages other than the particular dosages as set forth herein above may be applicable as a consequence of variations in responsiveness of the mammal being treated for any of the indications with the compounds of the invention indicated above. The specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention.

What is claimed is:

1. A compound of structural formula I:

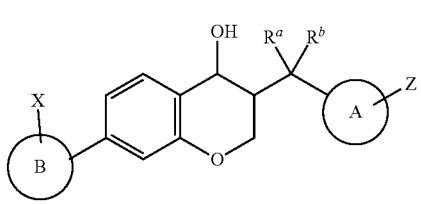

or a pharmaceutically acceptable salt thereof; wherein

A is heteroaryl, wherein heteroaryl is unsubstituted or substituted with 1-3 substituents independently selected from $C_{1-6}$alkyl and halogen;

B is selected from the group consisting of:
(1) aryl, and
(2) heteroaryl,
wherein aryl and heteroaryl are unsubstituted or substituted with 1-4 substituents independently selected from $C_{1-6}$alkyl and halogen;

X is selected from the group consisting of:
(1) —C(O)NHSO$_2$CF$_3$,
(2) —C(O)NHSO$_2$CH$_2$CF$_3$,
(3) —C(O)NHSO$_2$CHF$_2$,
(4) —C(O)NHSO$_2$C$_{1-6}$alkyl,
(5) —C(O)NHSO$_2$CH$_2$C$_{3-6}$cycloalkyl, and
(6) —C(O)NHSO$_2$C$_{3-6}$cycloalkyl,
wherein alkyl and cycloalkyl are unsubstituted or substituted with 1-3 substituents independently selected from $C_{1-6}$alkyl;

Z is selected from the group consisting of:
(1) hydrogen,
(2) —C$_{1-6}$alkyl, and
(3) phenyl,
wherein alkyl and phenyl are unsubstituted or substituted with 1-4 substituents independently selected from $C_{1-6}$alkyl;

$R^a$ is selected from the group consisting of:
(1) hydrogen,
(2) halogen, and
(3) $C_{1-6}$alkyl; and $R^b$ is selected from the group consisting of:
(1) hydrogen,
(2) halogen, and
(3) $C_{1-6}$alkyl.

2. The compound according to claim 1 wherein X is selected from the group consisting of:
(1) —C(O)NHSO$_2$CH$_2$CF$_3$,
(2) —C(O)NHSO$_2$CHF$_2$,
(3) —C(O)NHSO$_2$C$_{1-6}$alkyl,
(4) —C(O)NHSO$_2$CH$_2$C$_{3-6}$cycloalkyl, and
(5) —C(O)NHSO$_2$C$_{3-6}$cycloalkyl,
wherein alkyl and cycloalkyl are unsubstituted or substituted with 1-3 substituents independently selected from $C_{1-6}$alkyl;
or a pharmaceutically acceptable salt thereof.

3. The compound according to claim 1 wherein X is selected from the group consisting of:
(1) —C(O)NHSO$_2$CF$_3$,
(2) —C(O)NHSO$_2$C$_{1-6}$alkyl,
(3) —C(O)NHSO$_2$CH$_2$C$_{3-6}$cycloalkyl, and
(4) —C(O)NHSO$_2$C$_{3-6}$cycloalkyl,
wherein alkyl and cycloalkyl are unsubstituted or substituted with 1-3 substituents independently selected from C$_{1-6}$alkyl; or a pharmaceutically acceptable salt thereof.

4. The compound according to claim 1 wherein X is selected from the group consisting of:
(1) —C(O)NHSO$_2$C$_{1-6}$alkyl, and
(2) —C(O)NHSO$_2$C$_{3-6}$cycloalkyl,
wherein alkyl and cycloalkyl are unsubstituted or substituted with 1-3 substituents independently selected from C$_{1-6}$alkyl; or a pharmaceutically acceptable salt thereof.

5. The compound according to claim 1 wherein Z is phenyl, wherein phenyl is unsubstituted or substituted with 1-4 substituents independently selected from C$_{1-6}$alkyl; or a pharmaceutically acceptable salt thereof.

6. The compound according to claim 1 wherein Z is hydrogen; or a pharmaceutically acceptable salt thereof.

7. The compound according to claim 1 wherein A is selected from the group consisting of: pyridine, oxazole, thiazole, thiadiazole, and pyrazole, wherein pyridine, oxazole, thiazole, thiadiazole, and pyrazole are unsubstituted or substituted with 1-3 substituents independently selected from C$_{1-6}$alkyl; or a pharmaceutically acceptable salt thereof.

8. The compound according to claim 1 wherein A is oxazole, wherein oxazole is unsubstituted or substituted with 1-3 substituents independently selected from C$_{1-6}$alkyl and halogen; or a pharmaceutically acceptable salt thereof.

9. The compound according to claim 1 wherein A is selected from the group consisting of: pyridine, thiazole, thiadiazole, and pyrazole, wherein pyridine, thiazole, thiadiazole, and pyrazole are unsubstituted or substituted with 1-3 substituents independently selected from C$_{1-6}$alkyl; or a pharmaceutically acceptable salt thereof.

10. The compound according to claim 1 wherein B is aryl, wherein aryl is unsubstituted or substituted with 1-4 substituents independently selected from C$_{1-6}$alkyl and halogen; or a pharmaceutically acceptable salt thereof.

11. The compound according to claim 1 wherein B is phenyl; or a pharmaceutically acceptable salt thereof.

12. The compound according to claim 1 wherein B is phenyl, wherein phenyl is unsubstituted or substituted with 1-4 substituents independently selected from halogen; or a pharmaceutically acceptable salt thereof.

13. The compound according to claim 1 wherein R$^a$ and R$^b$ are selected from the group consisting of: hydrogen, and C$_{1-6}$alkyl; or a pharmaceutically acceptable salt thereof.

14. The compound according to claim 1 wherein R$^a$ and R$^b$ are hydrogen; or a pharmaceutically acceptable salt thereof.

15. The compound according to claim 1 wherein
A is heteroaryl, wherein heteroaryl is unsubstituted or substituted with 1-3 substituents independently selected from C$_{1-6}$alkyl and halogen;
B is aryl, wherein aryl is unsubstituted or substituted with 1-4 substituents independently selected from C$_{1-6}$alkyl and halogen;
X is selected from the group consisting of:
(1) —C(O)NHSO$_2$CF$_3$,
(2) —C(O)NHSO$_2$C$_{1-6}$alkyl,
(3) —C(O)NHSO$_2$CH$_2$C$_{3-6}$cycloalkyl, and
(4) —C(O)NHSO$_2$C$_{3-6}$cycloalkyl,
wherein alkyl and cycloalkyl are unsubstituted or substituted with 1-3 substituents independently selected from C$_{1-6}$alkyl;
Z is selected from the group consisting of:
(1) hydrogen,
(2) —C$_{1-6}$alkyl, and
(3) phenyl,
wherein alkyl and phenyl are unsubstituted or substituted with 1-4 substituents independently selected from C$_{1-6}$alkyl; and
R$^a$ and R$^b$ are selected from the group consisting of: hydrogen, and C$_{1-6}$alkyl;
or a pharmaceutically acceptable salt thereof.

16. The compound according to claim 1 wherein
A is oxazole, wherein oxazole is unsubstituted or substituted with 1-3 substituents independently selected from C$_{1-6}$alkyl and halogen;
B is phenyl;
X is selected from the group consisting of:
(1) —C(O)NHSO$_2$C$_{1-6}$alkyl, and
(2) —C(O)NHSO$_2$C$_{3-6}$cycloalkyl,
wherein alkyl and cycloalkyl are unsubstituted or substituted with 1-3 substituents independently selected from C$_{1-6}$ alkyl;
Z is phenyl, wherein phenyl is unsubstituted or substituted with 1-4 substituents independently selected from C$_{1-6}$alkyl; and
R$^a$ and R$^b$ are hydrogen;
or a pharmaceutically acceptable salt thereof.

17. The compound according to claim 1 wherein
A is selected from the group consisting of: pyridine, thiazole, thiadiazole, and pyrazole, wherein pyridine, thiazole, thiadiazole, and pyrazole are unsubstituted or substituted with 1-3 substituents independently selected from C$_{1-6}$alkyl;
B is phenyl, wherein phenyl is unsubstituted or substituted with 1-4 substituents independently selected from halogen;
X is selected from the group consisting of:
(1) —C(O)NHSO$_2$CF$_3$,
(2) —C(O)NHSO$_2$C$_{1-6}$alkyl,
(3) —C(O)NHSO$_2$CH$_2$C$_{3-6}$cycloalkyl, and
(4) —C(O)NHSO$_2$C$_{3-6}$cycloalkyl,
wherein alkyl and cycloalkyl are unsubstituted or substituted with 1-3 substituents independently selected from C$_{1-6}$ alkyl;
Z is hydrogen; and
R$^a$ and R$^b$ are selected from the group consisting of: hydrogen, and C$_{1-6}$alkyl;
or a pharmaceutically acceptable salt thereof.

18. A compound from:
(1) 4-Fluoro-2-((3S,4R)-4-hydroxy-3-(pyridin-2-ylmethyl)chroman-7-yl)-N-((trifluoro-methyl)sulfonyl)benzamide;
(2) 4-Fluoro-2-((3R,4S)-4-hydroxy-3-(pyridin-2-ylmethyl)chroman-7-yl)-N-((trifluoro-methyl)sulfonyl)benzamide;
(3) 4-Fluoro-2-((3S,4R)-4-hydroxy-3-(pyridin-2-ylmethyl)chroman-7-yl)-N-(methyl-sulfonyl)benzamide;
(4) 4-Fluoro-2-(3R,4S)-4-hydroxy-3-(pyridin-2-ylmethyl)chroman-7-yl)-N-(methyl-sulfonyl)benzamide;
(5) N-(Cyclopropylsulfonyl)-2-((3S,4R)-4-hydroxy-3-(pyridin-2-ylmethyl)chroman-7-yl)benzamide;
(6) N-(Cyclopropylsulfonyl)-2-(3R,4S)-4-hydroxy-3-(pyridin-2-ylmethyl)chroman-7-yl)benzamide;

(7) 2-((3S,4R)-4-Hydroxy-3-(pyridin-2-ylmethyl)chroman-7-yl)-N-((1-methylcyclo-propyl)sulfonyl)benzamide;
(8) 2-((3R,4S)-4-Hydroxy-3-(pyridin-2-ylmethyl)chroman-7-yl)-N-((1-methylcyclo-propyl)sulfonyl)benzamide;
(9) 4-Fluoro-2-((3S,4R)-4-hydroxy-3-(pyridin-2-ylmethyl)chroman-7-yl)-N-((1-methyl-cyclopropyl)sulfonyl)benzamide;
(10) 4-Fluoro-2-((3R,4S)-4-hydroxy-3-(pyridin-2-ylmethyl)chroman-7-yl)-N-((1-methyl-cyclopropyl)sulfonyl)benzamide;
(11) N-(tert-Butylsulfonyl)-2-((3S,4R)-4-hydroxy-3-(pyridin-2-ylmethyl)chroman-7-yl)benzamide;
(12) N-(tert-Butylsulfonyl)-2-((3R,4S)-4-hydroxy-3-(pyridin-2-ylmethyl)chroman-7-yl)benzamide;
(13) N-(tert-Butylsulfonyl)-4-fluoro-2-((3S,4R)-4-hydroxy-3-(pyridin-2-ylmethyl)chroman-7-yl)benzamide;
(14) N-(tert-Butylsulfonyl)-4-fluoro-2-(3R,4S)-4-hydroxy-3-(pyridin-2-ylmethyl)chroman-7-yl)benzamide;
(15) N-(Cyclopropylsulfonyl)-4-fluoro-2-((3S,4R)-4-hydroxy-3-(pyridin-2-ylmethyl)chroman-7-yl)benzamide;
(16) N-(Cyclopropylsulfonyl)-4-fluoro-2-(3R,4S)-4-hydroxy-3-(pyridin-2-ylmethyl)chroman-7-yl)benzamide;
(17) 2-((3,4-trans)-4-Hydroxy-3-(pyridin-2-ylmethyl)chroman-7-yl)-N-(isobutylsulfonyl)-benzamide;
(18) N-((Cyclopropylmethyl)sulfonyl)-2-((3,4-trans)-4-hydroxy-3-(pyridin-2-ylmethyl)-chroman-7-yl)benzamide;
(19) N-(Cyclopentylsulfonyl)-2-((3,4-trans)-4-hydroxy-3-(pyridin-2-ylmethyl)chroman-7-yl)benzamide;
(20) 2-((3,4-trans)-4-Hydroxy-3-(pyridin-2-ylmethyl)chroman-7-yl)-N-(neopentylsulfonyl)-benzamide;
(21) 2-((3S,4R)-3-Benzyl-4-hydroxychroman-7-yl)-N-((1-methylcyclopropyl)sulfonyl)-benzamide;
(22) 2-((3R,4S)-3-Benzyl-4-hydroxychroman-7-yl)-N-((1-methylcyclopropyl)sulfonyl)-benzamide;
(23) 2-((3S,4R)-3-Benzyl-4-hydroxychroman-7-yl)-N-(cyclopropylsulfonyl)benzamide;
(24) 2-((3R,4S)-3-Benzyl-4-hydroxychroman-7-yl)-N-(cyclopropylsulfonyl)benzamide;
(25) 2-(Rac-trans)-4-Hydroxy-3-(thiazol-4-ylmethyl)chroman-7-yl)-N-((1-methyl-cyclopropyl)sulfonyl)benzamide;
(26) 4R)-4-Hydroxy-3-(thiazol-4-ylmethyl)chroman-7-yl)-N-((1-methylcyclopropyl)-sulfonyl)benzamide;
(27) 2-(3R,4S)-4-Hydroxy-3-(thiazol-4-ylmethyl)chroman-7-yl)-N-((1-methylcyclopropyl)-sulfonyl)benzamide;
(28) 2-(Rac-trans)-4-Hydroxy-3-((1-methyl-1H-pyrazol-5-yl)methyl)chroman-7-yl)-N-((1-methylcyclopropyl)sulfonyl)benzamide;
(29) 2-((Rac-trans)-4-Hydroxy-3-((5-methyl-1,3,4-thiadiazol-2-yl)methyl)chroman-7-yl)-N-((1-methylcyclopropyl)sulfonyl)benzamide;
(30) 2-((Rac-trans)-3-((1-ethyl-1H-pyrazol-5-yl)methyl)-4-hydroxychroman-7-yl)-N-((1-methylcyclopropyl)sulfonyl)benzamide;
(31) N-(tert-Butylsulfonyl)-2-((rac-trans)-4-hydroxy-3-((5-methyl-1,3,4-thiadiazol-2-yl)methyl)chroman-7-yl)benzamide;
(32) N-(tert-Butylsulfonyl)-2-((rac-trans)-4-hydroxy-3-(thiazol-4-ylmethyl)chroman-7-yl)benzamide;
(33) N-(tert-Butylsulfonyl)-2-((3S,4R)-4-hydroxy-3-(thiazol-4-ylmethyl)chroman-7-yl)benzamide;
(34) N-(tert-Butylsulfonyl)-2-(3R,4S)-4-hydroxy-3-(thiazol-4-ylmethyl)chroman-7-yl)benzamide;
(35) N-(tert-Butylsulfonyl)-2-((rac-trans)-4-hydroxy-3-((1-methyl-1H-pyrazol-5-yl)methyl)chroman-7-yl)benzamide;
(36) N-(tert-Butylsulfonyl)-2-((rac-trans)-3-((1-ethyl-1H-pyrazol-5-yl)methyl)-4-hydroxychroman-7-yl)benzamide;
(37) N-(tert-Butylsulfonyl)-2-((3S,4R)-3-((1-ethyl-1H-pyrazol-5-yl)methyl)-4-hydroxychroman-7-yl)benzamide;
(38) N-(tert-Butylsulfonyl)-2-((3R,4S)-3-((1-ethyl-1H-pyrazol-5-yl)methyl)-4-hydroxychroman-7-yl)benzamide;
(39) 2-((Rac-cis)-3-([1,1'-Biphenyl]-4-ylmethyl)-4-hydroxychroman-7-yl)-4-fluoro-N-((trifluoromethyl)sulfonyl)benzamide;
(40) 2-((Rac-trans)-3-([1,1'-Biphenyl]-4-ylmethyl)-4-hydroxychroman-7-yl)-4-fluoro-N-((trifluoromethyl)sulfonyl)benzamide;
(41) 2-((3R,4S)-3-([1,1'-Biphenyl]-4-ylmethyl)-4-hydroxychroman-7-yl)-4-fluoro-N-((trifluoromethyl)sulfonyl)benzamide;
(42) 2-((3S,4R)-3-([1,1'-Biphenyl]-4-ylmethyl)-4-hydroxychroman-7-yl)-4-fluoro-N-((trifluoromethyl)sulfonyl)benzamide;
(43) 2-(Rac-trans)-4-hydroxy-3-((2-phenyloxazol-4-yl)methyl)chroman-7-yl)-N-((1-methylcyclopropyl)sulfonyl)benzamide;
(44) 2-((3R,4S or 3S,4R)-4-Hydroxy-3-((2-phenyloxazol-4-yl)methyl)chroman-7-yl)-N-((1-methylcyclopropyl)sulfonyl)benzamide;
(45) 2-((3S,4R or 3R,4S)-4-hydroxy-3-((2-phenyloxazol-4-yl)methyl)chroman-7-yl)-N-((1-methylcyclopropyl)sulfonyl)benzamide;
(46) 2-(Rac-trans)-4-Hydroxy-3-((2-phenyloxazol-4-yl)methyl)chroman-7-yl)-N-((1-methylcyclopropyl)sulfonyl)benzamide
(47) N-(tert-Butylsulfonyl)-2-((3R,4S)-4-hydroxy-3-((2-phenyloxazol-4-yl)methyl)chroman-7-yl)benzamide;
(48) N-(tert-Butylsulfonyl)-2-((3S,4R)-4-hydroxy-3-((2-phenyloxazol-4-yl)methyl)chroman-7-yl)benzamide;
(49) 2-((3,4-trans)-4-Hydroxy-3-((R)-1-(pyridin-2-yl)ethyl)chroman-7-yl)-N-((1-methylcyclopropyl)sulfonyl)benzamide; and
(50) 2-((3,4-trans)-4-Hydroxy-3-((S)-1-(pyridin-2-yl)ethyl)chroman-7-yl)-N-((1-methylcyclopropyl)sulfonyl)benzamide;

or a pharmaceutically acceptable salt thereof.

19. A pharmaceutical composition comprising a compound of claim 1, or a pharmaceutically acceptable salt thereof, and a pharmaceutically acceptable carrier.

20. A method of treating type 2 diabetes mellitus in a patient in need of treatment comprising the administration to the patient of a therapeutically effective amount of a compound of claim 1, or a pharmaceutically acceptable salt thereof.

* * * * *